(12) United States Patent
Yamauchi et al.

(10) Patent No.: US 8,178,077 B2
(45) Date of Patent: May 15, 2012

(54) DRUG DEVELOPMENT TARGET PROTEIN AND TARGET GENE, AND METHOD OF SCREENING

(75) Inventors: Tadakazu Yamauchi, Gotenba (JP); Hideaki Sueoka, Osaka (JP); Kouichi Tsuchiya, Tokyo (JP); Katsuhisa Murayama, Osaka (JP); Ken Horiuchi, Hino (JP); Kazuo Komiya, Takarazuka (JP); Morikazu Kito, Kawasaki (JP); Takeshi Tsutsumi, Osaka (JP); Yuko Isono, Yokohama (JP); Yorimasa Suwa, Hino (JP)

(73) Assignee: Reverse Proteomics Research Institute Co., Ltd., Tokyo (JP)

( * ) Notice: Subject to any disclaimer, the term of this patent is extended or adjusted under 35 U.S.C. 154(b) by 1053 days.

(21) Appl. No.: 11/577,575

(22) PCT Filed: Oct. 19, 2005

(86) PCT No.: PCT/JP2005/019645
§ 371 (c)(1),
(2), (4) Date: Oct. 30, 2007

(87) PCT Pub. No.: WO2006/043710
PCT Pub. Date: Apr. 27, 2006

(65) Prior Publication Data
US 2009/0233274 A1 Sep. 17, 2009

(30) Foreign Application Priority Data
Oct. 19, 2004 (JP) .................. 2004-304864

(51) Int. Cl.
*A61K 49/00* (2006.01)
*A01N 43/64* (2006.01)
*C07D 207/00* (2006.01)

(52) U.S. Cl. .................. 424/9; 514/359; 548/400

(58) Field of Classification Search ...... 424/9; 514/359; 548/400
See application file for complete search history.

(56) References Cited

U.S. PATENT DOCUMENTS

| | | | |
|---|---|---|---|
| 5,232,923 | A | 8/1993 | Fakazawa et al. |
| 7,230,155 | B2 | 6/2007 | Nef |
| 2003/0159158 | A1 | 8/2003 | Nef |
| 2004/0115726 | A1 | 6/2004 | Nagashima et al. |

FOREIGN PATENT DOCUMENTS

| | | |
|---|---|---|
| CA | 1 127 164 A | 7/1982 |
| JP | 55-33467 A | 3/1980 |
| JP | 58-55454 A | 4/1983 |
| JP | 1-238524 A | 9/1989 |
| JP | 2003-40801 A | 2/2003 |
| JP | 2004-502669 A | 1/2004 |
| JP | 2004-509406 A | 3/2004 |
| WO | WO 94/07144 A1 | 3/1994 |
| WO | WO 98/09523 A1 | 3/1998 |
| WO | WO 02/02512 A2 | 1/2002 |
| WO | WO 02/098849 A2 | 12/2002 |
| WO | WO 03/040096 A2 | 5/2003 |
| WO | WO 03/041563 A2 | 5/2003 |
| WO | WO 03/072535 A2 | 9/2003 |
| WO | WO 2004/050619 A1 | 6/2004 |

OTHER PUBLICATIONS

Okada et al., *Biochem. J.*, 375: 87-97 (2003).
Drews, *Science*, 287: 1960-1964 (Mar. 17, 2000).
Frantz et al., *Nature Reviews*, 2: 95-96, (Feb. 2003).
Fujii et al., *Chem-Bio Informatics Journal*, 1(1): 18-22 (2001).
Hopkins et al., *Nature Reviews*, 1: 727-730 (Sep. 2002).
Piccioni et al., *Human Molecular Genetics*, 13(4): 437-446 (2004).

*Primary Examiner* — Paul V. Ward
(74) *Attorney, Agent, or Firm* — Leydig, Voit & Mayer, Ltd.

(57) ABSTRACT

The present invention provides novel target proteins and target genes for drug discovery, and the means that enable the development of novel drugs using the same. More particularly, the present invention provides NCS proteins and genes thereof; screening methods for drug (for example, anti-central nervous disease drug); agents for regulating disease (for example, central nervous disease); production methods of a drug derivative; a complex comprising a drug and NCS protein, and a method of producing the complex; a kits comprising a drug or a salt thereof; determination methods for the onset or risk of onset of a specified disease, determination methods for susceptibility to a drug, and determination kits used for the determination methods; and the like.

27 Claims, 2 Drawing Sheets

DRUG DEVELOPMENT TARGET PROTEIN AND TARGET GENE, AND METHOD OF SCREENING

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 11,078 bytes ASCII (Text) file named "701552SequenceListing.txt," created Apr. 18, 2007.

TECHNICAL FIELD OF THE INVENTION

The present invention relates to target proteins and target genes that are useful for the development of drugs such as anti-central nervous disease drug; a screening method for drugs such as anti-central nervous disease drug, and the substance obtained by the screening method; an agent of regulating a pharmacological action such as central nervous action; a drug derivative and a method of producing the derivative; and a complex comprising a drug and a target protein thereof, and a method of producing the complex, and the like.

BACKGROUND ART

Alzheimer's disease (AD) is a type of dementia that affects more than 15 million people of the entire world, and is predicted to affect more in the future, as the average lifetime increases. On the other hand, Down syndrome is a hereditary disease which occurs because of chromosome 21 trisomy (3 copies), and it is known that as Down syndrome patients grow, various AD-like changes in the brain gradually show up, and many Down syndrome patients in their middle ages are affected by AD. Preventing dementia is an important challenge in the aging society, and an effective preventive is strongly desired.

Statins, which are HMG-CoA (3-hydroxy-3-methylglutarylcoenzyme A) reductase inhibitor cholesterol-lowering agents, have been shown by epidemiological studies to have the effect of greatly lowering the occurrence rate of Alzheimer's disease, and expectations for dementia prevention by statins are rising. However, the action mechanism of LDL cholesterol decrease and AD are still unknown, rather a target molecule other than HMG-CoA reductase is speculated to be involved in the decline of AD occurrence rate, and it is necessary to clarify the dementia-related target molecule(s) of statins in order to carry out logical drug discovery for dementia prevention.

In recent years, on the other, the genome sequences of a variety of organisms have been elucidated and analyzed at the global level. For the human genome, in particular, a worldwide cooperative research project was implemented, and completion of analysis of all sequences thereof was announced in April 2003. As a result, it is becoming possible to analyze complex biological phenomena in the context of the functions and control of all genes, or networks of gene-gene, protein-protein, cell-cell, and individual-individual interactions. The genome information thus obtained has been significantly revolutionizing a number of industries, including drug development, as well as in academic sectors.

For example, it has been reported that there are about 480 kinds of target proteins for drugs having been in common use to date, and that these target proteins are limited to membrane receptors, enzymes, ion channels, or nuclear receptors and the like (J. Drews, Science, 287, 1960-1964, 2000). Meanwhile, target protein search based on genome information has discovered an extremely large number of target proteins, including novel proteins not covered in the conventional range of target proteins one after another, which are estimated to total about 1,500 kinds (A. L. Hopkins & C. R. Groom, Nature Reviews; Drug Discovery, 1, 727-730, 2002).

However, despite the fact that the research and development expenditures spent by pharmaceutical companies are increasing due to rises in infrastructuring costs for coping with vast amounts of data like genome information and clinical developmental costs, the number of new drugs approved per year is tending to decrease on the contrary (Nature Reviews; Drug Discovery, February, 2003). This shows that the above-described genome information is actually not efficiently utilized.

As a means for overcoming these circumstances, Nagashima et al. invented "Method, System, Apparatus, and Device for Discovering and Preparing Chemical for Medical and Other Uses" and filed a patent application for that invention (Japanese Patent Kohyo Publication No. 2004-509406).

Disclosed in that patent application are methods, systems, databases, user interfaces, software, media, and services that are useful for the evaluation of compound-protein interactions, and are also useful for the utilization of the information resulting from such an evaluation intended to discover compounds in medical and other areas. Furthermore, it is intended to produce a very large pool of novel target proteins for drug discovery, novel methods for designing novel drugs, and a pool of small substances for therapeutic purposes that are virtually synthesized as having been inconceivable in the past.

Specifically, disclosed in that patent application were a method of identifying a protein or partial protein that is appropriate as a novel drug discovery target, which comprises the following steps:
(i) a step for selecting a plurality of proteins or partial proteins showing desired affinity and specificity for a selected target compound;
(ii) a step for identifying the structure and function of the protein or the partial protein; and
(iii) a step for selecting a single protein or single partial protein having a desired function, and a method of discovering a drug, which comprises the following steps:
(i) a step for investigating the chemical structure of the target compound selected using the above-described method; and
(ii) a step for chemically modifying the structure of the selected target compound to optimize the affinity and specificity of the modified compound for the protein or the partial protein, which is appropriate as a novel drug target.

Furthermore, another feature of the method disclosed in that patent application resides in that the selected target compound is a compound approved for medical use.

Conventional drugs that have been used to date include many drugs for which target proteins are unknown, or for which target proteins are known but not all of whose pharmacological effects and adverse effects can be explained by mechanisms mediated by the proteins.

Typically, aspirin, one of the drugs that have longest been used, may be mentioned. When aspirin was launched in the market for the first time more than 100 years ago, the mechanism for its anti-inflammatory action was unclear. About 70 years later, aspirin was found to have cyclooxygenase (COX) inhibitory action. Still 20 years later, it was demonstrated that COX occurred in two subtypes: COX-1 and COX-2, that the primary pharmacological effect of aspirin was based on COX-2 inhibition, and that COX-1 inhibitory action was the cause of adverse effects such as gastrointestinal disorders. However, not all the target proteins for aspirin have been elucidated. In recent years, aspirin has been shown to exhibit anticancer action and antidementic action in clinical settings, but these pharmacological effects cannot be explained by COX inhibition. On the other, recent years have seen many papers reporting that aspirin acts on transcription factors such as IKKβ and on nuclear receptors such as PPAR-γ, but the relationship between these and the various pharmacological effects of aspirin remains unclear.

For these reasons, elucidating target proteins for traditionally used drugs can be said to be a very effective approach to discovering novel drug discovery target proteins.

Hirayama, one of the inventors of the above-described published patent, and others generated a database integrating the structural and physical property data on about 1,500 kinds of drugs commercially available in Japan, and found that existing pharmaceutical compounds share structural features (Chem-Bio Informatics Journal, 1, 18-22, 2001). Drugs that have been commonly used to date can be described as excellent in that they have cleared the issues of localization in the body and safety in their developmental processes. Searching novel target proteins with these existing drugs as probes, and selecting novel new drug candidate compounds on the basis of their structures is thought to be a highly reasonable and efficient approach.

A second problem arises concerning how to make use of the genome information during the search for novel target proteins. Solely determining the genome sequence is not sufficient to ensure the elucidation of the functions of all genes and the discovery of drug discovery target proteins. It is estimated that in humans, about 30,000 to 40,000 kinds of genes are present; taking into consideration variants from alternative splicing, there are reportedly more than 100,000 kinds of mRNA. It is important, therefore, that out of the vast amount of new genes revealed from the genome sequence, those having useful functions in industrial applications, including drug development, should be efficiently selected and identified.

In many cases of the genome sequences of eukaryotic organisms, each gene is divided into a plurality of exons by introns; therefore, it is impossible to accurately predict the structure of the protein encoded by the gene solely from the sequence information on the gene. In contrast, for a cDNA prepared from intron-excluded mRNA, information on the amino acid sequence of protein is obtained as information on a single continuous sequence, enabling easy determination of the primary structure thereof.

In particular, analyzing a full-length cDNA enables the identification of the mRNA transcription initiation point on the genome sequence based on the 5'-terminal sequence of the cDNA, and also enables analysis of factors involved in the stability of mRNA contained in the sequence and the expression control in the translation stage. Also, because the ATG codon, which serves as the translation initiation point, is present on the 5' side, translation into protein in the right frame can be achieved. Therefore, by using an appropriate gene expression system, it is also possible to mass-produce the protein encoded by the cDNA, and to express the protein and analyze the biological activity thereof. Hence, it is considered that by performing an analysis using a protein expressed from full-length cDNA, important information that could not be obtained solely by genome sequence analysis is obtained, and that it is possible to discover novel target proteins that do not lie in the conventional category of drug discovery target proteins.

USP publication no. 20030159158 (Nef, Patrick, Aug. 21, 2003) discloses a screening method for an NCS1 agonist targeting NCS1, which is a kind of NCS. However, there is a plurality of molecular species of NCS, which is expressed specifically or complementarily in various tissues such as the cerebral nerve tissue, secretory tissue, immuno-related cells, epithelium of blood vessels, and relates to many functions. Hence, screening or designing directed to compounds with structures that are preferred for NCS binding is necessary in order to efficiently produce new pharmaceutical compounds that target the NCS family. The present invention discloses preferred structures for NCS binding, of which many in addition have structural motifs that exist in common drugs. For this reason, by taking the structure disclosed in the present invention as the starting point, it will be possible to efficiently screen or design a compound of high drug efficacy and safety. Furthermore, a screening method targeting NCS1 is disclosed in USP publication 20030159158. However, the NCS-binding compound and its screening method in the present application is directed to neurocalcin δ that belongs to the VILIPS family (Class B) and human hippocalcin-like protein 1 (or Visinin-like protein 3 or VILIP-3), which are indicated to be related to central nervous diseases, especially to dementia such as Alzheimer's disease, making it especially preferable for the development of therapeutic drugs for central nervous diseases centered around dementia. Note however, that the NCS-binding compound disclosed in the present invention is not limited to the VILIPS family (Class B), but comprises compounds that bind to the whole NCS family, including NCS 1.

DISCLOSURE OF THE INVENTION

The objects of the present invention are to provide target proteins for drug discovery and compounds binding thereto, target genes for drug discovery, the various means that enable the development of novel medicines utilizing the above, and the like.

The present inventors diligently investigated new drug discovery target proteins that can be useful for the development of new drugs, by analyzing by the SEC/MS method, the interactions between human proteins and compounds that have been used as drugs, and found that the neuron-specific calcium ion sensor protein (NCS protein) can be a target protein for creating a drug such as an anti-central nervous disease drug. Based on these findings, the present inventors conceived that compounds capable of binding to the NCS protein, and substances which regulate the expression or function of the NCS protein gene are substances which can be useful as drugs, and that in order to develop drugs such as anti-central nervous disease drugs, we can screen substances capable of binding to the NCS protein, or substances that regulate the expression or function of the NCS protein gene, or we derivatize drugs so as to be able to regulate the function of the NCS protein by binding thereto, or to regulate the expression or function of the NCS protein gene, and completed the present invention.

Accordingly, the present invention is as follows:

[1] A compound capable of binding to an NCS protein, which is selected from the group consisting of the following formulas (I) to (VIII), or a salt thereof;

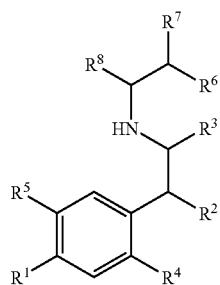 (I)

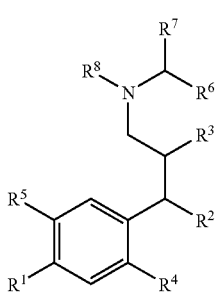 (II)

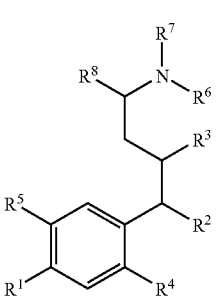 (III)

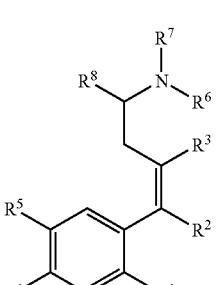 (IV)

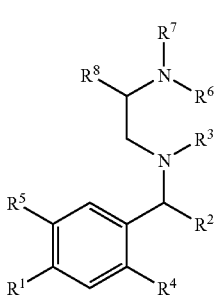 (V)

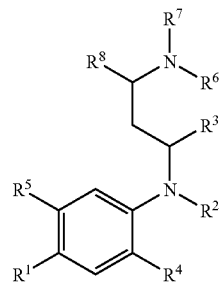 (VI)

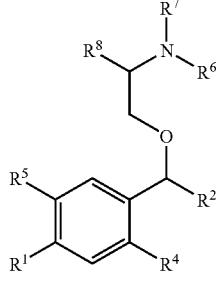 (VII)

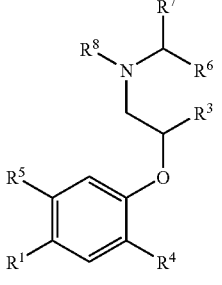 (VIII)

wherein $R^1$ is a hydrogen atom; a halogen atom; cyano; hydroxy; straight chain or branched alkyl having 1 to 7 carbon atoms; halogenated alkyl; alkyloxy; alkylsulfanyl; straight chain or branched alkyl having 1 to 5 carbon atoms, straight chain or branched alkyloxy having 1 to 5 carbon atoms, phenyl, phenylsulfanyl, phenylalkyl having 7 to 12 carbon atoms, phenylalkenyl having 8 to 12 carbon atoms or phenylalkyloxy having 7 to 12 carbon atoms, each of which optionally has 1 to 3 substituents selected from the group consisting of a halogen atom, cyano, hydroxy, amino, mono-substituted amino, di-substituted amino, straight chain or branched alkyl having 1 to 5 carbon atoms, halogenated alkyl, alkyloxy and alkylsulfanyl; or —CO—$R^9$ (wherein $R^9$ is straight chain or branched alkyl having 1 to 9 carbon atoms; or phenyl, cycloalkyl having 3 to 7 carbon atoms, phenylalkyl having 7 to 11 carbon atoms, imidazolyl, biphenyl, thienyl, benzothienyl or benzofuryl, each of which optionally has 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl, halogenated methyl and 4-hydroxyphenyl), $R^2$ is a hydrogen atom; a halogen atom; cyano; hydroxy; straight chain or branched alkyl having 1 to 7 carbon atoms; halogenated alkyl; alkyloxy; alkylsulfanyl; or straight chain or branched alkyl having 1 to 5 carbon atoms, straight chain or branched alkyloxy having 1 to 5 carbon atoms, phenyl, phenyloxy, phenylsulfanyl, phenylalkyl having 7 to 12 carbon atoms, phenylalkenyl having 8 to 12 carbon atoms or phenylalkyloxy having 7 to 12 carbon atoms, each of which optionally has 1 to 3 substituents selected from the group consisting of a halogen atom, cyano, hydroxy, amino, mono-substituted amino, di-substituted amino, straight chain or branched alkyl having 1 to 5 carbon atoms, halogenated alkyl, alkyloxy and alkylsulfanyl, $R^3$ is a hydrogen atom; a halogen atom; cyano; hydroxy; straight chain or branched alkyl having 1 to 7 carbon atoms; halogenated alkyl; alkyloxy; alkylsulfanyl; or straight chain or branched alkyl having 1 to 5 carbon atoms, straight chain or branched alkyloxy having 1 to 5 carbon atoms, phenyl, phenylsulfanyl, phenylalkyl having 7 to 12 carbon atoms, phenylalkenyl having 8 to 12 carbon atoms or phenylalkyloxy having 7 to 12 carbon atoms, each of which optionally has 1 to 3 substituents selected from the group consisting of a halogen atom, cyano, hydroxy, amino, mono-substituted amino, di-substituted amino, straight chain or branched alkyl having 1 to 5 carbon atoms, halogenated alkyl, alkyloxy and alkylsulfanyl, $R^4$ is a hydrogen atom; a halogen atom; cyano; hydroxy; straight chain or branched alkyl having 1 to 7 carbon atoms; halogenated alkyl; alkyloxy; alkylsulfanyl; or straight chain or branched alkyl having 1 to 5 carbon atoms, straight chain or branched alkyloxy having 1 to 5 carbon atoms, phenyl, phenylsulfanyl, phenylimino, phenylalkyl having 7 to 12 carbon atoms, phenylalkenyl having 8 to 12 carbon atoms or phenylalkyloxy having 7 to 12 carbon atoms, each of which optionally has 1 to 3 substituents selected from the group consisting of a halogen atom, cyano, hydroxy, amino, mono-substituted amino, di-substituted amino, straight chain or branched alkyl having 1 to 5 carbon atoms, halogenated alkyl, alkyloxy and alkylsulfanyl, $R^5$ is a hydrogen atom; a halogen atom; cyano; straight chain or branched alkyl having 1 to 5 carbon atoms; or halogenated alkyl, $R^6$ is a hydrogen atom; a halogen atom; cyano; hydroxy; straight chain or branched alkyl having 1 to 7 carbon atoms; halogenated alkyl; alkyloxy; alkylsulfanyl; or straight chain or branched alkyl having 1 to 5 carbon atoms, straight chain or branched alkyloxy having 1 to 5 carbon atoms, phenyl, phenylsulfanyl, phenylalkyl having 7 to 12 carbon atoms, phenylalkenyl having 8 to 12 carbon atoms or phenylalkyloxy having 7 to 12 carbon atoms, each of which optionally has 1 to 3 substituents selected from the group consisting of a halogen atom, cyano, hydroxy, amino, mono-substituted amino, di-substituted amino, straight chain or branched alkyl having 1 to 5 carbon atoms, halogenated alkyl, alkyloxy and alkylsulfanyl, $R^7$ is a hydrogen atom; a halogen atom; cyano; hydroxy; straight chain or branched alkyl having 1 to 7 carbon atoms; halogenated alkyl; alkyloxy; alkylsulfanyl; or straight chain or branched alkyl having 1 to 5 carbon atoms, straight chain or branched alkyloxy having 1 to 5 carbon atoms, phenyl, phenylsulfanyl, phenylalkyl having 7 to 12 carbon atoms, phenylalkenyl having 8 to 12 carbon atoms or phenylalkyloxy having 7 to 12 carbon atoms, each of which optionally has 1 to 3 substituents selected from the group consisting of a halogen atom, cyano, hydroxy, amino, mono-substituted amino, di-substituted amino, straight chain or branched alkyl having 1 to 5 carbon atoms, halogenated alkyl, alkyloxy and alkylsulfanyl, and $R^8$ is a hydrogen atom; a halogen atom; cyano; hydroxy; alkylsulfanyl; or straight chain or branched alkyl having 1 to 7 carbon atoms or straight chain or branched alkyloxy having 1 to 7 carbon atoms, each of which optionally has 1 to 3 substituents selected from the group consisting of a halogen atom, cyano, hydroxy, halogenated alkyl and alkyloxy, provided that each of $R^2$ and $R^4$ bonded to each other, $R^3$ and $R^6$ bonded to each other, $R^6$ and $R^7$ bonded to each other, and $R^7$ and $R^8$ bonded to each other may independently forms a ring optionally having 1 to 3 substituents selected from the group consisting of a halogen atom; cyano; hydroxy; amino; mono-substituted amino; di-substituted amino; halogenated alkyl; alkylsulfanyl; benzimidazolonyl; and straight chain or branched alkyl having 1 to 5 carbon atoms or straight chain or branched alkyloxy having 1 to 5 carbon atoms, each of which optionally has 1 to 3 substituents selected from the group consisting of a halogen atom, cyano, hydroxy, amino, mono-substituted amino, di-substituted amino, alkyloxy and alkylsulfanyl.

[2] A drug for the treatment or prophylaxis of dementia, which comprises a compound selected from the group consisting of the following formulas (I) to (VIII), or a pharmaceutically acceptable salt thereof, as an active ingredient;

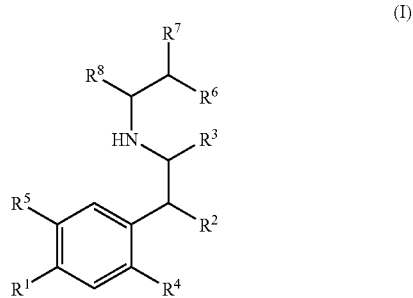

(I)

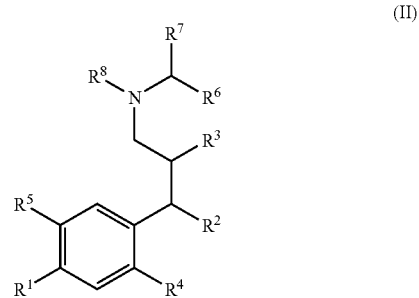

(II)

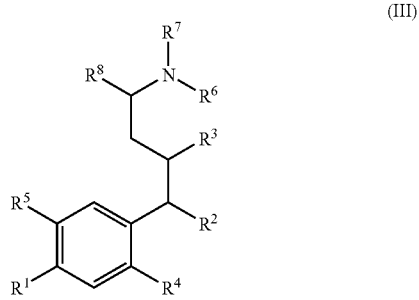

(III)

-continued

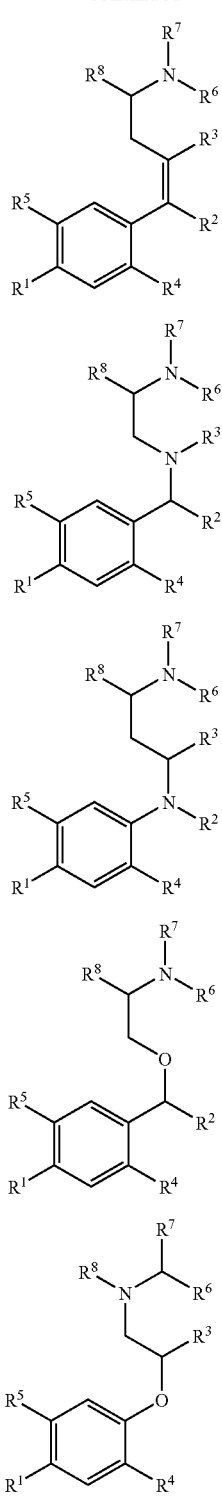

wherein
R¹ is a hydrogen atom; a halogen atom; cyano; hydroxy; straight chain or branched alkyl having 1 to 7 carbon atoms; halogenated alkyl; alkyloxy; alkylsulfanyl; straight chain or branched alkyl having 1 to 5 carbon atoms, straight chain or branched alkyloxy having 1 to 5 carbon atoms, phenyl, phenylsulfanyl, phenylalkyl having 7 to 12 carbon atoms, phenylalkenyl having 8 to 12 carbon atoms or phenylalkyloxy having 7 to 12 carbon atoms, each of which optionally has 1 to 3 substituents selected from the group consisting of a halogen atom, cyano, hydroxy, amino, mono-substituted amino, di-substituted amino, straight chain or branched alkyl having 1 to 5 carbon atoms, halogenated alkyl, alkyloxy and alkylsulfanyl; or —CO—R⁹ (wherein R⁹ is straight chain or branched alkyl having 1 to 9 carbon atoms; or phenyl, cycloalkyl having 3 to 7 carbon atoms, phenylalkyl having 7 to 11 carbon atoms, imidazolyl, biphenyl, thienyl, benzothienyl or benzofuryl, each of which optionally has 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl, halogenated methyl and 4-hydroxyphenyl), R² is a hydrogen atom; a halogen atom; cyano; hydroxy; straight chain or branched alkyl having 1 to 7 carbon atoms; halogenated alkyl; alkyloxy; alkylsulfanyl; or straight chain or branched alkyl having 1 to 5 carbon atoms, straight chain or branched alkyloxy having 1 to 5 carbon atoms, phenyl, phenyloxy, phenylsulfanyl, phenylalkyl having 7 to 12 carbon atoms, phenylalkenyl having 8 to 12 carbon atoms or phenylalkyloxy having 7 to 12 carbon atoms, each of which optionally has 1 to 3 substituents selected from the group consisting of a halogen atom, cyano, hydroxy, amino, mono-substituted amino, di-substituted amino, straight chain or branched alkyl having 1 to 5 carbon atoms, halogenated alkyl, alkyloxy and alkylsulfanyl, R³ is a hydrogen atom; a halogen atom; cyano; hydroxy; straight chain or branched alkyl having 1 to 7 carbon atoms; halogenated alkyl; alkyloxy; alkylsulfanyl; or straight chain or branched alkyl having 1 to 5 carbon atoms, straight chain or branched alkyloxy having 1 to 5 carbon atoms, phenyl, phenylsulfanyl, phenylalkyl having 7 to 12 carbon atoms, phenylalkenyl having 8 to 12 carbon atoms or phenylalkyloxy having 7 to 12 carbon atoms, each of which optionally has 1 to 3 substituents selected from the group consisting of a halogen atom, cyano, hydroxy, amino, mono-substituted amino, di-substituted amino, straight chain or branched alkyl having 1 to 5 carbon atoms, halogenated alkyl, alkyloxy and alkylsulfanyl, R⁴ is a hydrogen atom; a halogen atom; cyano; hydroxy; straight chain or branched alkyl having 1 to 7 carbon atoms; halogenated alkyl; alkyloxy; alkylsulfanyl; or straight chain or branched alkyl having 1 to 5 carbon atoms, straight chain or branched alkyloxy having 1 to 5 carbon atoms, phenyl, phenylsulfanyl, phenylimino, phenylalkyl having 7 to 12 carbon atoms, phenylalkenyl having 8 to 12 carbon atoms or phenylalkyloxy having 7 to 12 carbon atoms, each of which optionally has 1 to 3 substituents selected from the group consisting of a halogen atom, cyano, hydroxy, amino, mono-substituted amino, di-substituted amino, straight chain or branched alkyl having 1 to 5 carbon atoms, halogenated alkyl, alkyloxy and alkylsulfanyl, R⁵ is a hydrogen atom; a halogen atom; cyano; straight chain or branched alkyl having 1 to 5 carbon atoms; or halogenated alkyl, R⁶ is a hydrogen atom; a halogen atom; cyano; hydroxy; straight chain or branched alkyl having 1 to 7 carbon atoms; halogenated alkyl; alkyloxy; alkylsulfanyl; or straight chain or branched alkyl having 1 to 5 carbon atoms, straight chain or branched alkyloxy having 1 to 5 carbon atoms, phenyl, phenylsulfanyl, phenylalkyl having 7 to 12 carbon atoms, phenylalkenyl having 8 to 12 carbon atoms or phenylalkyloxy having 7 to 12 carbon atoms, each of which optionally has 1 to 3 substituents selected from the group consisting of a halogen atom, cyano, hydroxy, amino, mono-substituted amino, di-substituted amino, straight chain or branched alkyl having 1 to 5 carbon atoms, halogenated alkyl, alkyloxy and alkylsulfanyl, $R^7$ is a hydrogen atom; a halogen atom; cyano; hydroxy; straight chain or branched alkyl having 1 to 7 carbon atoms; halogenated alkyl; alkyloxy; alkylsulfanyl; or straight chain or branched alkyl having 1 to 5 carbon atoms, straight chain or branched alkyloxy having 1 to 5 carbon atoms, phenyl, phenylsulfanyl, phenylalkyl having 7 to 12 carbon atoms, phenylalkenyl having 8 to 12 carbon atoms or phenylalkyloxy having 7 to 12 carbon atoms, each of which optionally has 1 to 3 substituents selected from the group consisting of a halogen atom, cyano, hydroxy, amino, mono-substituted amino, di-substituted amino, straight chain or branched alkyl having 1 to 5 carbon atoms, halogenated alkyl, alkyloxy and alkylsulfanyl, and $R^8$ is a hydrogen atom; a halogen atom; cyano; hydroxy; alkylsulfanyl; or straight chain or branched alkyl having 1 to 7 carbon atoms or straight chain or branched alkyloxy having 1 to 7 carbon atoms, each of which optionally has 1 to 3 substituents selected from the group consisting of a halogen atom, cyano, hydroxy, halogenated alkyl and alkyloxy, provided that each of $R^2$ and $R^4$ bonded to each other, $R^3$ and $R^6$ bonded to each other, $R^6$ and $R^7$ bonded to each other, and $R^7$ and $R^8$ bonded to each other may independently forms a ring optionally having 1 to 3 substituents selected from the group consisting of a halogen atom; cyano; hydroxy; amino; mono-substituted amino; di-substituted amino; halogenated alkyl; alkylsulfanyl; benzimidazolonyl; and straight chain or branched alkyl having 1 to 5 carbon atoms or straight chain or branched alkyloxy having 1 to 5 carbon atoms, each of which optionally has 1 to 3 substituents selected from the group consisting of a halogen atom, cyano, hydroxy, amino, mono-substituted amino, di-substituted amino, alkyloxy and alkylsulfanyl.

[3] A compound capable of binding to an NCS protein, which is selected from the group consisting of the following formulas (1') to (11'), or a salt thereof; a compound represented by the formula (1'):

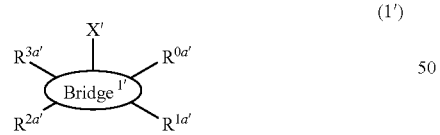
(1')

wherein

Bridge$^{1\prime}$ is a bridge structure selected from the group consisting of the following formulas (1a') to (1j'):

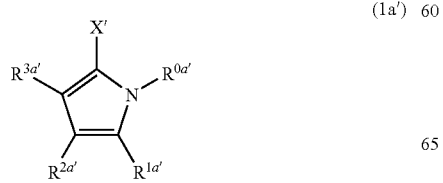
(1a')

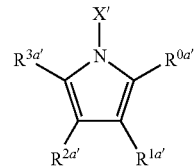
(1b')

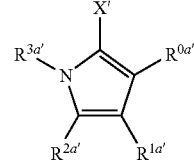
(1c')

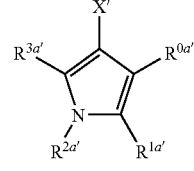
(1d')

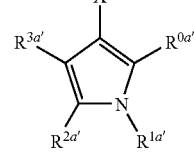
(1e')

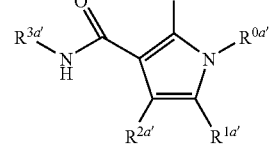
(1f')

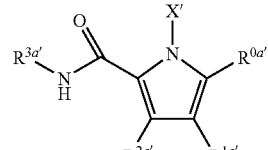
(1g')

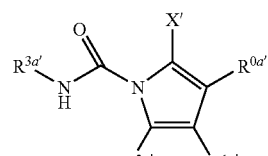
(1h')

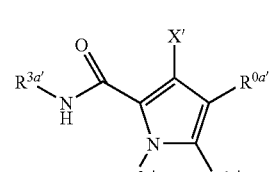
(1i')

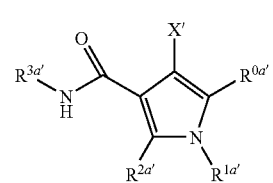
(1j')

$R^{1a'}$ is phenyl optionally having 1 to 3 substituents selected from the group consisting of straight chain or branched alkyl having 1 to 9 carbon atoms, a halogen atom, cyano, hydroxy and amino; or phenyl substituted by $R^{4a'}$, $R^{2a'}$ is straight chain or branched alkyl having 1 to 9 carbon atoms; phenyl, cycloalkyl having 3 to 7 carbon atoms, phenylalkyl having 7 to 11 carbon atoms, imidazolyl, biphenyl, thienyl, benzothienyl or benzofuryl, each of which optionally has 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl and halogenated methyl; or phenyl, imidazolyl, biphenyl, thienyl, benzothienyl or benzofuryl, each of which is substituted by $R^{5a'}$, $R^{3a'}$ is a hydrogen atom; straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, amino, mono-substituted amino, di-substituted amino, alkylsulfanyl and halogenated methyl; or a straight chain or branched alkyl group having 1 to 5 carbon atoms, cycloalkyl having 3 to 7 carbon atoms, phenyl, biphenyl, piperidinyl, piperazinyl, imidazolyl, benzimidazolonyl or morpholinyl, each of which is substituted by $R^{6a'}$, and X' is a hydrogen atom or straight chain or branched alkyl having 1 to 5 carbon atoms, provided that any one of $R^{0a'}$, $R^{4a'}$, $R^{5a'}$ and $R^{6a'}$ is optionally a group selected from the group consisting of the formulas (1B) to (1D):

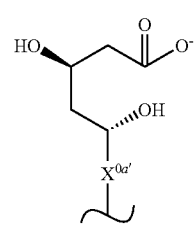
(1B)

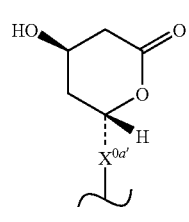
(1C)

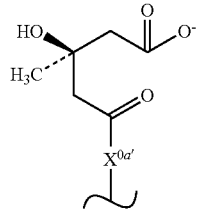
(1D)

wherein $X^{0a'}$ is straight chain or branched alkylene having 1 to 5 carbon atoms;

a compound represented by the formula (2'):

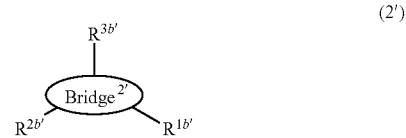
(2')

wherein

Bridge²' is a bridge structure selected from the group consisting of the following formulas (2a') to (2r'):

(2a')

(2b')

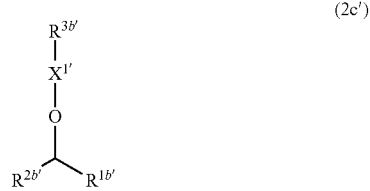
(2c')

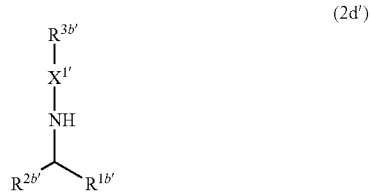
(2d')

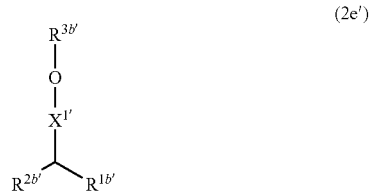
(2e')

(2f')

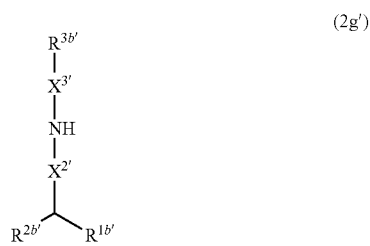
(2g')

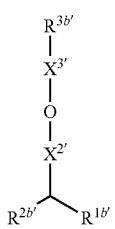 (2h')

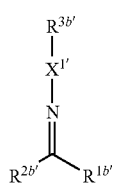 (2i')

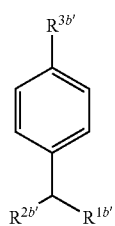 (2j')

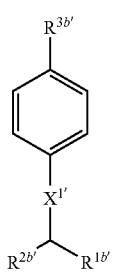 (2k')

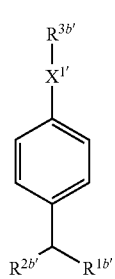 (2l')

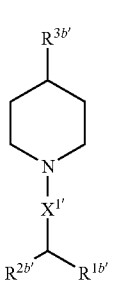 (2m')

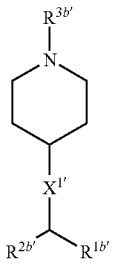 (2n')

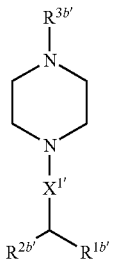 (2o')

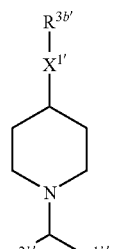 (2p')

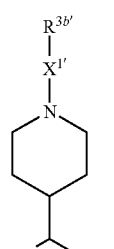 (2q')

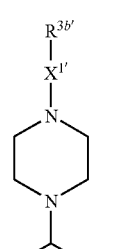 (2r')

wherein $X^{1\prime}$ is straight chain or branched alkylene having 1 to 5 carbon atoms, straight chain or branched alkenylene having 2 to 5 carbon atoms or straight chain or branched alkynylene having 2 to 5 carbon atoms, and $X^{2\prime}$ and $X^3$ are each independently straight chain or branched alkylene having 1 to 3 carbon atoms, straight chain or branched alkenylene having 2 to 3 carbon atoms or alkynylene having 2 to 3 carbon atoms, $R^{1b\prime}$ is phenyl optionally having 1 to 3 substituents selected from the group consisting of straight chain or branched alkyl having 1 to 9 carbon atoms, a halogen atom, cyano, hydroxy and amino; or phenyl substituted by $R^{4b\prime}$, $R^{2b'}$ is straight chain or branched alkyl having 1 to 9 carbon atoms; phenyl, cycloalkyl having 3 to 7 carbon atoms, phenylalkyl having 7 to 11 carbon atoms, imidazolyl, biphenyl, thienyl, benzothienyl or benzofuryl, each of which optionally has 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl and halogenated methyl; or phenyl, imidazolyl, biphenyl, thienyl, benzothienyl or benzofuryl, each of which is substituted by $R^{5b'}$, and $R^{3b'}$ is a hydrogen atom; straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, amino, mono-substituted amino, di-substituted amino, alkylsulfanyl and halogenated methyl; or a straight chain or branched alkyl group having 1 to 5 carbon atoms, cycloalkyl having 3 to 7 carbon atoms, phenyl, biphenyl, piperidinyl, piperazinyl, imidazolyl, benzimidazolonyl or morpholinyl, each of which is substituted by $R^{6b'}$, provided that any one of $R^{4b'}$, $R^{5b'}$ and $R^{6b'}$ is optionally a group selected from the group consisting of the formulas (2B) to (2D):

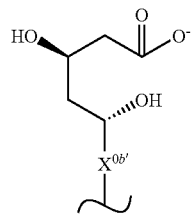

(2B)

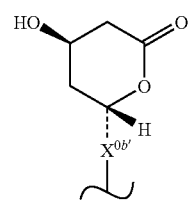

(2C)

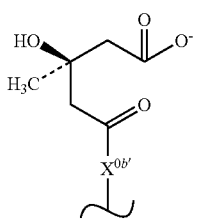

(2D)

wherein $X^{0b'}$ is straight chain or branched alkylene having 1 to 5 carbon atoms;

a compound represented by the formula (3'):

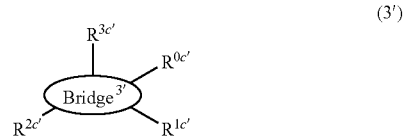

(3')

wherein
Bridge$^{3'}$ is a bridge structure selected from the group consisting of the following formulas (3a') to (3f'):

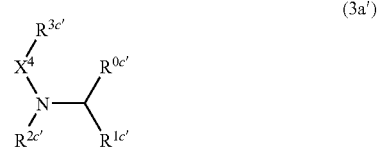

(3a')

(3b')

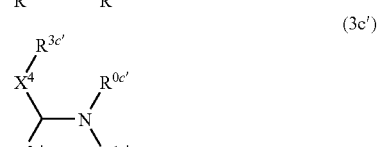

(3c')

(3d')

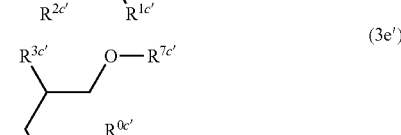

(3e')

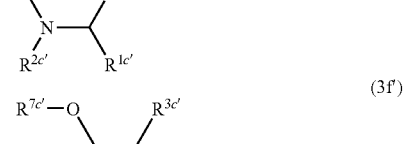

(3f')

wherein $X^4$ is straight chain or branched alkylene having 1 to 5 carbon atoms, and $R^{7c'}$ is straight chain or branched alkyl having 1 to 5 carbon atoms, $R^{1c'}$ is phenyl optionally having 1 to 3 substituents selected from the group consisting of straight chain or branched alkyl having 1 to 9 carbon atoms, a halogen atom, cyano, hydroxy and amino; or phenyl substituted by $R^{4c'}$, $R^{2c'}$ is straight chain or branched alkyl having 1 to 9 carbon atoms; phenyl, cycloalkyl having 3 to 7 carbon atoms, phenylalkyl having 7 to 11 carbon atoms, imidazolyl, biphenyl, thienyl, benzothienyl or benzofuryl, each of which optionally has 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl and halogenated methyl; or phenyl, imidazolyl, biphenyl, thienyl, benzothienyl or benzofuryl, each of which is substituted by $R^{5c\prime}$, and $R^{3c\prime}$ is a hydrogen atom; straight chain or branched alkyl having 1 to 5 carbon atoms, cycloalkyl having 3 to 7 carbon atoms, phenyl, biphenyl, pyrrolidinyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, amino, mono-substituted amino, di-substituted amino, alkylsulfanyl and halogenated methyl; or a straight chain or branched alkyl group having 1 to 5 carbon atoms, cycloalkyl having 3 to 7 carbon atoms, phenyl, biphenyl, pyrrolidinyl, piperidinyl, piperazinyl, imidazolyl, benzimidazolonyl or morpholinyl, each of which is substituted by $R^{6c\prime}$, provided that any one of $R^{0c\prime}$, $R^{4c\prime}$, $R^{5c\prime}$, $R^{6c\prime}$ and $R^{7c\prime}$ is optionally a group selected from the group consisting of the formulas (3B) to (3D):

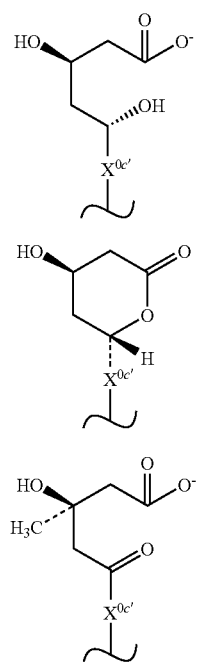

wherein $X^{0c\prime}$ is straight chain or branched alkylene having 1 to 5 carbon atoms;

a compound represented by the formula (4'):

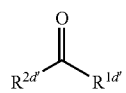

wherein $R^{1d\prime}$ is phenyl optionally having 1 to 3 substituents selected from the group consisting of straight chain or branched alkyl having 1 to 9 carbon atoms, a halogen atom, cyano, hydroxy and amino; or phenyl substituted by $R^{4d\prime}$, $R^{2d\prime}$ is straight chain or branched alkyl having 1 to 9 carbon atoms; or phenyl, cycloalkyl having 3 to 7 carbon atoms, phenylalkyl having 7 to 11 carbon atoms, imidazolyl, biphenyl, thienyl, benzothienyl or benzofuryl, each of which optionally has 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl, halogenated methyl and $R^{5d\prime}$, $R^{4d\prime}$ is optionally a group represented by the formula (d1'):

wherein $X^{5\prime}$ is straight chain or branched alkylene having 1 to 5 carbon atoms, and $R^{5d\prime}$ is 4-hydroxyphenyl, provided that any one of $R^{4d\prime}$ and $R^{5d\prime}$ is optionally a group selected from the group consisting of the formulas (4B) to (4D):

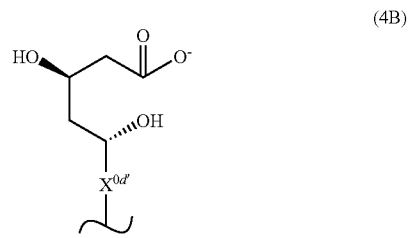

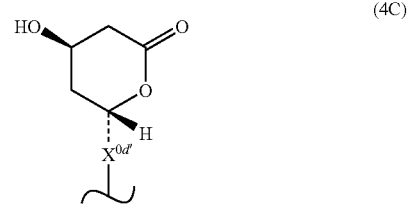

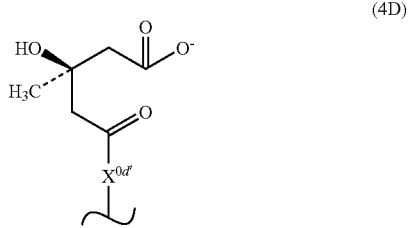

wherein $X^{0d\prime}$ is straight chain or branched alkylene having 1 to 5 carbon atoms;

a compound represented by the formula (5'):

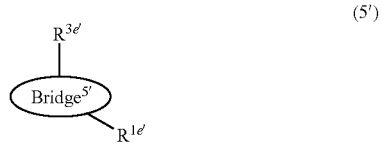

wherein

Bridge$^{5'}$ is a bridge structure represented by the following formula (5a'):

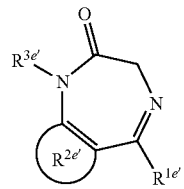

(5a')

wherein R$^{2e'}$ is benzene, cycloalkane having 3 to 7 carbon atoms, imidazole, biphenyl, thiophene, benzothiophene or benzofuran, each of which optionally has 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl and halogenated methyl; or benzene, imidazole, biphenyl, thiophene, benzothiophene or benzofuran, each of which is substituted by R$^{5e'}$, R$^{1e'}$ is phenyl optionally having 1 to 3 substituents selected from the group consisting of straight chain or branched alkyl having 1 to 9 carbon atoms, a halogen atom, cyano, hydroxy and amino; or phenyl substituted by R$^{4e'}$, and R$^{3e'}$ is a hydrogen atom; straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, amino, mono-substituted amino, di-substituted amino, alkylsulfanyl and halogenated methyl; or a straight chain or branched alkyl group having 1 to 5 carbon atoms, cycloalkyl having 3 to 7 carbon atoms, phenyl, biphenyl, piperidinyl, piperazinyl, imidazolyl, benzimidazolonyl or morpholinyl, each of which is substituted by R$^{6e'}$, provided that any one of R$^{3e'}$, R$^{4e'}$, R$^{5e'}$ and R$^{6e'}$ is optionally a group selected from the group consisting of the formulas (5B) to (5D):

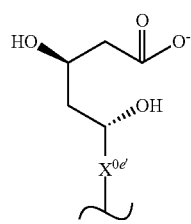

(5B)

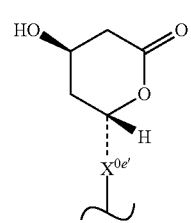

(5C)

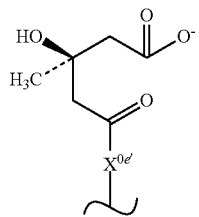

(5D)

wherein X$^{0e'}$ is straight chain or branched alkylene having 1 to 5 carbon atoms;

a compound represented by the formula (6'):

(6')

wherein

Bridge$^{6'}$ is a bridge structure selected from the group consisting of the following formulas (6a') to (6g'):

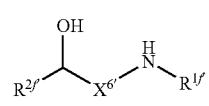

(6a')

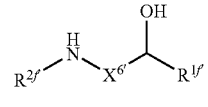

(6b')

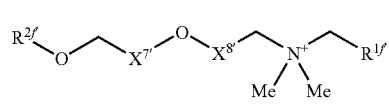

(6c')

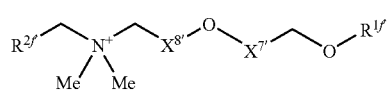

(6d')

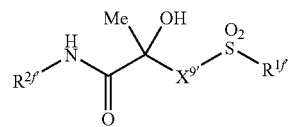

(6e')

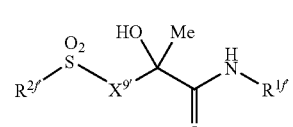

(6f')

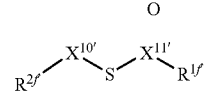

(6g')

wherein X$^{6'}$ and X$^{9'}$ are each independently straight chain or branched alkylene having 1 to 5 carbon atoms, and X$^{7'}$, X$^{8'}$, X$^{10'}$ and X$^{11'}$ are each independently straight chain or branched alkylene having 1 to 3 carbon atoms, R$^{1f'}$ is phenyl optionally having 1 to 3 substituents selected from the group consisting of straight chain or branched alkyl having 1 to 9 carbon atoms, a halogen atom, cyano, hydroxy and amino; or phenyl substituted by R$^{4f'}$, and R$^{2f'}$ is straight chain or branched alkyl having 1 to 9 carbon atoms; phenyl, cycloalkyl having 3 to 7 carbon atoms, phenylalkyl having 7 to 11 carbon atoms, imidazolyl, biphenyl, thienyl, benzothienyl or benzofuryl, each of which optionally has 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl and halogenated methyl; a group represented by the formula (f1'):

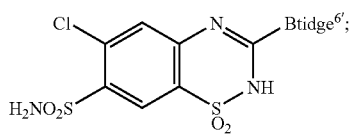

(f1')

or phenyl, imidazolyl, biphenyl, thienyl, benzothienyl or benzofuryl, each of which substituted by $R^{5f'}$, provided that any one of $R^{4f'}$ and $R^{5f'}$ is optionally a group selected from the group consisting of the formulas (6B) to (6D):

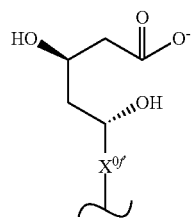

(6B)

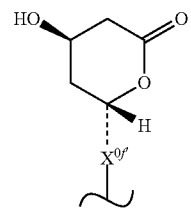

(6C)

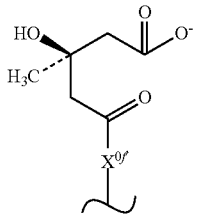

(6D)

wherein $X^{0f'}$ is straight chain or branched alkylene having 1 to 5 carbon atoms;

a compound represented by the formula (7'):

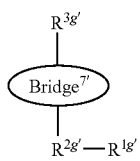

(7')

wherein
Bridge$^{7'}$ is a bridge structure represented by the following forula (7a'):

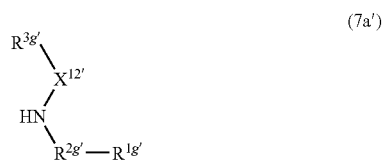

(7a')

wherein $X^{12'}$ is straight chain or branched alkylene having 1 to 5 carbon atoms, $R^{1g'}$ is phenyl optionally having 1 to 3 substituents selected from the group consisting of straight chain or branched alkyl having 1 to 9 carbon atoms, a halogen atom, cyano, hydroxy and amino; or phenyl substituted by $R^{4g'}$, $R^{2g'}$ is divalent pyridazinyl optionally having 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl and halogenated methyl; or divalent pyridazinyl substituted by $R^{5g'}$, and $R^{3g'}$ is a hydrogen atom; straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, amino, mono-substituted amino, di-substituted amino, alkylsulfanyl and halogenated methyl, or a straight chain or branched alkyl group having 1 to 5 carbon atoms, cycloalkyl having 3 to 7 carbon atoms, phenyl, biphenyl, piperidinyl, piperazinyl, imidazolyl, benzimidazolonyl or morpholinyl, each of which is substituted by $R^{6g'}$, provided that any one of $R^{3g'}$, $R^{4g'}$, $R^{5g'}$ and $R^{6g'}$ is optionally a group selected from the group consisting of the formulas (7B) to (7D):

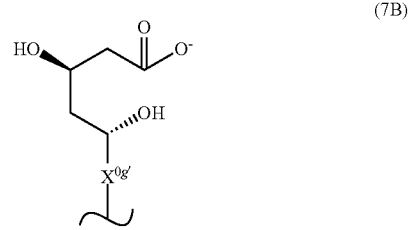

(7B)

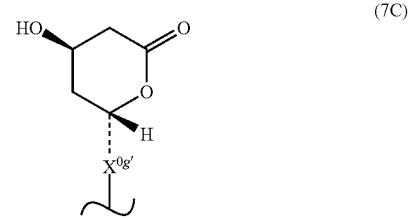

(7C)

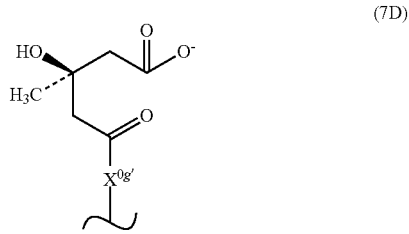

(7D)

wherein $X^{0g'}$ is straight chain or branched alkylene having 1 to 5 carbon atoms;

a compound selected from the group consisting of the following formulas (8a') to (8j'):

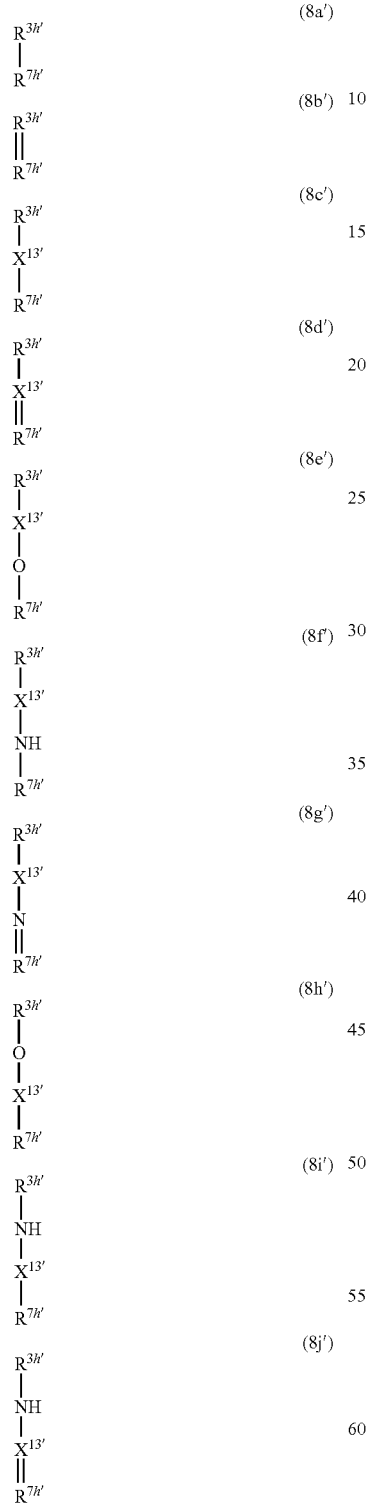

wherein $X^{13'}$ is straight chain or branched alkylene having 1 to 5 carbon atoms, $R^{3h'}$ is a hydrogen atom; straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms and optionally having hydroxy, a halogen atom, cyano, hydroxy, methoxy, amino, mono-substituted amino, di-substituted amino, alkylsulfanyl and halogenated methyl; or a straight chain or branched alkyl group having 1 to 5 carbon atoms, cycloalkyl having 3 to 7 carbon atoms, phenyl, biphenyl, piperidinyl, piperazinyl, imidazolyl, benzimidazolonyl or morpholinyl, each of which is substituted by $R^{6h'}$, and $R^{7h'}$ is a hydrogen atom; phenothiazinyl, phenazinyl, dihydrophenazinyl, thioxanthenyl, dibenzoxazepinyl, phenoxazinyl, acrydinyl, xanthenyl, thianthrenyl or phenoxathiinyl, each of which optionally has 1 to 3 substituents selected from the group consisting of a straight chain or branched alkyl group having 1 to 9 carbon atoms, a halogen atom, cyano, hydroxy, amino, mono-substituted amino, di-substituted amino, substituted imino, alkylsulfanyl and halogenated methyl; or a straight chain or branched alkyl group having 1 to 5 carbon atoms, phenothiazinyl having 3 to 7 carbon atoms, phenazinyl, dihydrophenazinyl, thioxanthenyl, dibenzoxazepinyl, phenoxazinyl, acrydinyl, xanthenyl, thianthrenyl or phenoxathiinyl, each of which is substituted by $R^{5h'}$, provided that any one of $R^{3h'}$, $R^{5h'}$ and $R^{6h'}$ is optionally a group selected from the group consisting of the formulas (8B) to (8D):

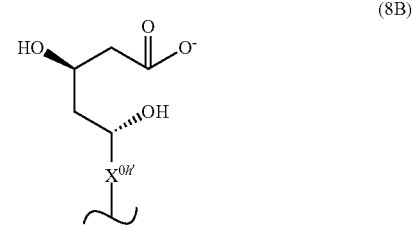

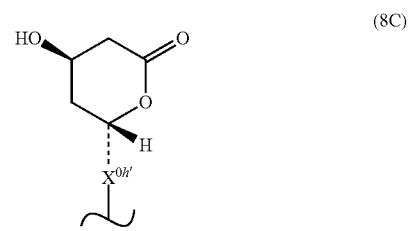

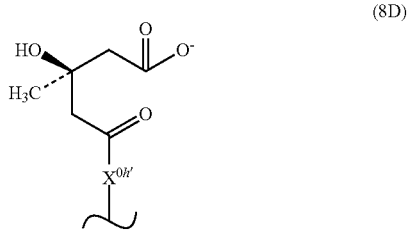

wherein $X^{0h'}$ is straight chain or branched alkylene having 1 to 5 carbon atoms;

a compound represented by the formula (9'):

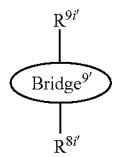

wherein

Bridge$^{9'}$ is a bridge structure selected from the group consisting of the formulas (9a') and (9b'):

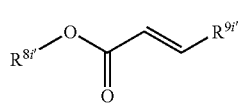

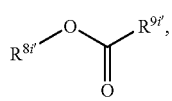

$R^{8i'}$ is a group represented by the formula (i1'):

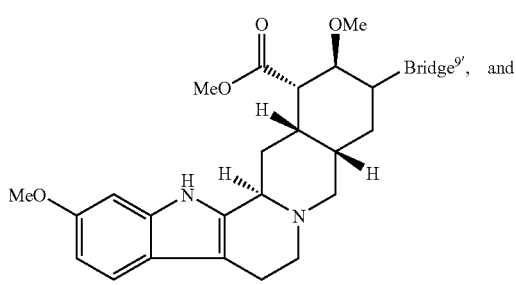

$R^{9i'}$ is a hydrogen atom; straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, alkoxycarbonyloxy, amino, mono-substituted amino, di-substituted amino, alkylsulfanyl and halogenated methyl; or a straight chain or branched alkyl group having 1 to 5 carbon atoms, cycloalkyl having 3 to 7 carbon atoms, phenyl, biphenyl, piperidinyl, piperazinyl, imidazolyl, benzimidazolonyl or morpholinyl, each of which is substituted by $R^{6i'}$, provided that any one of $R^{6i'}$ and $R^{9i'}$ is optionally a group selected from the group consisting of the formulas (9B) to (9D):

wherein $X^{0i'}$ is straight chain or branched alkylene having 1 to 5 carbon atoms;

a compound represented by the formula (10'):

(10')

wherein

Bridge$^{10'}$ is a bridge structure selected from the group consisting of the formulas (10a') and (10b'):

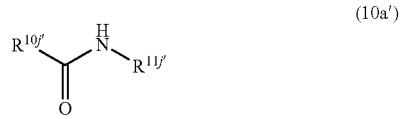

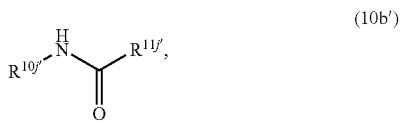

$R^{10j'}$ is a group represented by the formula (j1'):

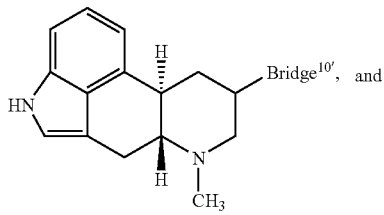

(j1')

$R^{11j'}$ is a group represented by the formula (j2')

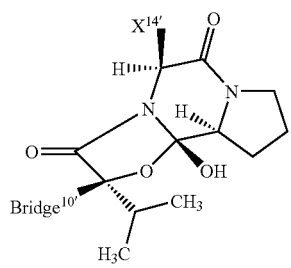

(j2')

wherein $X^{14'}$ is isopropyl, isobutyl, sec-butyl or benzyl; straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, amino, mono-substituted amino, di-substituted amino, alkylsulfanyl and halogenated methyl; or a straight chain or branched alkyl group having 1 to 5 carbon atoms, cycloalkyl having 3 to 7 carbon atoms, phenyl, biphenyl, piperidinyl, piperazinyl, imidazolyl, benzimidazolonyl or morpholinyl, each of which is substituted by $R^{6j'}$, provided that any one of $R^{6j'}$ and $R^{11j'}$ is optionally a group selected from the group consisting of the formulas (10B) to (10D):

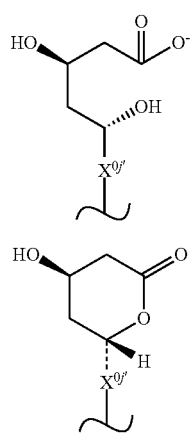

(10B)

(10C)

(10D)

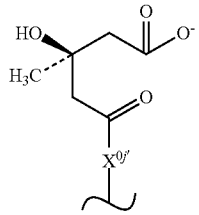

wherein $X^{0j'}$ is straight chain or branched alkylene having 1 to 5 carbon atoms; and a compound represented by the formula (11'):

(11')

wherein $R^{12k'}$ is a group selected from the group consisting of the formulas (11a') and (11b'):

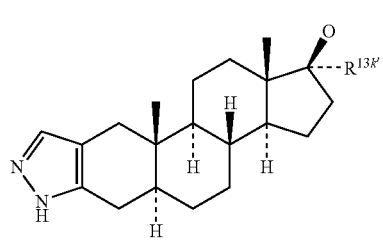

(11a')

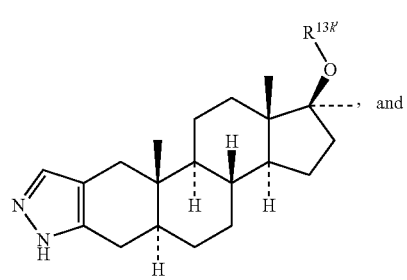

(11b')

and $R^{13k'}$ is a hydrogen atom; straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, amino, mono-substituted amino, di-substituted amino, alkylsulfanyl and halogenated methyl; or a straight chain or branched alkyl group having 1 to 5 carbon atoms, cycloalkyl having 3 to 7 carbon atoms, phenyl, biphenyl, piperidinyl, piperazinyl, imidazolyl, benzimidazolonyl or morpholinyl, each of which is substituted by $R^{6k'}$, provided that any one of $R^{6k'}$ and $R^{13k'}$ is optionally a group selected from the group consisting of the formulas (11B) to (11D):

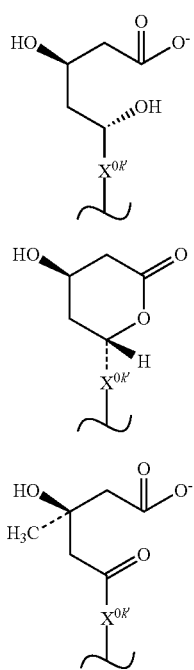

(11B)

(11C)

(11D)

wherein $X^{0k_1}$ is straight chain or branched alkylene having 1 to 5 carbon atoms.

[4] A drug for the treatment or prophylaxis of dementia, which comprises a compound selected from the group consisting of the following formulas (1) to (11), or a pharmaceutically acceptable salt thereof, as an active ingredient;

a compound represented by the formula (1):

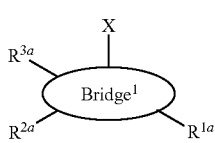

(1)

wherein

Bridge$^1$ is a bridge structure selected from the group consisting of the following formulas (1a) to (1j):

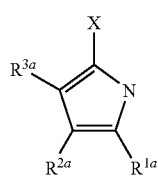

(1a)

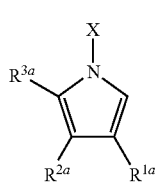

(1b)

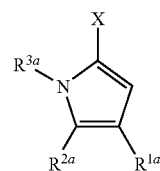

(1c)

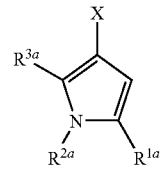

(1d)

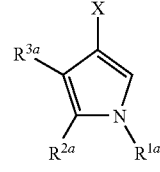

(1e)

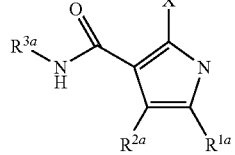

(1f)

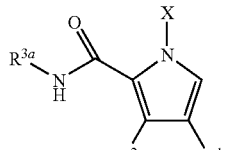

(1g)

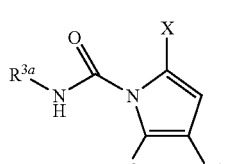

(1h)

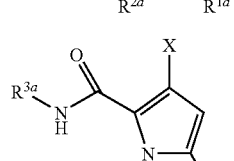

(1i)

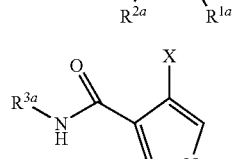

(1j)

$R^{1a}$ is phenyl optionally having 1 to 3 substituents selected from the group consisting of straight chain or branched alkyl having 1 to 9 carbon atoms, a halogen atom, cyano, hydroxy and amino, $R^{2a}$ is straight chain or branched alkyl having 1 to 9 carbon atoms; or phenyl, cycloalkyl having 3 to 7 carbon atoms, phenylalkyl having 7 to 11 carbon atoms, imidazolyl, biphenyl, thienyl, benzothienyl or benzofuryl, each of which optionally has 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl and halogenated methyl, $R^{3a}$ is a hydrogen atom; or straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, amino, mono-substituted amino, di-substituted amino, alkylsulfanyl and halogenated methyl, and X is a hydrogen atom or straight chain or branched alkyl having 1 to 5 carbon atoms;

a compound represented by the formula (2):

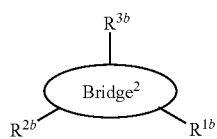

(2)

wherein

Bridge$^2$ is a bridge structure selected from the group consisting of the following formulas (2a) to (2r):

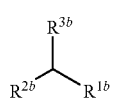

(2a)

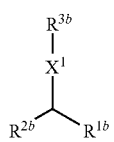

(2b)

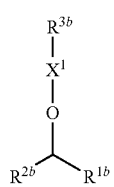

(2c)

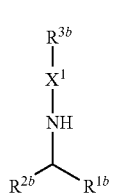

(2d)

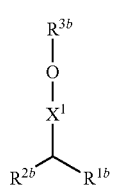

(2e)

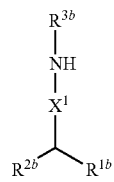

(2f)

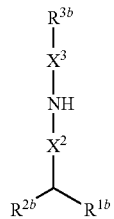

(2g)

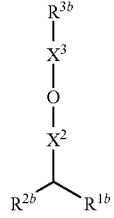

(2h)

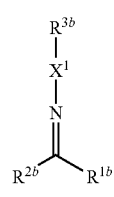

(2i)

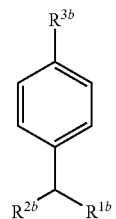

(2j)

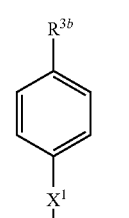

(2k)

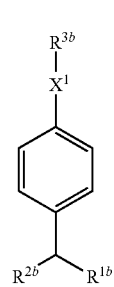

(2l)

(2m) 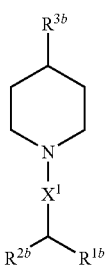

(2n) 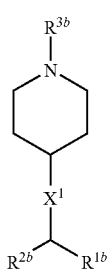

(2o) 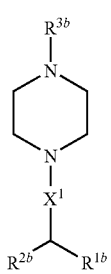

(2p) 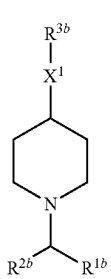

(2q) 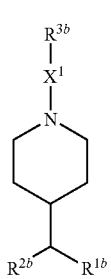

(2r) 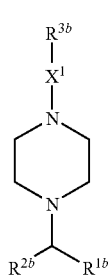

wherein $X^1$ is straight chain or branched alkylene having 1 to 5 carbon atoms, straight chain or branched alkenylene having 2 to 5 carbon atoms or straight chain or branched alkynylene having 2 to 5 carbon atoms, and $X^2$ and $X^3$ are each independently straight chain or branched alkylene having 1 to 3 carbon atoms, straight chain or branched alkenylene having 2 to 3 carbon atoms or alkynylene having 2 to 3 carbon atoms, $R^{1b}$ is phenyl optionally having 1 to 3 substituents selected from the group consisting of straight chain or branched alkyl having 1 to 9 carbon atoms, a halogen atom, cyano, hydroxy and amino, $R^{2b}$ is straight chain or branched alkyl having 1 to 9 carbon atoms; or phenyl, cycloalkyl having 3 to 7 carbon atoms, phenylalkyl having 7 to 11 carbon atoms, imidazolyl, biphenyl, thienyl, benzothienyl or benzofuryl, each of which optionally has 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl and halogenated methyl, and $R^{3b}$ is a hydrogen atom; or straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, amino, mono-substituted amino, di-substituted amino, alkylsulfanyl and halogenated methyl;

a compound represented by the formula (3):

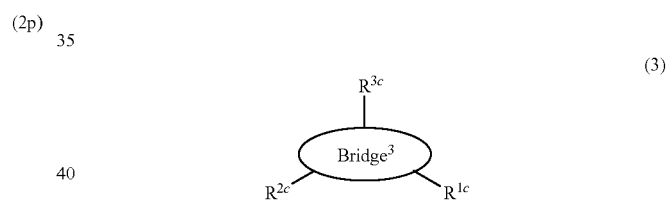

(3)

wherein

Bridge³ is a bridge structure selected from the group consisting of the following formulas (3a) to (3f):

(3a)

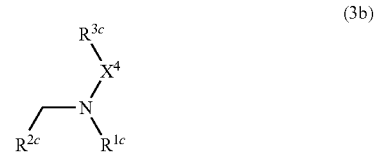

(3b)

(3c)

-continued (3d)
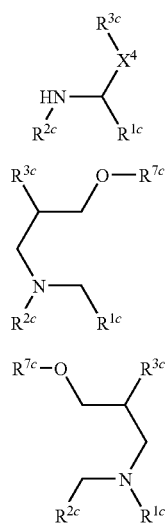

(3e)

(3f)

wherein $X^4$ is straight chain or branched alkylene having 1 to 5 carbon atoms, and $R^{7c}$ is a straight chain or branched alkyl group having 1 to 5 carbon atoms, $R^{1c}$ is phenyl optionally having 1 to 3 substituents selected from the group consisting of straight chain or branched alkyl having 1 to 9 carbon atoms, a halogen atom, cyano, hydroxy and amino, $R^{2c}$ is straight chain or branched alkyl having 1 to 9 carbon atoms; or phenyl, cycloalkyl having 3 to 7 carbon atoms, phenylalkyl having 7 to 11 carbon atoms, imidazolyl, biphenyl, thienyl, benzothienyl or benzofuryl, each of which optionally has 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl and halogenated methyl, and $R^{3c}$ is a hydrogen atom; or straight chain or branched alkyl having 1 to 5 carbon atoms, cycloalkyl having 3 to 7 carbon atoms, phenyl, biphenyl, pyrrolidinyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, amino, mono-substituted amino, di-substituted amino, alkylsulfanyl and halogenated methyl;

a compound represented by the formula (4):

(4)
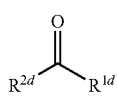

wherein $R^{1d}$ is phenyl optionally having 1 to 3 substituents selected from the group consisting of straight chain or branched alkyl having 1 to 9 carbon atoms, a halogen atom, cyano, hydroxy and amino, $R^{2d}$ is straight chain or branched alkyl having 1 to 9 carbon atoms; or phenyl, cycloalkyl having 3 to 7 carbon atoms, phenylalkyl having 7 to 11 carbon atoms, imidazolyl, biphenyl, thienyl, benzothienyl or benzofuryl, each of which optionally has 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl, halogenated methyl and $R^{5d}$, $R^{4d}$ is a group represented by the formula (d1):

(d1)
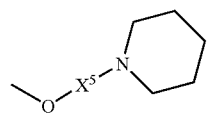

wherein $X^5$ is straight chain or branched alkylene having 1 to 5 carbon atoms, and $R^{5d}$ is 4-hydroxyphenyl;

a compound represented by the formula (5):

(5)
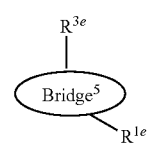

wherein

Bridge$^5$ is a bridge structure represented by the following formula (5a):

(5a)
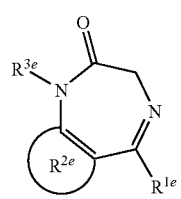

wherein $R^{2e}$ is benzene, cycloalkane having 3 to 7 carbon atoms, imidazole, biphenyl, thiophene, benzothiophene or benzofuran, each of which optionally has 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl and halogenated methyl, $R^{1e}$ is phenyl optionally having 1 to 3 substituents selected from the group consisting of straight chain or branched alkyl having 1 to 9 carbon atoms, a halogen atom, cyano, hydroxy and amino, and $R^{3e}$ is a hydrogen atom; or straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, amino, mono-substituted amino, di-substituted amino, alkylsulfanyl and halogenated methyl;

a compound represented by the formula (6):

 (6)

wherein

Bridge$^6$ is a bridge structure selected from the group consisting of the following formulas (6a) to (6g):

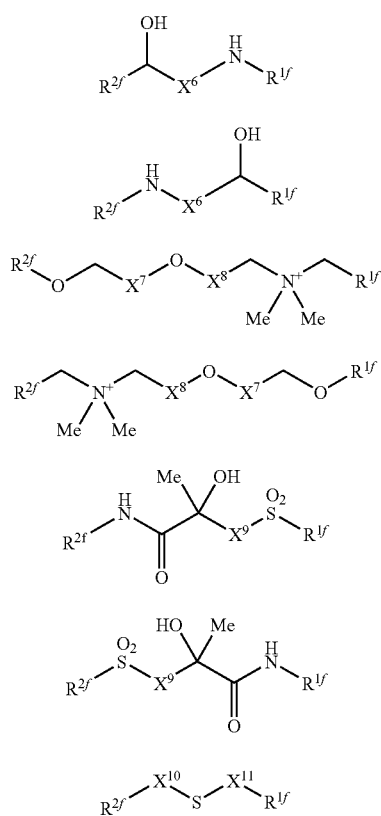

wherein X$^6$ and X$^9$ are each independently straight chain or branched alkylene having 1 to 5 carbon atoms, and X$^7$, X$^8$, X$^{10}$ and X$^{11}$ are each independently straight chain or branched alkylene having 1 to 3 carbon atoms, R$^{1f}$ is phenyl optionally having 1 to 3 substituents selected from the group consisting of straight chain or branched alkyl having 1 to 9 carbon atoms, a halogen atom, cyano, hydroxy and amino, and R$^{2f}$ is straight chain or branched alkyl having 1 to 9 carbon atoms; phenyl, cycloalkyl having 3 to 7 carbon atoms, phenylalkyl having 7 to 11 carbon atoms, imidazolyl, biphenyl, thienyl, benzothienyl or benzofuryl, each of which optionally has 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl and halogenated methyl; or a group represented by the formula (f1):

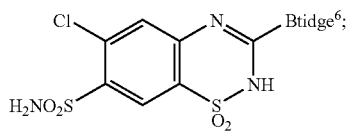 (f1)

a compound represented by the formula (7):

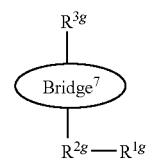 (7)

wherein

Bridge$^7$ is a bridge structure represented by the following formula (7a):

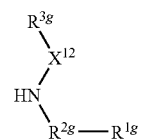 (7a)

wherein X$^{12}$ is straight chain or branched alkylene having 1 to 5 carbon atoms, R$^{1g}$ is phenyl optionally having 1 to 3 substituents selected from the group consisting of straight chain or branched alkyl having 1 to 9 carbon atoms, a halogen atom, cyano, hydroxy and amino, R$^{2g}$ is divalent pyridazinyl optionally having 1 to 3 substituents selected from the group consisting of straight chain or branched alkyl having 1 to 9 carbon atoms, a halogen atom, cyano, hydroxy, amino, mono-substituted amino, di-substituted amino, alkylsulfanyl and halogenated methyl, and R$^{3g}$ is a hydrogen atom; or straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, amino, mono-substituted amino, di-substituted amino, alkylsulfanyl and halogenated methyl;

a compound selected from the group consisting of represented by the following formulas (8a) to (8j):

 (8a)

 (8b)

(8c)
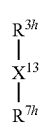

(8d)
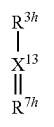

(8e)

(8f)

(8g)
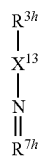

(8h)
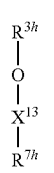

(8i)

(8j)

wherein
$X^{13}$ is straight chain or branched alkylene having 1 to 5 carbon atoms,
$R^{3h}$ is a hydrogen atom; or straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms and optionally having hydroxy, a halogen atom, cyano, hydroxy, methoxy, amino, mono-substituted amino, di-substituted amino, alkylsulfanyl and halogenated methyl, and
$R^{7h}$ is a hydrogen atom; or phenothiazinyl, phenazinyl, dihydrophenazinyl, thioxanthenyl, dibenzoxazepinyl, phenoxazinyl, acrydinyl, xanthenyl, thianthrenyl or phenoxathiinyl, each of which optionally has 1 to 3 substituents selected from the group consisting of a straight chain or branched alkyl group having 1 to 9 carbon atoms, a halogen atom, cyano, hydroxy, amino, mono-substituted amino, di-substituted amino, substituted imino, alkylsulfanyl and halogenated methyl;

a compound represented by the formula (9):

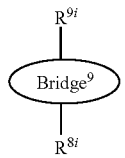

(9)

wherein
Bridge$^9$ is a bridge structure selected from the group consisting of the formulas (9a) to (9b):

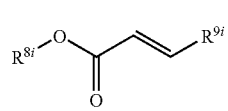

(9a)

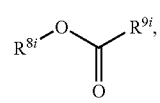

(9b)

$R^{8i}$ is a group represented by the formula (i1):

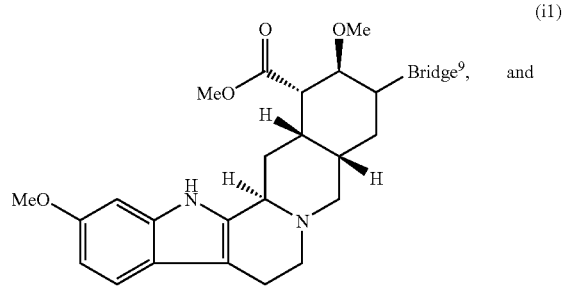

(i1)

and $R^{9i}$ is a hydrogen atom; or straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, alkoxycarbonyloxy, amino, mono-substituted amino, di-substituted amino, alkylsulfanyl and halogenated methyl;

a compound represented by the formula (10):

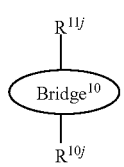
(10)

wherein

Bridge$^{10}$ is a bridge structure selected from the group consisting of the formulas (10a) and (10b):

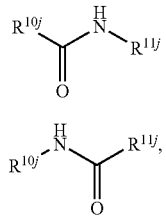
(10a)

(10b)

$R^{10j}$ is a group represented by the formula (j1):

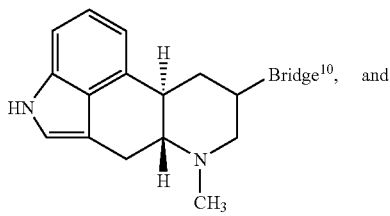
(j1)

$R^{11j}$ is a group represented by the formula (j2)

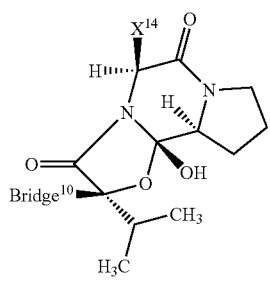
(j2)

wherein $X^{14}$ is isopropyl, isobutyl, sec-butyl or benzyl; or straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, amino, mono-substituted amino, di-substituted amino, alkylsulfanyl and halogenated methyl; and a compound represented by the formula (11):

(11)

wherein
$R^{12k}$ is a group selected from the group consisting of the formulas (11a) and (11b):

(11a)

(11b)

$R^{13k}$ is a hydrogen atom; or straight chain or branched alkyl having 1 to 5 carbon atoms, cycloalkyl having 3 to 7 carbon atoms, phenyl, biphenyl, piperidinyl, piperazinyl, imidazolyl, benzimidazolonyl or morpholinyl, each of which optionally has 1 to 3 substituents selected from the group consisting of a straight chain or branched alkyl group having 1 to 9 carbon atoms, a halogen atom, cyano, hydroxy, methoxy, amino, mono-substituted amino, di-substituted amino, alkylsulfanyl and halogenated methyl.

[5] A method for screening a drug, which comprises evaluating whether or not a test substance is capable of regulating the expression or function of an NCS protein gene.

[6] The method according to the aforementioned [5], wherein the drug is an agent of regulating central nervous action, dementia action or Alzheimer's disease action.

[7] The method according to the aforementioned [5], wherein the drug is a substance capable of regulating an action associated with an NCS protein-targeting drug.

[8] The method according to the aforementioned [5], wherein the NCS protein gene is a neurocalcin gene.

[9] The method according to the aforementioned [5], wherein the NCS protein gene is a neurocalcin 5 gene.

[10] The method according to the aforementioned [5], which comprises the following steps (a) to (c):

(a) a step for bringing the test substance into contact with the NCS protein or mutant protein thereof;

(b) a step for measuring the functional level of the protein or mutant protein thereof in the presence of the test substance, and comparing said functional level with the functional level of the protein or mutant protein thereof in the absence of the test substance;

(c) a step for selecting a test substance that alters the functional level of the protein or mutant protein thereof on the basis of the result of the comparison in (b) above.

[11] The method according to the aforementioned [5], which comprises the following steps (a) to (c):
(a) a step for bringing the test substance into contact with cells enabling a measurement of the expression of the NCS protein or a gene encoding the protein;
(b) a step for measuring the expression level of the NCS protein or the gene in the cells in contact with the test substance, and comparing said expression level with the expression level of the protein or the gene in control cells not in contact with the test substance;
(c) a step for selecting a test substance that regulates the expression level of the protein or the gene on the basis of the result of the comparison in step (b) above.

[12] The method according to the aforementioned [5], which comprises the following steps (a) to (c):
(a) a step for bringing the test substance into contact with an NCS protein or a mutant protein thereof;
(b) a step for measuring the ability of the test substance to bind to said protein;
(c) a step for selecting a test substance that has the binding ability to said protein, on the basis of the result of step (b) above.

[13] The method according to the aforementioned [5], which comprises the following steps (a) to (c):
(a) a step for bringing the test substance and an NCS protein-binding substance into contact with an NCS protein or a mutant protein thereof;
(b) a step for measuring the binding amount of the NCS protein-binding substance to said protein in the presence of the test substance, and comparing said amount with the binding amount of the NCS protein-binding substance to said protein in the absence of the test substance;
(c) a step for selecting a test substance that alters the binding amount of the NCS protein-binding substance to said protein on the basis of the result of the comparison in step (b) above.

[14] The method according to the aforementioned [13], wherein the NCS protein-binding substance is atorvastatin, pimozide, bifonazole, flunarizine, fendiline, chloperastine, bepridil, raloxifene hydrochloride, benzbromarone, prazepam, clotiazepam, suloctidil, benzethonium, bicaltamide, benzthiazide, minaprine, trifluoperazine, chlorprothixene, pimethixene, flupentixol, clofazimine, loxapine, rescinnamine, syrosingopine, dihydroergocornine mesylate, dihydro-α-ergocryptine mesylate, dihydro-β-ergocryptine mesylate, dihydroergocristine mesylate or stanozolol, or a derivative thereof.

[15] A method for screening a substance capable of regulating a function associated with an NCS protein gene, which comprises determining whether or not a test substance is capable of regulating the ability of an NCS protein-targeting drug to bind to NCS or a mutant protein thereof.

[16] The method according to the aforementioned [15], wherein the NCS protein-targeting drug is atorvastatin, pimozide, bifonazole, flunarizine, fendiline, chloperastine, bepridil, raloxifene hydrochloride, benzbromarone, prazepam, clotiazepam, suloctidil, benzethonium, bicaltamide, benzthiazide, minaprine, trifluoperazine, chlorprothixene, pimethixene, flupentixol, clofazimine, loxapine, rescinnamine, syrosingopine, dihydroergocornine mesylate, dihydro-α-ergocryptine mesylate, dihydro-β-ergocryptine mesylate, dihydroergocristine mesylate or stanozolol, or a derivative thereof having the ability to bind to NCS.

[17] The method according to the aforementioned [15], which comprises the following steps (a) to (c):
(a) a step for bringing the test substance and the NCS protein-targeting drug into contact with the NCS or the mutant protein thereof;
(b) a step for measuring the binding amount of the NCS protein-targeting drug to said protein in the presence of the test substance, and comparing said binding amount with the binding amount of the NCS target drug to said protein in the absence of the test substance;
(c) a step for selecting a test substance that alters the binding amount of the NCS protein-targeting drug to said protein on the basis of the result of the comparison in step (b) above.

[18] A substance obtained by the method according to any of the aforementioned [5]-[17].

[19] An agent of regulating a pharmacologic action, comprising a substance obtained by the method according to any of the aforementioned [5]-[17].

[20] An agent of regulating a pharmacologic action, which comprises a substance that regulates the expression or function of an NCS protein gene.

[21] The agent according to the aforementioned [20], wherein the pharmacologic action is an anti-central nervous disease action, an anti-dementia action or an anti-Alzheimer's disease action.

[22] The agent according to the aforementioned [20], which is an agent of regulating an action associated with an NCS protein-targeting drug.

[23] The agent according to the aforementioned [20], wherein the NCS protein gene is a neurocalcin gene.

[24] The agent according to the aforementioned [20], wherein the NCS protein gene is a neurocalcin 5 gene.

[25] The agent according to the aforementioned [20], wherein the substance that regulates the expression or function of the NCS protein gene is a substance that suppresses the expression or function of the NCS protein gene, which is either (i) or (ii):
(i) a nucleic acid selected from a group consisting of NCS antisense nucleic acid, NCS ribozyme, NCS decoy nucleic acid, NCS siRNA, nucleic acid which encodes an NCS antibody, and nucleic acid which encodes an NCS dominant negative mutant protein, or an expression vector that comprises said nucleic acid; or
(ii) a protein selected from a group consisting of NCS antibody, and NCS dominant negative mutant protein.

[26] An agent of regulating a pharmacologic action, comprising an NCS protein, or an expression vector comprising a nucleic acid which encodes the NCS protein.

[27] An agent of regulating a function associated with an NCS protein gene, comprising an NCS protein-targeting drug.

[28] The agent according to the aforementioned [27], wherein the NCS protein-targeting drug is atorvastatin, pimozide, bifonazole, flunarizine, fendiline, chloperastine, bepridil, raloxifene hydrochloride, benzbromarone, prazepam, clotiazepam, suloctidil, benzethonium, bicaltamide, benzthiazide, minaprine, trifluoperazine, chlorprothixene, pimethixene, flupentixol, clofazimine, loxapine, rescinnamine, syrosingopine, dihydroergocornine mesylate, dihydro-α-ergocryptine mesylate, dihydro-β-ergocryptine mesylate, dihydroergocristine mesylate or stanozolol, or a derivative thereof having the binding ability to NCS.

[29] A method of producing a derivative of a drug, which comprises derivatizing the drug so as to be able to regulate the function of an NCS protein gene.

[30] The method according to the aforementioned [29], wherein the drug is a statin which has an anti-central nervous disease action, an anti-dementia action or an anti-Alzheimer's disease action.

[31] The method according to the aforementioned [29], wherein the drug is atorvastatin, pimozide, bifonazole, flunarizine, fendiline, chloperastine, bepridil, raloxifene hydrochloride, benzbromarone, prazepam, clotiazepam, suloctidil, benzethonium, bicaltamide, benzthiazide, minaprine, trifluoperazine, chlorprothixene, pimethixene, flupentixol, clofazimine, loxapine, rescinnamine, syrosingopine, dihydroergocornine mesylate, dihydro-α-ergocryptine mesylate, dihydro-β-ergocryptine mesylate, dihydroergocristine mesylate or stanozolol.

[32] The method according to the aforementioned [29], wherein the NCS protein gene is a neurocalcin gene.

[33] The method according to the aforementioned [29], wherein the NCS protein gene is a neurocalcin δ gene.

[34] A method of producing a derivative of a substance capable of regulating a function associated with an NCS protein gene, which comprises derivatizing a drug so as to be able to regulate the ability to bind to NCS or a mutant protein thereof.

[35] The method according to the aforementioned [34], wherein the drug is atorvastatin, pimozide, bifonazole, flunarizine, fendiline, chloperastine, bepridil, raloxifene hydrochloride, benzbromarone, prazepam, clotiazepam, suloctidil, benzethonium, bicaltamide, benzthiazide, minaprine, trifluoperazine, chlorprothixene, pimethixene, flupentixol, clofazimine, loxapine, rescinnamine, syrosingopine, dihydroergocornine mesylate, dihydro-α-ergocryptine mesylate, dihydro-β-ergocryptine mesylate, dihydroergocristine mesylate or stanozolol, or a derivative thereof having the ability to bind to NCS.

[36] A substance obtained by the method according to any of the aforementioned [29]-[35].

[37] An agent of regulating a pharmacologic action, which comprises a substance obtained by the method according to any of the aforementioned [29]-[35].

[38] A complex, which comprises a drug, and NCS or a mutant protein thereof.

[39] A method of producing a complex that comprises a drug and NCS or a mutant protein thereof, which comprises bringing the drug into contact with the NCS or the mutant protein.

[40] A kit, which comprises the following (i) and (ii):
(i) a drug or a salt thereof;
(ii) an NCS protein or a mutant protein thereof, nucleic acid that encodes said protein, expression vector comprising said nucleic acid or cells that enable a measurement of the expression of the NCS protein gene.

BEST MODE FOR CARRYING OUT THE INVENTION

1. NCS Protein and Gene Thereof

Figure 1:
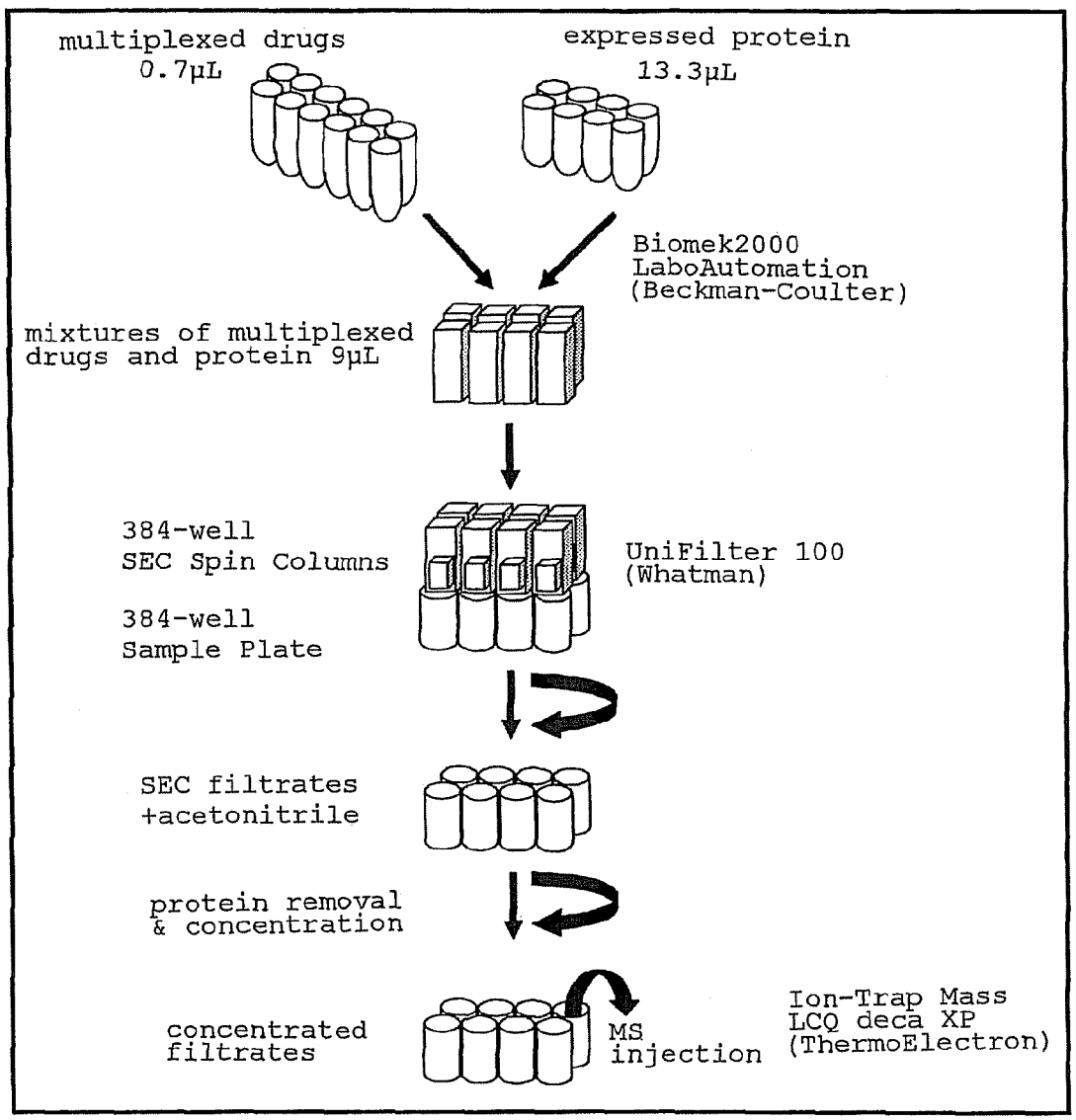
FIG. 1 is a schematic diagram showing a SEC interaction screening system using a spin column.

The present invention provides NCS protein and gene.

The NCS protein is a generic term for calcium ion-binding protein which is specifically expressed in retinal photoreceptor, nerve cell, neural endocrine cell and the like, and which has EF hand motif. The NCS protein also has a myristoylation site at its N-terminus. If the NCS protein bind with $Ca^{2+}$, the localization of the protein to cell membrane is increased by the exposure of myristoyl group arising from conformational change (see, Biochem. J. 353, 1-12 (2001)).

The examples of the NCS protein include proteins belonging to Frequenin family such as NCS-1 (Class A), proteins belonging to VILIPS family such as neurocalcin α, neurocalcin δ, hypocalcin (Class B), proteins belonging to Recoverin family such as Recoverin (Class C), proteins belonging to GCAPs family such as GCAP1, GCAP2, or GCAP3 (Class D), proteins belonging to KChIPs family such as KChIP1, KChIP2 or KChIP3 (Class E), and the like. The protein is preferably a protein belonging to VILIPS family (Class B), and is more preferably neurocalcin δ and human hippocalcin-like protein 1 (or visinin-like protein 3 or VILIP-3). Neurocalcin δ is known to express in nerve cells such as nerve cells in brain including peripheral sensory nerve cells and hippocampus dentate gyrus involved in memory. The human hippocalcin-like protein 1 (or visinin-like protein 3 or VILIP-3) is known to localize in foci of brain tissue of patient with Alzheimer's disease. As mentioned herein, the NCS protein is not limited to human NCS proteins, but includes an orthologue of different animal species. The human neurocalcin δ is a protein derived from FLJ39196 clone described in the Example mentioned below. The human hippocalcin-like protein 1 (or visinin-like protein 3 or VILIP-3) is a protein derived from FLJ20589 clone described in the Example mentioned below.

The NCS protein of the present invention can be, for example, a protein having an amino acid sequence shown by SEQ ID NO:2 or SEQ ID NO:4 (VILIP-3). Human NCS protein is registered as FLJ number (registration number in NEDO (New Energy and Industrial Technology Development organization) protein cDNA structural analysis project): FLJ39196, GenBank accession number: AK096515, and H-Inv cDNA ID: HIT000021370 and H-Inv locus ID: HIX0007693 in H-Invitational database (H-Inv DB), as well as FLJ number: FLJ20589, GenBank accession number: AK000596, and H-Inv cDNA ID: HIT000003071 and H-Inv locus ID: HIX0001817 (see, Nat. Genet. 36(1), 40-45 (2004)), and was found by the present inventors to interact with the compounds described in the Example, including statin drugs. The NCS protein of the present invention is also registered as OMIM606722 and 600207 in OMIM (Online Mendelian Inheritance in Man™.

According to the present invention, a mutant protein of NCS protein is also provided. The mutant proteins can be, for example, a protein which consists of an amino acid sequence resulting from the substitution, deletion, addition or insertion of one or plural amino acids in the amino acid sequence shown by SEQ ID NO:2 or SEQ ID NO:4 (VILIP-3), and which show an interaction with a drug.

The number of amino acids substituted, deleted, added or inserted can be any one that allows the retention of the function, and it can be, for example about 1 to 30, preferably about 1 to 20, more preferably about 1 to 10, further more preferably about 1 to 5, most preferably 1 or 2. The site for substitution, deletion, addition or insertion of an amino acid can be any site that allows the retention of the function, and it can be, for example, a site of EF hand motif, a myristoylation site and sites other than these sites.

Furthermore, the mutant protein of the present invention can be a protein which consists of an amino acid sequence having a homology of for example about 50% or more, preferably about 70% or more, more preferably about 80% or more, further more preferably about 90% or more, most preferably about 95% or more (but excluding 100% homology), to the amino acid sequence shown by SEQ ID NO:2 or SEQ ID NO:4 (VILIP-3), and which shows an interaction with a drug. Here, the numerical values of the above-described homology are calculated by, for example, executing the commands for the maximum matching method using the DNASIS sequence analytical software (Hitachi Software Engineering). The parameters for the calculation should be used in default settings (initial settings).

The drug with which the protein of the present invention shows an interaction is an NCS protein-targeting drug. The NCS protein-targeting drug refers to a drug which shows a pharmaceutical effect or adverse effect via NCS protein. The examples of the drug include substances capable of regulating an action associated with NCS protein-targeting drug (for example, substances capable of regulating central nervous action), substances capable of regulating a function associated with NCS protein gene, and the like. The drug includes a medicine and reagent. Preferably, the NCS protein-targeting drug can be the compound described below.

When the NCS protein of the present invention or a mutant protein thereof is used, the protein may be labeled or unlabeled. In addition, a mixture comprising a labeled protein and an unlabeled protein in a specified ratio can be used as the protein. The examples of the labeling substance include fluorescent substances such as FITC and FAM, luminescent substances such as luminol, luciferin and lucigenin, radioisotopes such as $^3H$, $^{14}C$, $^{32}P$, $^5S$, and $^{123}I$, affinity substances such as biotin and streptavidin, and the like.

The NCS protein genes of the present invention may be any ones that encode the NCS proteins of the present invention. For example, the NCS protein genes of the present invention can be those corresponding to proteins comprising the above-described amino acid sequences. Preferably, the protein consist of a nucleotide sequence shown by SEQ ID NO:1. The NCS protein genes of the present invention are not limited to human genes described above, but include orthologues of different animal species.

According to the present invention, the gene is also provided, which consists of a nucleotide sequence that hybridizes to a sequence complementary to the nucleotide sequence shown by SEQ ID NO:1 under stringent conditions, and which corresponds to a protein that shows an interaction with a drug. Here, hybridize under stringent conditions means that a positive hybridization signal remains observable even under conditions of, for example, heating in a solution of 6×SSC, 0.5% SDS and 50% formamide at 42° C., followed by washing in a solution of 0.1×SSC and 0.5% SDS at 68° C.

The NCS proteins of the present invention and genes thereof can be used for the development of drugs for diseases associated with NCS protein-targeting drug (for example, central nervous diseases), or diseases associated with the NCS protein gene, or for the development of investigational reagents for the diseases, and the like. Hereinafter, each disease is described in detail.

(I. Disease Associated with NCS Protein-Targeting Drug)

"A disease associated with NCS protein-targeting drug" means a disease for which NCS protein-targeting drug is used or a disease corresponding to an adverse effect of the drug. The disease associated with NCS protein-targeting drug can be ameliorated or exacerbated by an NCS protein-targeting drug. The examples of the disease associated with NCS protein-targeting drug include central nervous disease and other diseases.

"An action associated with NCS protein-targeting drug" means an action of the same kind as, or opposite kind to, a kind of action actually exhibited by an NCS protein-targeting drug (including pharmacological actions and adverse effects) . In other words, the action associated with NCS protein-targeting drug is an action capable of ameliorate or exacerbate "a disease associated with NCS protein-targeting drug". For example, the action associated with NCS protein-targeting drug is central nervous action or anti-central nervous action, if a disease associated with NCS protein-targeting drug is central nervous disease. "An action associated with NCS protein-targeting drug" would be obvious from the description of "diseases associated with NCS protein-targeting drug."

(Central Nervous Disease)

The central nervous disease is not particularly limited, as long as it involves abnormality in central nervous systems, brain and spinal cord. The examples of the central nervous disease include dementia, epilepsy, Parkinson's disease, schizophrenia, anxiety, insomnia, depression, mania and the like. In particular, dementia is preferred. The dementia can be roughly divided into primary degenerative dementia, and secondary dementia such as multiinfarct dementia (also called cerebrovascular dementia), chronic hydrocephalus, encephalitis, brain tumor, neurosyphilis, pulmonary encephalopathy, drug poisoning or alcohol poisoning, however, primary degenerative dementia is preferred. The examples of primary degenerative dementia include senile dementia which mainly develops at 65 years old and above, and presenile dementia which mainly develops at 40-65 years old, such as Alzheimer's disease, Pick disease or Huntington's disease.

(Other Diseases)

One example of the disease associated with NCS protein-targeting drug can be a disease associated with atorvastatin.

A diseases associated with atorvastatin means a disease for which atorvastatin is used or a disease corresponding to an adverse effect of atorvastatin. Atorvastatin is known as an HMG-CoA reductase inhibitor and the like. Known targets for atorvastatin include Minichromosome maintenance protein 7, Minichromosome maintenance protein 6, HMG-CoA reductase, and the like. Examples of the disease for which atorvastatin is used include hypercholesterolemia, familial hypercholesterolemia and the like. In contrast, the examples of the adverse effect of atorvastatin include gastric discomfort, itching, digital tremor, insomnia, diarrhea, heartburn, constipation, headache, general malaise, rhabdomyolysis, myopathy, impairment of liver function, jaundice, hypersensitivity, thrombocytopenia, skin/mucosa/eye syndrome (Stevens-Johnson syndrome), toxic epidermal necrolysis (Lyell syndrome), erythema multiforme, hyperglycemia, diabetes and the like.

Furthermore, the disease associated with NCS protein-targeting drug can be a disease associated with NCS-binding compound. Examples of the NCS-binding compounds include pimozide, bifonazole, fendiline, cloperastine, bepridil, raloxifene hydrochloride, benzbromarone, prazepam, clotiazepam, suloctidil, benzethonium, bicaltamide, benzthiazide, minaprine, trifluoperazine, chlorprothixene, pimethixene, flupentixol cis-(Z), clofazimine, loxapine, rescinnamine, syrosingopine, dihydroergotoxine mesylate, dihydroergocristine, stanozolol, and flunarizine.

A disease associated with pimozide means a disease for which pimozide is used or a disease corresponding to an adverse effect of pimozide. Examples of the disease for which pimozide is used include schizophrenia, abnormal behavior found in movement/emotion/motivation/interpersonal relation and the like associated with autism spectrum disorder or mental retardation in child, pathologic symptom found in sleep/eating/excretion/speech and the like, mental symptom found in stereotypy, and the like. In contrast, examples of the adverse effect of pimozide include extrapyramidal symptom, parkinson's syndrome (tremor, muscle rigidity, salivation, etc.), akathisia (akathisia), dyskinesia (rotatory nystagmus, dysarthria, dysphagia, etc.), insomnia/drowsiness, manifestation of agitation/excitation/hyperkinesis/irritability/hallucination/delusion, hypotension, skin rash/itching, nausea/vomiting, anorexia, abdominal discomfort, constipation, abdominal pain, diarrhea, dysuria, frequent urination, nocturnal enuresis, increased value of prolactin and the like.

A disease associated with bifonazole means a disease for which bifonazole is used or a disease corresponding to an adverse effect of bifonazole. Examples of the disease for which bifonazole is used include cutaneous fungal disease (trichophytosis, candidiasis, tinea versicolor) and the like. In contrast, examples of the adverse effect of bifonazole include local irritate, dermatitis, redness/erythema, crack, scale, itching, erosion and the like.

A disease associated with cloperastine means a disease for which cloperastine is used or a disease corresponding to an adverse effect of cloperastine. Examples of the disease for which cloperastine is used include coughing associated with cold/acute bronchitis/chronic bronchitis/bronchiectasis/pulmonary tuberculosis/lung cancer and the like. In contrast, examples of the adverse effect of cloperastine include drowsiness, nausea, anorexia, dry mouth and the like.

A disease associated with bepridil means a disease for which bepridil is used or a disease corresponding to an adverse effect of bepridil. Examples of the disease for which bepridil is used include tachyarrhythmia, angina and the like. In contrast, examples of the adverse effect of bepridil include QT interval prolongation, bradycardia, ventricular tachycardia, vomiting and the like.

A disease associated with raloxifene hydrochloride means a disease for which raloxifene hydrochloride is used or a disease corresponding to an adverse effect of raloxifene hydrochloride. Examples of the disease for which raloxifene hydrochloride is used include postmenopausal osteoporosis and the like. In contrast, examples of the adverse effect of raloxifene hydrochloride include thrombocytopenia, decreased hemoglobin, decreased hematocrit, decreased calcium in blood, decreased total protein in serum, increase of benign intrauterine fluid and the like.

A disease associated with benzbromarone means a disease for which benzbromarone is used or a disease corresponding to an adverse effect of benzbromarone. Examples of the disease for which benzbromarone is used include hyperuricemia, gout, hypertension with hyperuricemia and the like. In contrast, examples of the adverse effect of benzbromarone include abdominal discomfort, gastrointestinal disorder, itching, skin rash, diarrhea, liver disorder and the like.

A disease associated with prazepam means a disease for which prazepam is used or a disease corresponding to an adverse effect of prazepam. Examples of the disease for which prazepam is used include anxiety/stress/depressive symptom/sleep disorder in neurosis or depression, physical symptom or anxiety/stress/depressive symptom/sleep disorder in psychophysiologic disorder (gastrointestinal disease, hypertension, autonomic dystonia) and the like. In contrast, examples of the adverse effect of prazepam include drowsiness, dizzy, fatigue, malaise, sluggishness, anorexia and the like.

A disease associated with clotiazepam means a disease for which clotiazepam is used or a disease corresponding to an adverse effect of clotiazepam. Examples of the disease for which clotiazepam is used include physical symptom and anxiety/stress/hypochondriasis/depressive symptom/sleep disorder in psychophysiologic disorder (gastrointestinal disease, cardiovascular disease), giddiness/neck stiffness/anorexia in autonomic dystonia, and the like. In contrast, examples of the adverse effect of clotiazepam include drowsiness, dizzy, fatigue, malaise, sluggishness, anorexia and the like.

A disease associated with trifluoperazine means a disease for which trifluoperazine is used or a disease corresponding to an adverse effect of trifluoperazine. Examples of the disease for which trifluoperazine is used include schizophrenia and the like. In contrast, examples of the adverse effect of trifluoperazine include akinetic mutism, severe muscle rigidity, aphagia, tachycardia, variation in blood pressure, sweating, fall in blood pressure, electrocardiogram abnormality and the like.

A disease associated with clofazimine means a disease for which clofazimine is used or a disease corresponding to an adverse effect of clofazimine. Examples of the disease for which clofazimine is used include Hansen's disease and the like. In contrast, examples of the adverse effect of clofazimine include coloring of skin, dry skin, photosensitivity, ichthyosis, skin rash, pruritus, gastrointestinal bleeding, nausea, vomiting, anorexia, giddiness, headache, neuralgia and the like.

A disease associated with rescinnamine means a disease for which rescinnamine is used or a disease corresponding to an adverse effect of rescinnamine. Examples of the disease for which rescinnamine is used include hypertension and the like. In contrast, examples of the adverse effect of rescinnamine include depression and the like.

A disease associated with dihydroergotoxine mesylate means a disease for which dihydroergotoxine mesylate is used or a disease corresponding to an adverse effect of dihydroergotoxine mesylate. Examples of the disease for which dihydroergotoxine mesylate is used include hypertension, peripheral circulatory disturbance (Buerger's disease, arteriosclerosis obliterans, arterial embolism, thrombosis, Raynaud's disease and Raynaud's syndrome, acrocyanosis, chilblain/frostbite, intermittent claudication), metabolic disorder in brain, and the like. In contrast, examples of the adverse effect of dihydroergotoxine mesylate include gastrointestinal disorder, nausea/vomiting, anorexia, skin rash/pruritus, headache, giddiness and the like.

(II. Disease Associated with the NCS Protein Gene)

"A disease associated with the NCS protein gene" refers to a disease that can be caused as a result of a change in the function or expression level of the NCS protein gene, or in the function or expression level of a gene located downstream of the NCS protein gene in the signal transduction system mediated by the NCS protein gene (downstream gene). The change in the function of the NCS protein gene or a gene downstream thereof can be caused by, for example, a mutation (e.g., polymorphism) in the gene. Examples of the mutation include a mutation in the coding region, which promotes or suppresses the function of the gene, a mutation in the non-coding region, which promotes or suppresses the expression thereof, and the like. The change in the expression level includes increases or reductions in the expression level. A disease associated with the NCS protein gene can be ameliorated or exacerbated by NCS protein.

"A function associated with the NCS protein gene" means a function of the same kind as, or opposite kind to, the kind of a function that is actually exhibited by NCS protein. In other words, "a function associated with the NCS protein gene" is a function capable of ameliorating or exacerbating "a disease associated with the NCS protein gene." The examples of the function associated with the NCS protein gene include phototransduction, regulation of release of bioactive substances such as hormone/cytokine and neurotransmitter, control of activity of guanyl cyclase or adenyl cyclase, regulation of metabolism of cyclic nucleotide, regulation of gene expression, control of ion channel, control of G protein-coupled receptors such as acetylcholine receptors and dopamine receptors or other cell membrane surface receptors, control of G protein-coupled receptor kinase, control of proteases such as presenilin 2, regulation of metabolism of inositol phospholipid, and the like.

Furthermore, we performed a BLAST search of the NCS protein of the present invention in SwissProt and RefSeq, and subjected it to further analysis by GO (Gene Ontology) category classification information on the basis of the search results. As a result, the protein was classified into GO:0003779¥MF|actin binding, GO:0005509¥MF|calcium ion binding, GO:0015631¥MF|tubulin binding and GO:0030276¥MF|clathrin binding as MF (molecular function); GO:0016192¥BP|vesicle-mediated transport as BP (biological process); and GO:0005829¥CC|cytosol and GO:0030130¥CC|clathrin coat of trans-Golgi network vesicle as CC (cell component). Therefore, the function associated with the NCS protein gene can include functions derivable from these information on GO category classification, in addition to the functions described above.

Since the NCS protein gene is considered to mediate a wide variety of physiological functions in the body, a very wide variety of diseases are supposed as diseases associated with the NCS protein gene. The examples of the diseases include dementia, epilepsy, Parkinson's disease, schizophrenia, anxiety, insomnia, depression, mania, neurodegeneration, retinal dysplasia, cancer, diabetes, pain (particularly, chronic pain) and the like. Furthermore, other diseases possibly associated with the NCS protein gene include chondrocalcinosis (OMIM600668).

(III. NCS Protein-Targeting Drug)

The (I) to (VIII), the formulas (1) to (11) and the formulas (1') to (11') of the present invention are now explained.

Compounds represented by the formulas (I) to (VIII), the formulas (1) to (11) and the formulas (1') to (11') can be produced by applying various known synthesis methods based on the basic skeleton or the kind of substituent. For example, alkylation, acylation, amination, imination, halogenation, reduction, oxidation, condensation, cyclization and the like can be mentioned, and the reactions and methods generally used in this field can be utilized.

The "halogen atom" is a fluorine atom, a chlorine atom, a bromine atom or an iodine atom.

As the "straight chain or branched alkyl having 1 to 9 carbon atoms", for example, methyl, ethyl, propyl, isopropyl, butyl, isobutyl, sec-butyl, tert-butyl, pentyl, isopentyl, neopentyl, sec-pentyl, tert-pentyl, hexyl, isohexyl, 2-ethylbutyl, heptyl, octyl, 1,1,3,3-tetramethylbutyl, nonyl and the like can be mentioned.

As the "straight chain or branched alkyl having 1 to 7 carbon atoms", for example, methyl, ethyl, propyl, isopropyl, butyl, isobutyl, sec-butyl, tert-butyl, pentyl, isopentyl, neopentyl, sec-pentyl, tert-pentyl, hexyl, isohexyl, 2-ethylbutyl, heptyl and the like can be mentioned.

As the "straight chain or branched alkyl having 1 to 5 carbon atoms", for example, methyl, ethyl, propyl, isopropyl, butyl, isobutyl, sec-butyl, tert-butyl, pentyl, isopentyl, neopentyl, sec-pentyl, tert-pentyl and the like can be mentioned.

The alkyl group is optionally substituted, at any position, by hydroxy, a halogen atom, cyano, methoxy, amino, mono-substituted amino, di-substituted amino, alkylsulfanyl, or halogenated methyl, and to be specific, hydroxymethyl, 1 or 2-hydroxyethyl, 1, 2 or 3-hydroxypropyl and the like can be mentioned.

As the "alkyloxy", straight chain or branched alkyloxy having 1 to 9 carbon atoms, for example, methyloxy, ethyloxy, propyloxy, isopropyloxy, butyloxy, isobutyloxy, sec-butyloxy, tert-butyloxy, pentyloxy, isopentyloxy, neopentyloxy, sec-pentyloxy, tert-pentyloxy, hexyloxy, isohexyloxy, 2-ethylbutyloxy, heptyloxy, octyloxy, 1,1,3,3-tetramethylbutyloxy, nonyloxy and the like can be mentioned.

As the "straight chain or branched alkyloxy having 1 to 5 carbon atoms", for example, methyloxy, ethyloxy, propyloxy, isopropyloxy, butyloxy, isobutyloxy, sec-butyloxy, tert-butyloxy, pentyloxy, isopentyloxy, neopentyloxy, sec-pentyloxy, tert-pentyloxy and the like can be mentioned.

As the "straight chain or branched alkyl having 1 to 7 carbon atoms", for example, methyl, ethyl, propyl, isopropyl, butyl, isobutyl, sec-butyl, tert-butyl, pentyl, isopentyl, neopentyl, sec-pentyl, tert-pentyl, hexyl, isohexyl, 2-ethylbutyl, heptyl and the like can be mentioned.

As the "phenylalkyl having 7 to 12 carbon atoms", for example, benzyl, 1 or 2-phenylethyl, 1, 2 or 3-phenylpropyl, 1, 2, 3 or 4-phenylbutyl and the like can be mentioned.

As the "phenylalkyl having 7 to 11 carbon atoms", for example, benzyl, 1 or 2-phenylethyl or 1, 2 or 3-phenylpropyl and the like can be mentioned.

As the "phenylalkenyl having 8 to 12 carbon atoms", for example, 1 or 2-phenylethenyl (a or β-styryl), 1, 2 or 3-phenyl-1-propenyl, 1, 2 or 3-phenyl-2-propenyl (e.g., cinnamyl etc.), 1, 2, 3 or 4-phenyl-1-butenyl, 1, 2, 3 or 4-phenyl-2-butenyl and the like can be mentioned.

As the "phenylalkyloxy having 7 to 12 carbon atoms", for example, benzyloxy, 1 or 2-phenylethyloxy, 1, 2 or 3-phenylpropyloxy, 1, 2, 3 or 4-phenylbutyloxy and the like can be mentioned.

As the "alkoxycarbonyloxy", for example, methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, tert-butoxycarbonyloxy and the like can be mentioned.

As the "alkylsulfanyl", straight chain or branched alkylsulfanyl having 1 to 9 carbon atoms, for example, methylsulfanyl, ethylsulfanyl, propylsulfanyl, isopropylsulfanyl, butylsulfanyl, isobutylsulfanyl, sec-butylsulfanyl, tert-butylsulfanyl, pentylsulfanyl, isopentylsulfanyl, neopentylsulfanyl, sec-pentylsulfanyl, tert-pentylsulfanyl, hexylsulfanyl, isohexylsulfanyl, 2-ethylbutylsulfanyl, heptylsulfanyl, octylsulfanyl, 1,1,3,3-tetramethylbutylsulfanyl, nonylsulfanyl and the like can be mentioned.

As the "halogenated alkyl", straight chain or branched alkyl having 1 to 9 carbon atoms and substituted by one or more halogen atoms, for example, fluoromethyl, difluoromethyl, trifluoromethyl, chloromethyl, dichloromethyl, trichloromethyl, bromomethyl, iodomethyl, 2-chloroethyl, 2-fluoroethyl, 2,2,2-trifluoroethyl and the like can be mentioned.

As the "halogenated methyl", for example, fluoromethyl, difluoromethyl, trifluoromethyl, chloromethyl, dichloromethyl, trichloromethyl, bromomethyl, iodomethyl and the like can be mentioned.

As the "mono-substituted amino", an amino group mono-substituted by a substituent selected from the group consisting of the above-defined straight chain or branched alkyl having 1 to 9 carbon atoms; a phenyl group optionally having 1 to 3 substituents selected from the group consisting of the above-defined straight chain or branched alkyl having 1 to 9 carbon atoms, a halogen atom, cyano, hydroxy, methoxy, amino, the above-defined alkylsulfanyl and the above-mentioned defined halogenated methyl; and the like can be mentioned. To be specific, N-methylamino, N-ethylamino, N-propylamino, N-isopropylamino, N-butylamino, N-isobutylamino, N-sec-butylamino, N-tert-butylamino, N-pentylamino, N-isopentylamino, N-neopentylamino, N-sec-pentylamino, N-tert-pentylamino, N-hexylamino, N-isohexylamino, N-2-ethylbutylamino, N-heptylamino, N-octylamino, N-(1,1,3,3-tetramethylbutyl)amino, N-nonylamino, N-phenylamino, N-(2, 3 or 4-chlorophenyl)amino, N-(2, 3 or 4-fluorophenyl)amino, N-(2, 3 or 4-methylphenyl)amino, N-(2, 3 or 4-methoxyphenyl)amino, N-(2, 3 or 4-methylsulfanylphenyl)amino, N-(2, 3 or 4-hydroxyphenyl)amino, N-(2, 3 or 4-cyanophenyl)amino, N-(2, 3 or 4-trifluoromethylphenyl)amino and the like can be mentioned.

As the "di-substituted amino", an amino group di-substituted by the same or different substituents selected from the group consisting of the above-defined straight chain or branched alkyl having 1 to 9 carbon atoms; a phenyl group optionally having 1 to 3 substituents selected from the group consisting of the above-defined straight chain or branched alkyl having 1 to 9 carbon atoms, a halogen atom, cyano, hydroxy, methoxy, amino, the above-defined alkylsulfanyl and the above-defined halogenated methyl; and the like can be mentioned. To be specific, N,N-dimethylamino, N,N-diethylamino, N,N-dipropylamino, N,N-diisopropylamino, N,N-dibutylamino, N,N-diisobutylamino, N,N-di-sec-butylamino, N,N-di-tert-butylamino, N,N-dipentylamino, N,N-diisopentylamino, N,N-dineopentylamino, N,N-di-sec-pentylamino, N,N-di-tert-pentylamino, N,N-dihexylamino, N,N-diisohexylamino, N,N-bis(2-ethylbutyl)amino, N,N-diheptylamino, N,N-dioctylamino, N,N-bis(1,1,3,3-tetramethylbutyl)amino, N,N-dinonylamino, N-ethyl-N-methylamino, N-propyl-N-methylamino, N-isopropyl-N-methylamino, N-butyl-N-methylamino, N-isobutyl-N-methylamino, N-sec-butyl-N-methylamino, N-tert-butyl-N-methylamino, N-pentyl-N-methylamino, N-isopentyl-N-methylamino, N-neopentyl-N-methylamino, N-sec-pentyl-N-methylamino, N-tert-pentyl-N-methylamino, N-hexyl-N-methylamino, N-isohexyl-N-methylamino, N-2-ethylbutyl-N-methylamino, N-heptyl-N-methylamino, N-octyl-N-methylamino, N-(1,1,3,3-tetramethylbutyl)-N-methylamino, N-nonyl-N-methylamino, N,N-diphenylamino, N,N-bis(2, 3 or 4-chlorophenyl)amino, N,N-bis(2, 3 or 4-fluorophenyl)amino, N,N-bis(2, 3 or 4-methylphenyl)amino, N,N-bis(2, 3 or 4-methoxyphenyl)amino, N,N-bis(2, 3 or 4-methylsulfanylphenyl)amino, N,N-bis(2, 3 or 4-hydroxyphenyl)amino, N,N-bis(2, 3 or 4-cyanophenyl)amino, N,N-bis(2, 3 or 4-trifluoromethylphenyl)amino, N-phenyl-N-methylamino, N-(2, 3 or 4-chlorophenyl)-N-methylamino, N-(2, 3 or 4-fluorophenyl)-N-methylamino, N-(2, 3 or 4-methylphenyl)-N-methylamino, N-(2, 3 or 4-methoxyphenyl)-N-methylamino, N-(2, 3 or 4-methylsulfanylphenyl)-N-methylamino, N-(2, 3 or 4-hydroxyphenyl)-N-methylamino, N-(2, 3 or 4-cyanophenyl)-N-methylamino, N-(2, 3 or 4-trifluoromethylphenyl)-N-methylamino and the like can be mentioned.

As the "substituted imino", an imino group substituted by a substituent selected from the group consisting of the above-defined straight chain or branched alkyl having 1 to 9 carbon atoms; a phenyl group optionally having 1 to 3 substituents selected from the group consisting of the above-defined straight chain or branched alkyl having 1 to 9 carbon atoms, a halogen atom, cyano, hydroxy, methoxy, amino, the above-defined alkylsulfanyl and the above-defined halogenated methyl; and the like can be mentioned. To be specific, N-methylimino, N-ethylimino, N-propylimino, N-isopropylimino, N-butylimino, N-isobutylimino, N-sec-butylimino, N-tert-butylimino, N-pentylimino, N-isopentylimino, N-neopentylimino, N-sec-pentylimino, N-tert-pentylimino, N-hexylimino, N-isohexylimino, N-2-ethylbutylimino, N-heptylimino, N-octylimino, N-(1,1,3,3-tetramethylbutyl)imino, N-nonylimino, N-phenylimino, N-(2, 3 or 4-chlorophenyl)imino, N-(2, 3 or 4-fluorophenyl)imino, N-(2, 3 or 4-methylphenyl)imino, N-(2, 3 or 4-methoxyphenyl)imino, N-(2, 3 or 4-methylsulfanylphenyl)imino, N-(2, 3 or 4-hydroxyphenyl)imino, N-(2, 3 or 4-cyanophenyl)imino, N-(2, 3 or 4-trifluoromethylphenyl)imino and the like can be mentioned.

As the "cycloalkyl having 3 to 7 carbon atoms", for example, cyclopropanecyclopropyl, cyclobutyl, cyclopentyl, cyclohexyl and cycloheptyl can be mentioned.

As the "phenylalkyl having 7 to 11 carbon atoms", for example, phenylmethyl, 1 or 2-phenylethyl, 1, 2 or 3-phenylpropyl, 1, 2, 3 or 4-phenylbutyl, 1, 2, 3, 4 or 5-phenylpentyl and the like can be mentioned.

As the "imidazolyl", imidazol-1-yl, imidazol-2-yl, imidazol-4-yl and imidazol-5-yl can be mentioned.

As the "biphenyl", 2-biphenyl, 3-biphenyl and 4-biphenyl can be mentioned.

As the "thienyl", 2-thienyl and 3-thienyl can be mentioned.

As the "benzothienyl", 2-benzo[b]thienyl, 3-benzo[b]thienyl, 4-benzo[b]thienyl, 5-benzo[b]thienyl, 6-benzo[b]thienyl, 7-benzo[b]thienyl, 1-benzo[c]thienyl, 3-benzo[c]thienyl, 4-benzo[c]thienyl, 5-benzo[c]thienyl, 6-benzo[c]thienyl and 7-benzo[c]thienyl can be mentioned.

As the "benzofuryl", 2-benzo[b]furyl, 3-benzo[b]furyl, 4-benzo[b]furyl, 5-benzo[b]furyl, 6-benzo[b]furyl, 7-benzo[b]furyl, 1-benzo[c]furyl, 3-benzo[c]furyl, 4-benzo[c]furyl, 5-benzo[c]furyl, 6-benzo[c]furyl and 7-benzo[c]furyl can be mentioned.

As the "piperidinyl", 1-piperidinyl, 2-piperidinyl, 3-piperidinyl and 4-piperidinyl can be mentioned.

As the "pyrrolidinyl", 1-pyrrolidinyl, 2-pyrrolidinyl and 3-pyrrolidinyl can be mentioned.

As the "piperazinyl", 1-piperazinyl and 2-piperazinyl can be mentioned.

As the "benzimidazolonyl", benzimidazol-2-on-1-yl, benzimidazol-2-on-4-yl and benzimidazol-2-on-5-yl can be mentioned.

As the "morpholinyl", morpholin-1-yl, morpholin-2-yl and morpholin-3-yl can be mentioned.

As the "phenothiazinyl", phenothiazin-10-yl, phenothiazin-1-yl, phenothiazin-2-yl, phenothiazin-3-yl and phenothiazin-4-yl can be mentioned.

As the "phenazinyl", phenazinyl-1-yl and phenazinyl-2-yl can be mentioned.

As the "dihydrophenazinyl", 2,10-dihydrophenazinyl-10-yl, 2,10-dihydrophenazinyl-10-ylidene and the like can be mentioned.

As the "thioxanthenyl", thioxanthen-9-yl, thioxanthen-1-yl, thioxanthen-2-yl, thioxanthen-3-yl, thioxanthen-4-yl, thioxanthen-9-ylidene and the like can be mentioned.

As the "dibenzoxazepinyl", dibenzo[b,f][1,4]oxazepin-11-yl and the like can be mentioned.

As the "phenoxazinyl", phenoxazin-10-yl, phenoxazin-1-yl, phenoxazin-2-yl, phenoxazin-3-yl and phenoxazin-4-yl can be mentioned.

As the "acrydinyl", acridin-9-yl, acridin-1-yl, acridin-2-yl, acridin-3-yl and acridin-4-yl can be mentioned.

As the "xanthenyl", xanthen-9-yl, xanthen-1-yl, xanthen-2-yl, xanthen-3-yl, xanthen-4-yl, xanthen-9-ylidene and the like can be mentioned.

As the "thianthrenyl", thianthren-1-yl, thianthren-2-yl, thianthren-3-yl and thianthren-4-yl can be mentioned.

As the "phenoxathiinyl", phenoxathiin-1-yl, phenoxathiin-2-yl, phenoxathiin-3-yl and phenoxathiin-4-yl can be mentioned.

As the "divalent pyridazinyl", pyridazine-3,6-diyl, pyridazine-3,4-diyl, pyridazine-3,5-diyl and pyridazine-3,4-diyl can be mentioned.

As the "straight chain or branched alkylene having 2 to 6 carbon atoms", for example, ethylene, methylmethylene, trimethylene, methylethylene, ethylmethylene, tetramethylene, 1-methyltrimethylene, 2-methyltrimethylene, ethylethylene, propylmethylene, isopropylmethylene, pentamethylene, hexamethylene and the like can be mentioned.

As the "straight chain or branched alkylene having 1 to 5 carbon atoms", for example, methylene, ethylene, methylmethylene, trimethylene, methylethylene, ethylmethylene, tetramethylene, 1-methyltrimethylene, 2-methyltrimethylene, ethylethylene, propylmethylene, isopropylmethylene, pentamethylene and the like can be mentioned.

As the "straight chain or branched alkenylene having 2 to 5 carbon atoms", for example, —CH=CH—, —CH=CH—CH$_2$—, —C(CH$_3$)=CH—, —CH=CH—CH$_2$—CH$_2$—, —CH$_2$—CH=CH—CH$_2$—, —C(CH$_3$)=CH—CH$_2$—, —CH=C(CH$_3$)—CH$_2$—, —CH=CH—CH(CH$_3$)—, —C(Et)=CH—, —CH=CH—CH$_2$—CH$_2$—CH$_2$—, —CH$_2$—CH=CH—CH$_2$—CH$_2$—, —CH=CH—CH=CH—, —CH=CH—CH=CH—CH$_2$— and the like can be mentioned.

As the "straight chain or branched alkynylene having 2 to 5 carbon atoms", for example, —C≡C—, —C≡C—CH$_2$—, —C≡C—CH$_2$—CH$_2$—, —CH$_2$—C≡C—CH$_2$—, —C≡C—CH(CH$_3$)—, —C≡C—CH$_2$—CH$_2$-CH$_2$—, —CH$_2$—C≡C—CH$_2$—CH$_2$—, —C≡C—CH(CH$_3$)—CH$_2$—, —C≡C—CH$_2$—CH(CH$_3$)—, —C≡C—CH(Et)— and the like can be mentioned.

As the "straight chain or branched alkylene having 1 to 3 carbon atoms", for example, methylene, ethylene, methylmethylene, trimethylene, methylethylene and ethylmethylene can be mentioned.

As the "straight chain or branched alkenylene having 2 to 3 carbon atoms", for example, —CH=CH—, —CH=CH—CH$_2$— and —C(CH$_3$)=CH— can be mentioned.

As the "alkynylene having 2 to 3 carbon atoms", for example, —C≡C— and —C≡C—CH$_2$— can be mentioned.

In the formulas (1) to (VIII), each of R$^2$ and R$^4$ bonded to each other, R$^3$ and R$^6$ bonded to each other, R$^6$ and R$^7$ bonded to each other, and R$^7$ and R$^8$ bonded to each other may independently forms a ring optionally having 1 to 3 substituents selected from the group consisting of a halogen atom; cyano; hydroxy; amino; mono-substituted amino; di-substituted amino; halogenated alkyl; alkylsulfanyl; benzimidazolonyl; and straight chain or branched alkyl having 1 to 5 carbon atoms or straight chain or branched alkyloxy having 1 to 5 carbon atoms, each of which optionally has 1 to 3 substituents selected from the group consisting of a halogen atom, cyano, hydroxy, amino, mono-substituted amino, di-substituted amino, alkyloxy and alkylsulfanyl.

As preferable compounds wherein R$^2$ and R$^4$, R$^3$ and R$^6$, R$^6$ and R$^7$, and/or R$^7$ and R$^8$ form a ring, the following compounds can be mentioned.

Compounds wherein R$^7$ and R$^8$ are bonded to each other to form a ring, which are represented by the following formulas (Ia) to (VIIIa):

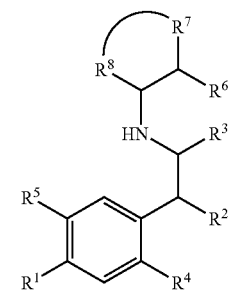

(Ia)

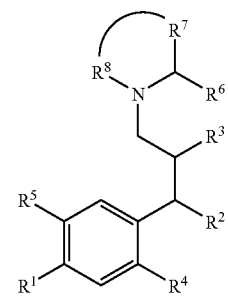

(IIa)

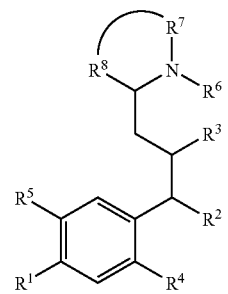

(IIIa)

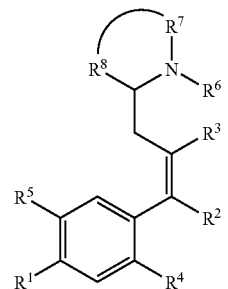

(IVa)

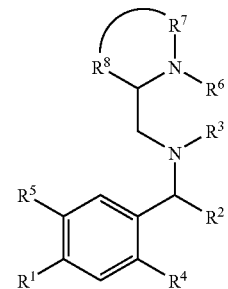

(Va)

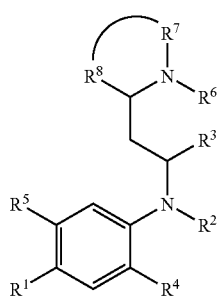
(VIa)
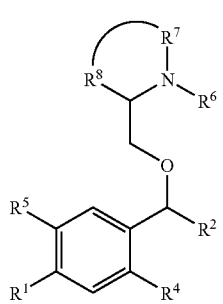
(VIIa)
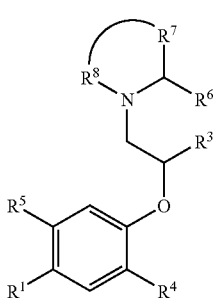
(VIIIa)
wherein each symbol is as defined above;
compounds wherein $R^6$ and $R^7$ are bonded to each other to form a ring, which are represented by the following formulas (Ib) to (VIIIb):
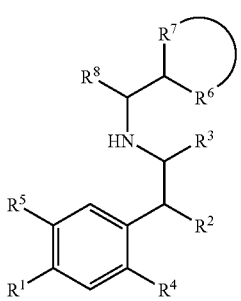
(Ib)
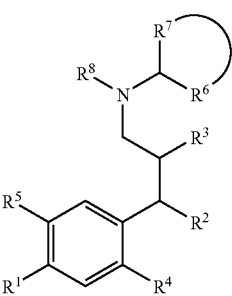
(IIb)
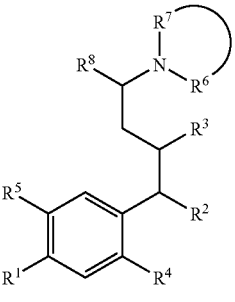
(IIIb)
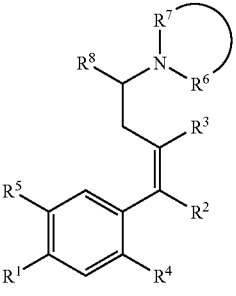
(IVb)
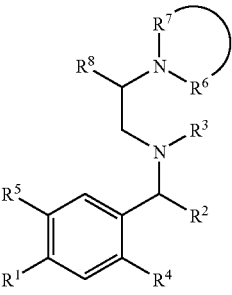
(Vb)
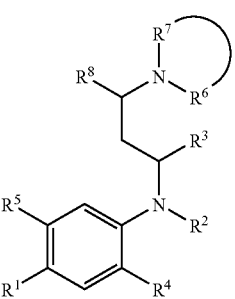
(VIb)

-continued

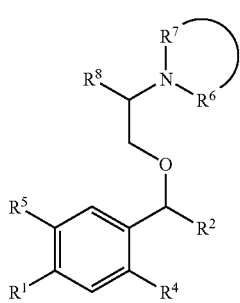
(VIIb)

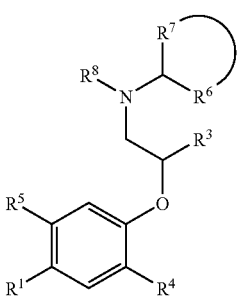
(VIIIb)

wherein each symbol is as defined above;

compounds wherein R² and R⁴ are bonded to each other to form a ring, which are represented by the following formulas (Ic) to (VIIc):

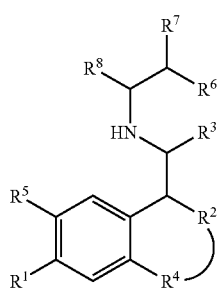
(Ic)

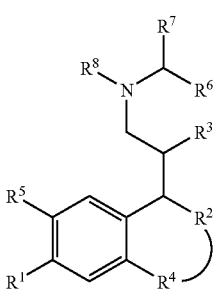
(IIc)

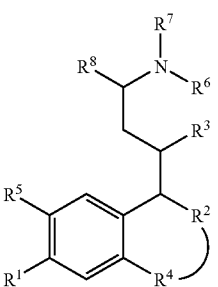
(IIIc)

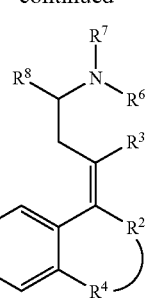
(IVc)

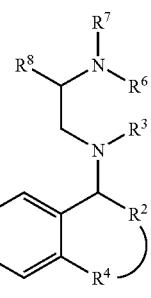
(Vc)

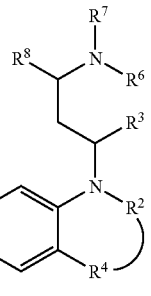
(VIc)

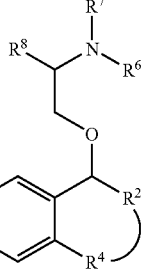
(VIIc)

wherein each symbol is as defined above;

compounds wherein R² and R⁴ are bonded to each other to form a ring, and R⁶ and R⁷ are bonded to each other to form a ring, which are represented by the following formulas (Id) to (VIId):

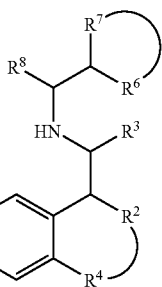
(Id)

(IId)
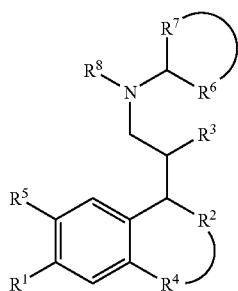
(IIId)
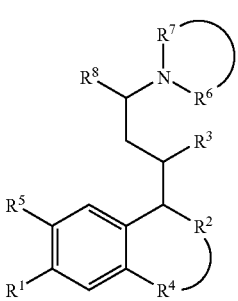
(IVd)
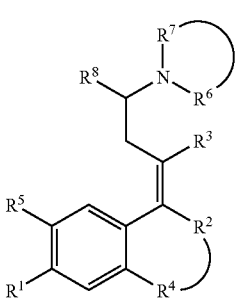
(Vd)
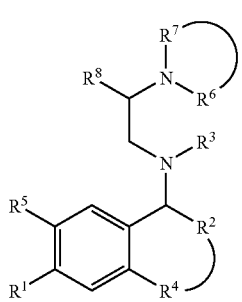
(VId)
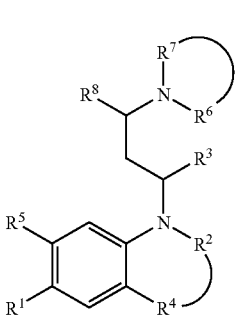
(VIId)
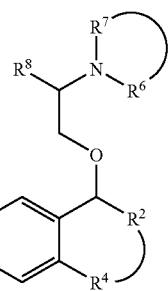
wherein each symbol is as defined above;
compounds wherein $R^3$ and $R^6$ are bonded to each other to form a ring, which are represented by the following formulas (Ie) to (VIe) and (VIIIe):
(Ie)
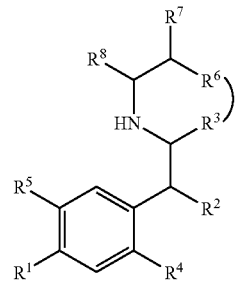
(IIe)
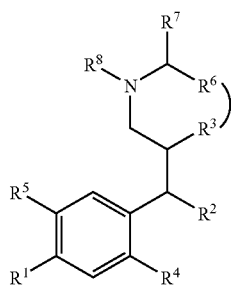
(IIIe)
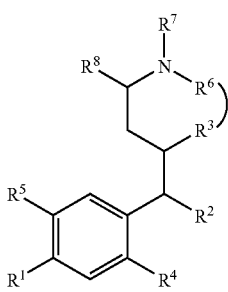
(IVe)
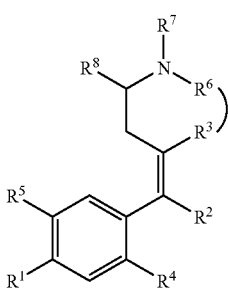

(Ve)

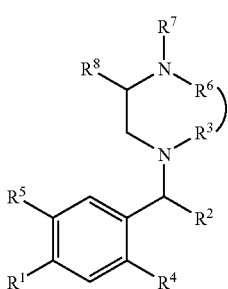

(VIe)

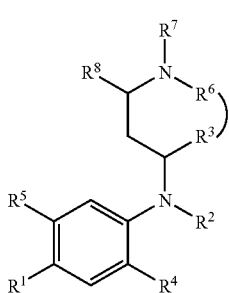

(VIIIe)

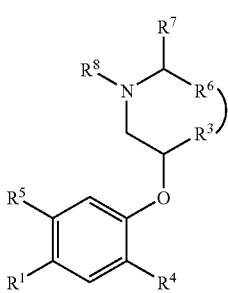

wherein each symbol is as defined above; and
compounds wherein $R^2$ and $R^4$ are bonded to each other to form a ring, and $R^3$ and $R^6$ are bonded to each other to form a ring, which are represented by the following formulas (If) to (VIf):

(If)

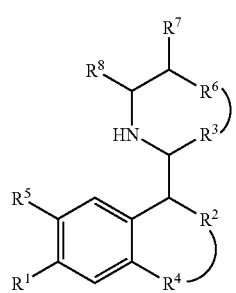

(IIf)

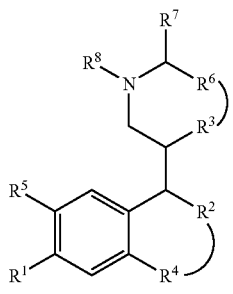

(IIIf)

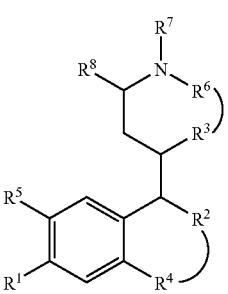

(IVf)

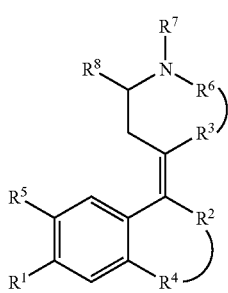

(Vf)

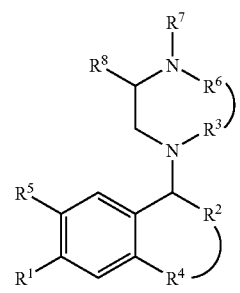

(VIf)

wherein each symbol is as defined above.

As the ring which is formed by $R^2$ and $R^4$ bonded to each other, for example, thiochromene, benzothiazine, dihydroquinoxaline, benzopyran, benzoxazine, dihydroquinoline, benzothiazepin, benzoxazepin, benzoxepin, benzothiepin, oxepin, thiepin, oxazepine, thiazepin, thiopyran, dihydropyrazine, pyran, thiazine, oxazine and the like can be mentioned, and it is preferably

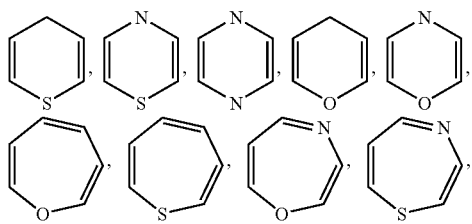

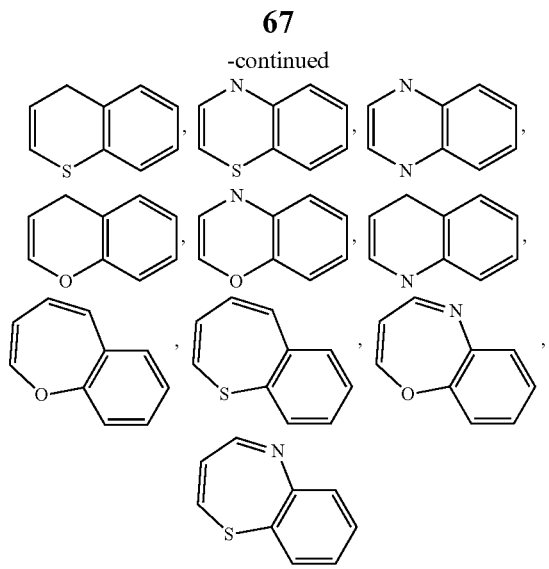

and the like, more preferably

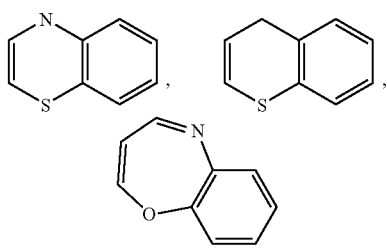

and the like.

As the ring which is formed by R³ and R⁶ bonded to each other, for example, pyrrolidine, piperidine, piperazine, homopiperidine, homopiperazine and the like can be mentioned, with preference given to piperidine and piperazine.

As the ring which is formed by R⁶ and R⁷ bonded to each other, for example, cyclopentane, cyclohexane, cycloheptane, pyrrolidine, piperidine, piperazine, homopiperidine, homopiperazine, morpholine, thiomorpholine and the like can be mentioned, with preference given to pyrrolidine, piperidine and piperazine.

As the ring which is formed by R⁷ and R⁸ bonded to each other, for example, cyclopentane, cyclohexane, cycloheptane, pyrrolidine, piperidine, piperazine, homopiperidine, homopiperazine, morpholine, thiomorpholine and the like can be mentioned, with preference given to piperidine.

$R^1$ is preferably a hydrogen atom, a fluorine atom, a chlorine atom, isopropylsulfanyl or 6-hydroxy-2-(4-hydroxyphenyl)benzo[b]thiophen-3-yl.

$R^2$ is preferably a hydrogen atom, hydroxy, phenyl, 4-fluorophenyl or 2-chlorophenyl, or $R^2$ is preferably bonded to $R^4$ to form

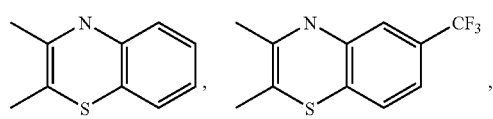

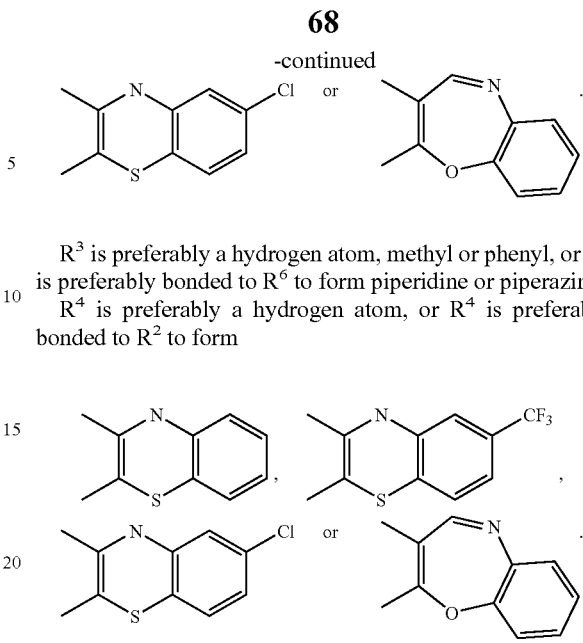

$R^3$ is preferably a hydrogen atom, methyl or phenyl, or $R^3$ is preferably bonded to $R^6$ to form piperidine or piperazine.

$R^4$ is preferably a hydrogen atom, or $R^4$ is preferably bonded to $R^2$ to form $R^5$ is preferably a hydrogen atom or a chlorine atom.

$R^6$ is preferably a hydrogen atom, methyl, hexyl, phenyl or cinnamyl, or $R^6$ is preferably bonded to $R^3$ to form piperidine or piperazine, or bonded to $R^7$ to form pyrrolidine, piperidine, piperazine, 1-methylpiperazine, 1-(2-hydroxyethyl)piperazine or 4-(benzimidazol-2-on-1-yl)piperidine.

$R^7$ is preferably a hydrogen atom, methyl, hexyl, phenyl or cinnamyl, or $R^7$ is preferably bonded to $R^6$ to form pyrrolidine, piperidine, piperazine, 1-methylpiperazine, 1-(2-hydroxyethyl)piperazine or 4-(benzimidazol-2-on-1-yl)piperidine, or bonded to $R^8$ to form piperidine.

$R^8$ is preferably a hydrogen atom or isobutyloxymethyl, or $R^8$ is preferably bonded to $R^7$ to form piperidine.

As preferable specific examples of the compound represented by the formula (1), Suloctidil can be mentioned.

As preferable specific examples of the compound represented by the formula (II), fendiline can be mentioned.

The formula (III) is preferably the formula (IIIb). As preferable specific examples of the compound represented by the formula (III), Pimozide can be mentioned.

The formula (IV) is preferably the formula (IVc), the formula (IVd) or the formula (IVf). As preferable specific examples of the compound represented by the formula (IV), Flupentixol, Chlorprothixene, Pimethixene and the like can be mentioned.

The formula (V) is preferably the formula (Vb), the formula (Ve) or the formula (Vf). As preferable specific examples of the compound represented by the formula (V), Bepridil, Flunarizine, Loxapine and the like can be mentioned.

The formula (VI) is preferably the formula (VId). As preferable specific examples of the compound represented by the formula (VI), Trifluoperazine and the like can be mentioned.

The formula (VII) is preferably the formula (VIIb). As preferable specific examples of the compound represented by the formula (VII), Cloperastine and the like can be mentioned.

The formula (VIII) is preferably the formula (VIIIa). As preferable specific examples of the compound represented by the formula (VIII), Raloxifene hydrochloride and the like can be mentioned.

As other preferable embodiments of the compounds represented by the formula (1) to the formula (VIII), for example, a compound wherein, in the formula (1) to the formula (VIII), any one of $R^1$, $R^2$, $R^3$, $R^4$, $R^5$, $R^6$, $R^7$ and $R^8$ is, instead of the above-mentioned definition, a group selected from the group consisting of the formulas (B) to (D):

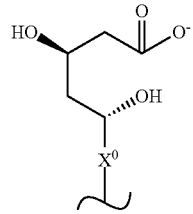
(B)

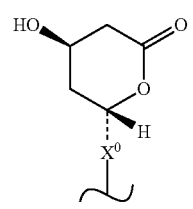
(C)

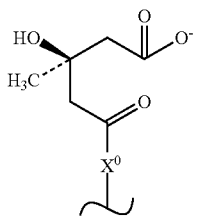
(D)

wherein $X^0$ is straight chain or branched alkylene having 1 to 5 carbon atoms, and the like can be mentioned.

In the formula (1), Bridge$^1$ is preferably (1a), $R^{1a}$ is preferably 4-fluorophenyl, $R^{2a}$ is preferably phenyl, and $R^{3a}$ is preferably phenyl.

In the formula (1'), the preferable embodiment is similar to that of the formula (1). In addition, a compound wherein any one of $R^{0a'}$, $R^{4a'}$, $R^{5a'}$ and $R^{6a'}$ is a group selected from the group consisting of the formulas (1B) to (1D):

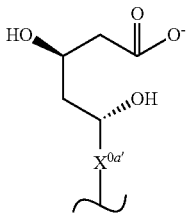
(1B)

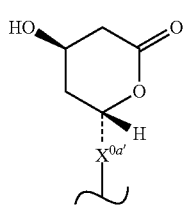
(1C)

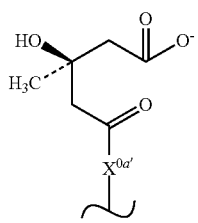
(1D)

wherein $X^{0a'}$ is straight chain or branched alkylene having 1 to 5 carbon atoms is also preferable.

In the formula (2), Bridge$^2$ is preferably a bridge structure selected from the group consisting of the following formulas

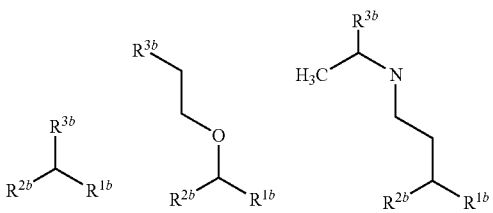

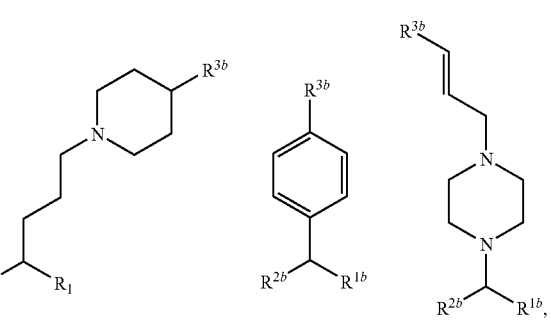

$R^{1b}$ is preferably phenyl, 4-chlorophenyl or 4-fluorophenyl, $R^{2b}$ is preferably phenyl, 4-fluorophenyl, 4-biphenyl or imidazol-1-yl, and $R^{3b}$ is preferably phenyl, 4-biphenyl, benzimidazol-2-on-1-yl, imidazol-1-yl or piperidin-1-yl.

As preferable specific examples of the compound represented by the formula (2), Pimozide, Bifonazole, Flunarizine, fendiline and Cloperastine can be mentioned.

In the formula (2'), the preferable embodiment is similar to that of the formula (2). In addition, a compound wherein any one of $R^{4b'}$, $R^{5b'}$ and $R^{6b'}$ is a group selected from the group consisting of the formulas (2B) to (2D):

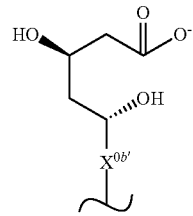
(2B)

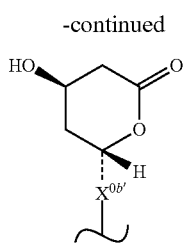
(2C)

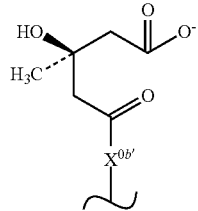
(2D)

wherein $X^{0b'}$ is straight chain or branched alkylene having 1 to 5 carbon atoms is also preferable.

In the formula (3), Bridge$^3$ is preferably (3e), $R^{1c}$ is preferably phenyl, $R^{2c}$ is preferably phenyl, $R^{3c}$ is preferably pyrrolidin-1-yl, and $R^{4c}$ is preferably isobutyl.

As preferable specific examples of the compound represented by the formula (3), Bepridil can be mentioned.

In the formula (3'), the preferable embodiment is similar to that of the formula (3). In addition, a compound wherein any one of $R^{0c_1}$, $R^{4c_1}$, $R^{5c_1}$, $R^{6c_1}$ and $R^{7c_1}$ is a group selected from the group consisting of the formulas (3B) to (3D):

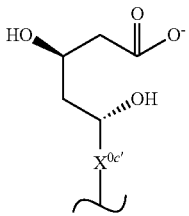
(3B)

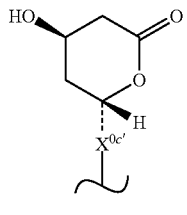
(3C)

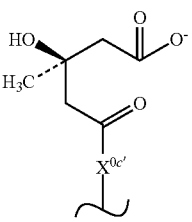
(3D)

wherein $X^{0c_1}$ is straight chain or branched alkylene having 1 to 5 carbon atoms is also preferable.

In the formula (4), $R^{1d}$ is preferably 3,5-dibromo-4-hydroxyphenyl or 4-[2-(piperidin-1-yl)ethoxy]phenyl, and $R^{2d}$ is preferably 2-ethylbenzo[b]furan-3-yl or 2-(4-hydroxyphenyl)-6-hydroxybenzo[b]thiophen-3-yl.

As preferable specific examples of the compound represented by the formula (4), Raloxifene hydrochloride and Benzbromarone can be mentioned.

In the formula (4'), the preferable embodiment is similar to that of the formula (4). In addition, a compound wherein any one of $R^{4d_1}$ and $R^{5d_1}$ is a group selected from the group consisting of the formulas (4B) to (4D):

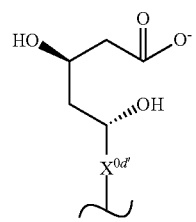
(4B)

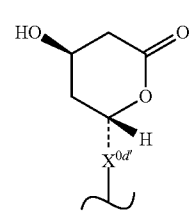
(4C)

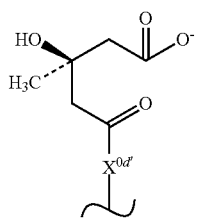
(4D)

wherein $X^{0d_1}$ is straight chain or branched alkylene having 1 to 5 carbon atoms is also preferable.

In the formula (5), $R^{1e}$ is preferably phenyl or 2-chlorophenyl, $R^{3e}$ is preferably methyl or isopropylmethyl, and $R^{2e}$ is preferably benzene or thiophene.

As preferable specific examples of the compound represented by the formula (5), Prazepam and Clotiazepam can be mentioned.

In the formula (5'), the preferable embodiment is similar to that of the formula (5). In addition, a compound wherein any one of $R^{3e_1}$, $R^{4e_1}$, $R^{5e_1}$ and $R^{6e_1}$ is a group selected from the group consisting of the formulas (5B) to (5D):

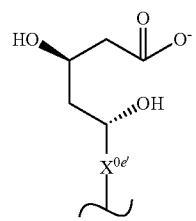
(5B)

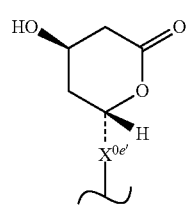
(5C)

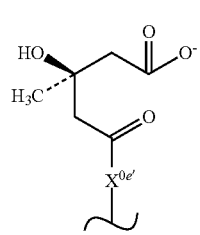
(5D)

wherein $X^{0e'}$ is straight chain or branched alkylene having 1 to 5 carbon atoms is also preferable.

In the formula (6), Bridge$^6$ is preferably a bridge structure selected from the group consisting of the formulas

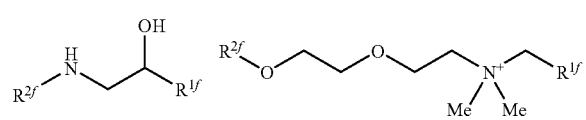

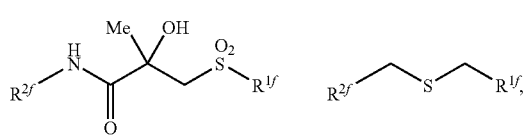

$R^{1f}$ is preferably phenyl, 4-isopropylphenyl or 4-fluorophenyl, and $R^{2f}$ is preferably phenyl, 4-(1,1,3,3-tetrabutyl)phenyl, octyl, 4-cyano-3-trifluoromethylphenyl or a group represented by the formula (f1):

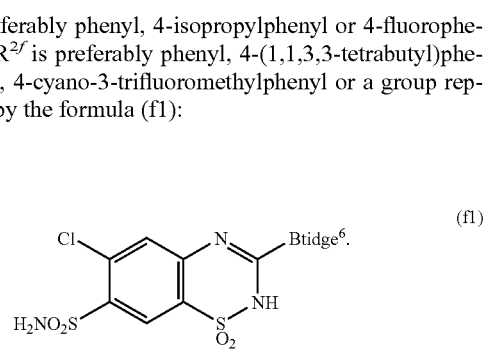
(f1)

As preferable specific examples of the compound represented by the formula (6), Suloctidil, Benzethonium, Bicaltamide and Benzthiazide can be mentioned.

In the formula (6'), the preferable embodiment is similar to that of the formula (6). In addition, a compound wherein any one of $R^{4f'}$ and $R^{5f'}$ is a group selected from the group consisting of the formulas (6B) to (6D):

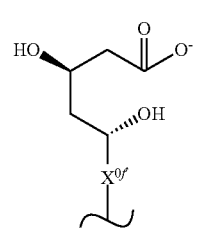
(6B)

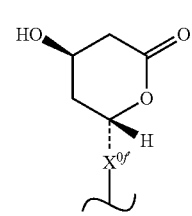
(6C)

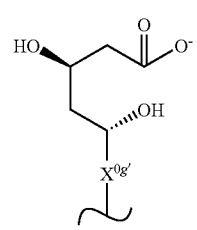
(6D)

wherein $X^{0f'}$ is straight chain or branched alkylene having 1 to 5 carbon atoms is also preferable.

In the formula (7), $X^{12}$ is preferably ethylene, $R^{1g}$ is preferably phenyl, 4-isopropylphenyl or 4-fluorophenyl, $R^{2g}$ is preferably pyridazine-3,6-diyl, and $R^{3g}$ is preferably morpholin-1-yl.

As preferable specific examples of the compound represented by the formula (7), Minaprine can be mentioned.

In the formula (7'), the preferable embodiment is similar to that of the formula (7). In addition, a compound wherein any one of $R^{3g'}$, $R^{4g'}$, $R^{5g'}$ and $R^{6g'}$ is a group selected from the group consisting of the formulas (7B) to (7D):

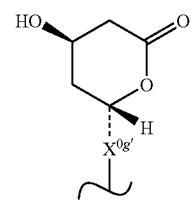
(7B)

(7C)

-continued

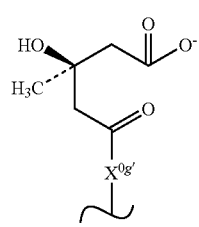
(7D)

wherein $X^{0g'}$ is straight chain or branched alkylene having 1 to 5 carbon atoms is also preferable.

In the formulas (8a) to (8j), compounds which are selected from the group consisting of the formulas

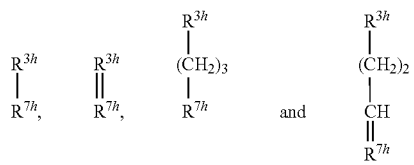

are preferable. Here, $R^{3h}$ is preferably 4-chlorophenyl, 4-methylpiperazin-1-yl, 4-(2-hydroxyethyl)piperazin-1-yl, 3-(N,N-dimethylamino)propylidene or 1-methylpiperidin-4-ylidene, and $R^{7h}$ is preferably, thioxanthen-9-ylidene, 2-chlorothioxanthen-9-ylidene, 2-trifluoromethylthioxanthen-9-ylidene, 2-trifluoromethylphenothiazin-10-yl, 2-chlorodibenzo[b,f][1,4]oxazepin-11-yl or a group represented by

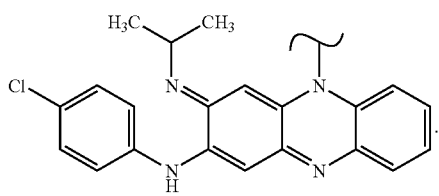

As preferable specific examples of the compound represented by the formulas (8a) to (8j), Trifluoperazine, Chlorprothixene, Pimethixene, Flupentixol, Clofazimine and Loxapine can be mentioned.

In the formulas (8a') to (8j'), the preferable embodiments are similar to those of the formulas (8a) to (8j). In addition, a compound wherein any one of $R^{3h'}$, $R^{5h'}$ and $R^{6h'}$ is a group selected from the group consisting of the formulas (8B) to (8D):

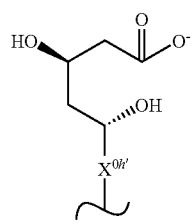
(8B)

-continued

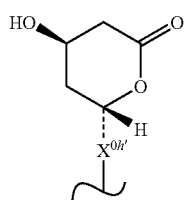
(8C)

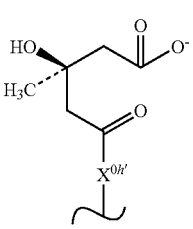
(8D)

wherein $X^{0h'}$ is straight chain or branched alkylene having 1 to 5 carbon atoms is also preferable.

In the formula (9), $R^{9i}$ is preferably 3,4,5-trimethoxyphenyl or 3,5-dimethoxy-4-ethoxycarbonyloxyphenyl.

As preferable specific examples of the compound represented by the formula (9), Rescinnamine and Syrosingopine can be mentioned.

In the formula (9'), the preferable embodiment is similar to that of the formula (9). In addition, a compound wherein any one of $R^{6i'}$ and $R^{9i'}$ is a group selected from the group consisting of the formulas (9B) to (9D):

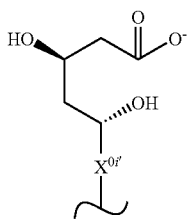
(9B)

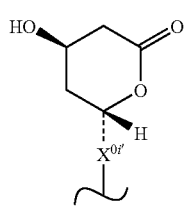
(9C)

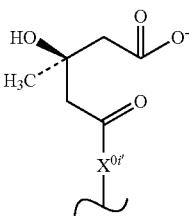
(9D)

wherein $X^{0i'}$ is straight chain or branched alkylene having 1 to 5 carbon atoms is also preferable.

In the formula (10), Bridge$^{10}$ is preferably (10a), and R$^{11j}$ is preferably a group represented by the formula (j2)

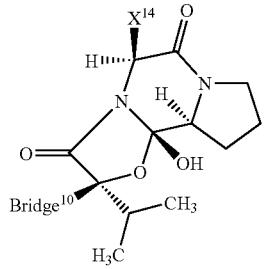
(j2)

wherein X$^{14}$ is isopropyl, isobutyl, sec-butyl or benzyl.

As preferable specific examples of the compound represented by the formula (10), Dihydroergocornine mesylate, Dihydro-α-ergocryptine mesylate, Dihydro-β-ergocryptine mesylate and Dihydroergocristine mesylate can be mentioned.

In the formula (10'), the preferable embodiment is similar to that of the formula (10). In addition, a compound wherein any one of R$^{6j\prime}$ and R$^{11j\prime}$ is a group selected from the group consisting of the formulas (10B) to (10D):

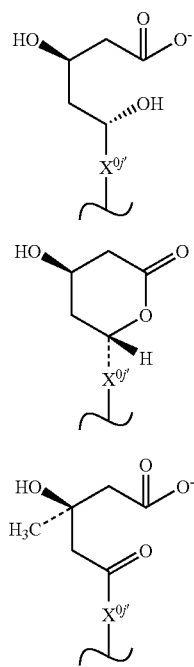

(10B)

(10C)

(10D)

wherein X$^{0j\prime}$ is straight chain or branched alkylene having 1 to 5 carbon atoms is also preferable.

In the formula (11), R$^{12k}$ is preferably (11a), and R$^{13k}$ is preferably methyl.

As preferable specific examples of the compound represented by the formula (11), Stanozolol can be mentioned.

In the formula (11'), the preferable embodiment is similar to that of the formula (11). In addition, a compound wherein any one of R$^{6k\prime}$ and R$^{13k\prime}$ is a group selected from the group consisting of the formulas (11B) to (11D):

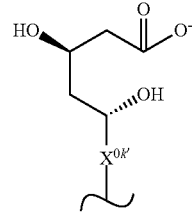
(11B)

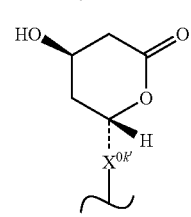
(11C)

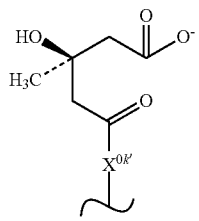
(11D)

wherein X$^{0k\prime}$ is straight chain or branched alkylene having 1 to 5 carbon atoms is also preferable.

Any compound represented by the formulas (1) to (VIII), the formulas (1) to (11) and the formulas (1') to (11') may be generally referred to as the compound of the present invention.

Any compound represented by the formulas (1') to (11') has an ability to bind to neurocalcin, and can bind to HMG-CoA reductase. Accordingly, it is expected that the compound can exert an action of lowering cholesterol in blood, which is based on HMG-CoA reductase inhibiting activity, and therefore show extensive effects such as prophylaxis of cerebrovascular disorder (cerebral infarction, transient cerebral ischemia) or dementia due to hyperlipidemia.

The compound of the present invention may form pharmaceutically acceptable carrier. The Examples of the salt include acid addition salts such as salts with inorganic acids (e.g., hydrochloride, sulfate, hydrobromate, phosphate, etc.) or salts with organic acids (e.g., acetate, trifluoroacetate, succinate, maleate, fumarate, propionate, citrate, tartrate, lactate, oxalate, methanesulfonate, p-toluenesulfonate, etc.).

The compound of the present invention or a salt thereof may be solvate such as hydrate.

2. Screening Method and Product Obtained by the Method

The present invention provides screening methods for drugs, comprising determining whether or not a test substance is capable of regulating the expression or function of the NCS protein gene. The screening methods of the present invention can be roughly divided into a screening method for substances capable of regulating an action associated with NCS protein-targeting drug (for example, central nervous action), and a screening method for substances capable of regulating a function associated with the NCS protein gene, from the viewpoint of the kind of drug to be screened. The screening methods of the present invention can also be performed in vitro, in vivo or in silico. The substance capable of regulating the expression of NCS protein gene, which is obtained by the screening method of the present invention, has the same definition as a substance capable of regulating the amount of NCS protein, and can be a substance capable of altering an amount of NCS protein existed in a certain tissue or cell, or an amount of NCS protein existed in a certain subcellular localization. Therefore, the examples of the substance capable of regulating the expression of NCS protein gene include not only a substance capable of regulating biosynthesis of NCS protein from NCS protein gene, but also a substance capable of regulating subcellular localization of NCS protein and a substance capable of regulating metabolism (e.g., degradation associated with metabolism) of NCS protein. The individual screening methods are hereinafter described in detail.

2.1. Screening Method for Substances Capable of Regulating an Action Associated with NCS Protein-Targeting Drug (Screening Method I)

The present invention provides a screening method for substances capable of regulating an action associated with NCS protein-targeting drug, which comprises determining whether or not a test substance is capable of regulating the expression or function of the NCS protein gene.

This screening method is optionally abbreviated as "screening method I."

Screening method I can be roughly divided into two types: a screening method for a substance capable of regulating an action associated with NCS protein-targeting drug, which comprises determining whether or not a test substance is capable of regulating the expression or function of NCS protein gene, and selecting a test substance capable of regulating the expression or function of NCS protein gene (screening method Ia), and a screening method for a substance capable of regulating an action associated with NCS protein-targeting drug (particularly an action associated with known target molecule), which comprises determining whether or not a test substance is capable of regulating the expression or function of NCS protein gene, and selecting a test substance that is incapable of regulating the expression or function of NCS protein gene (screening method Ib). Screening method Ia can be useful for the development of regulators of diseases or conditions associated with NCS protein-targeting drug and the like. Screening method Ib can be useful for the development of drugs capable of regulating an action associated with known target molecule, and showing decreased adverse effects of NCS protein-targeting drug and the like.

2.1.1. Screening Method for Substances Capable of Regulating an Action Associated with NCS Protein-Targeting Drug, which Comprises Selecting a Test Substance Capable of Regulating the Expression or Function of NCS Protein Gene (Screening Method Ia)

The test substance subjected to the screening method may be any known compound or new compound; examples include nucleic acids, saccharides, lipids, proteins, peptides, organic small compounds, compound libraries prepared using combinatorial chemistry technique, random peptide libraries prepared by solid phase synthesis or the phage display method, or natural components derived from microorganisms, animals, plants, marine organisms and the like, and the like.

The test substance may be labeled or unlabeled. In addition, a mixture comprising a labeled substance and an unlabeled substance in a specified ratio can be used as the test substance. The labeling substance is the same as described above.

In one embodiment, screening method Ia comprises the following steps (a), (b) and (c):
(a) a step for bringing the test substance into contact with NCS protein;
(b) a step for measuring the functional level of the protein in the presence of the test substance, and comparing this functional level with the functional level of the protein in the absence of the test substance;
(c) a step for selecting a test substance that alters the functional level of the protein on the basis of the result of the comparison in step (b) above.

The methodology comprising the above-described steps (a) to (c) is referred to as "methodology I" as required.

In step (a) of methodology I, a test substance is brought into contact with NCS protein. Contact of the test substance with the protein can be performed by contact of isolated NCS protein and the test substance in solution, or contact of cells or tissue capable of expressing NCS protein, and the test substance.

NCS protein can be prepared by a method known per se. For example, NCS protein can be isolated and purified from the above-described expression tissue. However, to prepare NCS protein quickly, easily, and in large amounts, and to prepare human NCS protein, it is preferable to prepare a recombinant protein by gene recombination technology. The recombinant protein may be prepared using a cell system or a cell-free system.

The cells capable of expressing NCS protein can be any cells that express NCS protein; examples include cells derived from the tissue in which NCS protein is expressed, cells transformed with NCS protein expression vector and the like. Those skilled in the art are able to easily identify or prepare these cells; useful cells include primary culture cells, cell lines derivatively prepared from the primary culture cells, commercially available cell lines, cell lines available from cell banks, and the like. As the tissue capable of expressing NCS protein, the above-described expression tissues can be used.

In step (b) of methodology I, the functional level of the protein in the presence of the test substance is measured. A measurement of the functional level can be performed according to the method known per se which can measure the function of NCS protein.

The functional level may also be measured on the basis of the functional level of NCS protein to each isoform (e.g., splicing variant) or the isoform-isoform functional level ratio, rather than on the basis of the total functional level of NCS protein.

Next, the functional level of NCS protein in the presence of the test substance is compared with the functional level of NCS protein in the absence of the test substance. This comparison of functional level is preferably performed on the basis of the presence or absence of a significant difference. Although the functional level of NCS protein in the absence of the test substance may be measured prior to, or simultaneously with, the measurement of the functional level of NCS protein in the presence of the test substance, it is preferable, from the viewpoint of experimental accuracy and reproducibility, that the functional level be measured simultaneously.

In step (c) of methodology I, a test substance that alters the functional level of the protein is selected. The test substance that alters the functional level of the protein is capable of promoting or suppressing a function of NCS protein. The test substance thus selected can be useful for the regulation of a disease or condition associated with NCS protein-targeting drug.

In another embodiment, screening method Ia comprises the following steps (a), (b) and (c):
(a) a step for bringing a test substance into contact with cells enabling a measurement of the expression of the NCS protein gene;

(b) a step for measuring the expression level in the cells in contact with the test substance, and comparing this expression level with the expression level in control cells not in contact with the test substance;

(c) a step for selecting a test substance that regulates the expression level of the NCS protein gene on the basis of the result of the comparison in step (b) above.

The methodology comprising the above-described steps (a) to (c) is optionally abbreviated as "methodology II."

In step (a) of methodology II, a test substance is brought into contact with cells enabling a measurement of the expression of the NCS protein gene. Contacting the test substance with the cells enabling a measurement of the expression of the NCS protein gene can be performed in culture medium.

"Cells enabling a measurement of the expression of the NCS protein gene" refers to cells enabling a direct or indirect evaluation of the expression level of a product, for example, a transcription product or translation product, of the NCS protein gene. The cells enabling a direct evaluation of the expression level of a product of the NCS protein gene can be cells capable of naturally expressing the NCS protein gene, whereas the cells enabling an indirect evaluation of the expression level of a product of the NCS protein gene can be cells enabling a reporter assay on the transcription regulatory region for the NCS protein gene.

The cells capable of naturally expressing the NCS protein gene can be any cells that potentially express the NCS protein gene; examples include cells showing permanent expression of the NCS protein gene, cells that express the NCS protein gene under inductive conditions (e.g., drug treatment) and the like. Those skilled in the art are able to easily identify these cells; useful cells include primary culture cells, cell lines derivatively prepared from the primary culture cells, commercially available cell lines, cell lines available from cell banks, and the like. The cell lines expressing neurocalcin δ of NCS proteins include optic nerve cells, peripheral sensory nerve cells, nerve cells in brain, or lines derived from these cells.

The cells enabling a reporter assay on the transcription regulatory region for the NCS protein gene are cells incorporating the transcription regulatory region for the NCS protein gene and a reporter gene functionally linked to the region. The transcription regulatory region for the NCS protein gene and the reporter gene are inserted in an expression vector.

The transcription regulatory region for the NCS protein gene may be any region enabling the control of the expression of the NCS protein gene; examples include a region from the transcription initiation point to about 2 kbp upstream thereof, and a region consisting of a nucleotide sequence wherein one or more nucleotides are deleted, substituted or added in the nucleotide sequence of the region, and that is capable of controlling the transcription of the NCS protein gene, and the like.

The reporter gene may be any gene that encodes a detectable protein or enzyme; examples include the GFP (green fluorescent protein) gene, GUS (β-glucuronidase) gene, LUS (luciferase) gene, CAT (chloramphenicol acetyltransferase) gene and the like.

The cells transfected with the transcription regulatory region for the NCS protein gene and the reporter gene functionally linked to the region are not subject to limitation, as long as they enable an evaluation of the transcription regulatory function of the NCS protein gene, that is, as long as they enable a quantitative analysis of the expression level of the reporter gene. However, the cells transfected are preferably cells capable of naturally expressing the NCS protein gene because they are considered to express a physiological transcription regulatory factor for the NCS protein gene, and therefore to be more appropriate for the evaluation of the regulation of the expression of the NCS protein gene.

The culture medium in which a test substance and cells enabling a measurement of the expression of the NCS protein gene are brought into contact with each other is chosen as appropriate according to the kind of cells used and the like; examples include minimal essential medium (MEM) containing about 5 to 20% fetal bovine serum, Dulbecco's modified minimal essential medium (DMEM), RPMI1640 medium, 199 medium and the like. Culture conditions are also determined as appropriate according to the kind of cells used and the like; for example, the pH of the medium is about 6 to about 8, culture temperature is normally about 30 to about 40° C., and culture time is about 12 to about 72 hours.

In step (b) of methodology II, first, the expression level of the NCS protein gene in the cells in contact with the test substance is measured. The measurement of expression level can be performed by a method known per se in view of the kind of cells used and the like.

For example, when cells capable of naturally expressing the NCS protein gene are used as the cells enabling a measurement of the expression of the NCS protein gene, the expression level can be measured by a method known per se with a product, for example, a transcription product or translation product, of the NCS protein gene as the subject. For example, the expression level of a transcription product can be measured by preparing total RNA from the cells, and performing RT-PCR, Northern blotting and the like. The expression level of a translation product can be measured by preparing an extract from the cells, and performing an immunological technique. Useful immunological techniques include radioisotope immunoassay (RIA), ELISA (Methods in Enzymol. 70: 419-439 (1980)), fluorescent antibody method and the like.

On the other hand, when cells enabling a reporter assay on the transcription regulatory region for the NCS protein gene are used as the cells enabling a measurement of the expression of the NCS protein gene, the expression level can be measured on the basis of the signal intensity of the reporter.

The expression level may also be measured on the basis of the expression level of NCS protein gene to each isoform (e.g., splicing variant) or the isoform-isoform expression ratio, rather than on the basis of the total functional level of NCS protein gene.

Furthermore, the expression level can be measured based on localization to cell membrane. The amount of NCS protein localized in a cell can be measured by a method known per se. For example, NCS protein fused with a gene encoding a fluorescent protein such as GFP gene is introduced to a suitable cell, and the cell is cultured in a culture medium in the presence of a test substance. Next, fluorescent signal in the cell membrane is observed by confocal microscopy, and the fluorescent signal may be compared with fluorescent signal in the organ in the absence of the test substance. Furthermore, the amount of NCS protein localized to cell membrane can also be measured by immunostaining using an antibody against NCS protein.

Next, the expression level of the NCS protein gene in the cells in contact with the test substance is compared with the expression level of the NCS protein gene in control cells not in contact with the test substance. This comparison of expression level is preferably performed on the basis of the presence or absence of a significant difference. Although the expression level of the NCS protein gene in the control cells not in contact with the test substance may be measured prior to, or simultaneously with, the measurement of the expression level of the NCS protein gene in the cells in contact with the test substance, it is preferable, from the viewpoint of experimental accuracy and reproducibility, that the expression level be measured simultaneously.

In step (c) of methodology II, a test substance that regulates the expression level of the NCS protein gene is selected. The regulation of the expression level of the NCS protein gene can be the promotion or suppression of the expression level. The test substance thus selected can be useful for the regulation of an action associated with NCS protein-targeting drug.

In another embodiment, screening method Ia comprises the following steps (a), (b) and (c):
(a) a step for bringing a test substance into contact with NCS protein or a mutant protein thereof;
(b) a step for measuring the ability of the test substance to bind to the protein;
(c) a step for selecting a test substance having the ability of binding to the protein on the basis of the results of step (b) above.

The methodology comprising the above-described steps (a) to (c) is optionally abbreviated as "methodology III."

In step (a) of methodology III, a test substance is brought into contact with NCS protein. Contacting the test substance with the protein can be performed by mixing the test substance and the protein in solution.

NCS protein can be prepared by a method known per se. For example, NCS protein can be isolated and purified from the above-described expression tissue of the NCS protein gene. However, to prepare NCS protein quickly, easily, and in large amounts, and to prepare human NCS protein, it is preferable to prepare a recombinant protein by gene recombination technology. The recombinant protein may be prepared using a cell system or a cell-free system. The mutant protein having the ability of binding to an NCS protein-targeting drug also can be easily prepared by those skilled in the art with a method known per se. The mutant protein is as described above.

In step (b) of methodology III, the ability of the test substance to bind to the protein is measured. The measurement of the binding ability can be performed by a method known per se. Furthermore, the binding strength, the dose dependency of the test substance in binding to the protein, and the like can also be measured, in addition to the binding ability. The binding strength and the dose dependency can be measured by appropriately selecting a measuring means.

The measurement of the binding ability can be performed by, for example, the SEC/MS (size exclusion chromatography/mass analysis) method (see Moy, F. J. et al., Anal. Chem., 2001, 73, 571-581). The SEC/MS method comprises (1) a step for adding a mixed multiplied compound standard to the purified protein, and then separating the free compound and the protein by SEC, and (2) an analytical step for identifying the bound compound contained in the protein fraction by MS. The SEC/MS method is advantageous in that the binding ability can be analyzed while both the protein and the test substance are in non-modified and non-immobilized state. In the SEC/MS method, not only the ability of the test substance to bind to the protein, but also the dose dependency of the test substance in the binding to the protein and the like can be measured simultaneously.

The measurement of the binding ability can also be performed using a means for measurement based on surface plasmon resonance, for example, Biacore. Using Biacore, the binding and dissociation of a test substance to a protein immobilized on a chip are measured, and the measured values are compared with those obtained when a solution not containing the test substance is loaded on the chip. Subsequently, a test substance capable of binding to the protein is selected on the basis of the result for the binding and dissociation rate or binding amount. Biacore also enables simultaneous measurements of binding strength (e.g., $K_d$ value) and the like, in addition to the ability of a test substance to bind to a protein.

Other methods for measuring the binding ability include, for example, SPR-based methods or optical methods such as the quartz crystal microbalance (QCM) method, the dual polarization interferometer (DPI) method, and the coupled waveguide plasmon resonance method, immunoprecipitation, isothermal titration and differential scanning calorimetry, capillary electrophoresis, energy transfer, fluorescent analytical methods such as fluorescent correlation analysis, and structural analytical methods such as X-ray crystallography and nuclear magnetic resonance (NMR).

In measuring the binding ability, an NCS protein-binding substance can also be used as a control.

"A NCS protein-binding substance" is a compound capable of interacting directly with NCS protein or a mutant protein thereof, and can be, for example, a protein, a nucleic acid, a carbohydrate, a lipid, or a small organic compound. Preferably, the NCS protein-binding substance can be the NCS protein-targeting drug described above, and can be, for example, atorvastatin, pimozide, bifonazole, flunarizine, fendiline, chloperastine, bepridil, raloxifene hydrochloride, benzbromarone, prazepam, clotiazepam, suloctidil, benzethonium, bicaltamide, benzthiazide, minaprine, trifluoperazine, chlorprothixene, pimethixene, flupentixol, clofazimine, loxapine, rescinnamine, syrosingopine, dihydroergocornine mesylate, dihydro-α-ergocryptine mesylate, dihydro-β-ergocryptine mesylate, dihydroergocristine mesylate or stanozolol, or a derivative thereof capable of binding to NCS protein, or a salt thereof.

Although the salts may be any salts, pharmaceutically acceptable salts are preferable; examples include salts with inorganic bases (e.g., alkali metals such as sodium and potassium; alkaline earth metals such as calcium and magnesium; aluminum, ammonium), salts with organic bases (e.g., trimethylamine, triethylamine, pyridine, picoline, ethanolamine, diethanolamine, triethanolamine, dicyclohexylamine, N,N-dibenzylethylenediamine), salts with inorganic acids (e.g., hydrochloric acid, hydrobromic acid, nitric acid, sulfuric acid, phosphoric acid), salt with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid), salts with basic amino acids (e.g., arginine, lysine, ornithine) or salts with acidic amino acids (e.g., aspartic acid, glutamic acid) and the like.

Furthermore, the binding ability may also be measured on the basis of the binding ability of NCS protein to each isoform (e.g., splicing variant) or the isoform-isoform binding ability ratio, rather than on the basis of the total binding ability of NCS protein.

The binding ability can also be measured in silico. For example, a measurement of the binding ability can be performed on the basis of SBDD (structure-based drug design: SBDD) or CADD (computer-aided drug design). Examples of such screening include virtual screening, de novo design, pharmacophore analysis, QSAR (quantitative structure activity relationship) and the like. If information on the steric structure of the protein or the target site of the protein is required during such screening, the information on the steric structure is used, provided that the steric structure is known by a structural analytical technique such as NMR, X-ray crystallographic analysis, or synchrotron radiation analysis. If the steric structure is unknown, information obtained by a structural estimation method such as the homology method or the threading method is used. In virtual screening, a program known per se can be used; examples of the program include DOCK (Kuntz, I. D. et al., Science, 1992, 257, 1078), Gold (Jones, G. et al., J. Mol. Biol., 1995, 245, 43), FlexX (Rarey, M. et al., J. Mol. Biol., 1996, 261, 470), AutoDock (Morris, G. M. et al., J. Comput. Chem., 1998, 19, 1639), ICM (Abagyan, R. A. et al., J. Comput. Chem., 1994, 15, 488) and the like.

In step (c) of methodology III, a test substance capable of binding to NCS protein is selected. The test substance capable of binding to the protein is capable of promoting or suppressing a function of the NCS protein gene. The test substance thus selected can be useful for the regulation of a disease associated with NCS protein-targeting drug.

In still another embodiment, screening method Ia comprises the following steps (a), (b) and (c):
(a) a step for bringing a test substance and an NCS protein-binding substance into contact with NCS protein or a mutant protein thereof;
(b) a step for measuring the amount of the NCS protein-binding substance to bind to the protein in the presence of the test substance, and comparing this binding amount with the amount of the NCS protein-binding substance to bind to the protein in the absence of the test substance;
(c) a step for selecting a test substance that alters the amount of the NCS protein-binding substance to bind to the protein on the basis of the result of the comparison in step (b) above.

The methodology comprising the above-described steps (a) to (c) is optionally abbreviated as "methodology IV."

In step (a) of methodology IV, both a test substance and the NCS protein-binding substance are brought into contact with NCS protein or a mutant protein thereof. Contacting the test substance and the NCS protein-binding substance with the protein can be performed by mixing the test substance, the NCS protein-binding substance, and the protein in solution. The order of bringing the test substance and NCS protein-binding substance into contact with the protein is not subject to limitation; one of them may be brought into contact with the protein in advance or at the same time.

NCS protein and the mutant protein thereof can be prepared by a method known per se. For example, preparation of the protein can be performed by a method described in methodology III above.

The NCS protein-binding substance may be labeled or unlabeled. In addition, a mixture comprising a labeled substance and an unlabeled substance in a specified ratio can be used as the NCS protein-binding substance. The labeling substance is the same as described above.

In step (b) of methodology IV, first, the amount of the NCS protein-binding substance to bind to the protein is measured in the presence of the test substance. The measurement of the binding amount can be performed by a method known per se, in view of kinds of the NCS protein-binding substance used, the presence or absence of the label, and the like. Furthermore, the binding strength (for example, $K_d$ value), the dose dependency of the test substance in the binding to the protein, and the like can also be measured, in addition to the binding amount. The binding strength and the dose dependency can be measured by appropriately selecting a measuring means.

The measurement of the binding amount can be performed using, for example, a labeled NCS protein-binding substance. The NCS protein-binding substance bound to the protein and the unbound NCS protein-binding substance may be separated before measuring the binding amount. More specifically, the measurement can be performed in the same manner as methodology III.

The binding ability may also be measured on the basis of the binding ability of NCS protein to each isoform (e.g., splicing variant) or the isoform-isoform binding ability ratio, rather than on the basis of the total amount of NCS protein bound.

Next, the binding amount of the NCS protein-binding substance to the protein in the presence of the test substance is compared with the binding amount of the NCS protein-binding substance to the protein in the absence of the test substance. The comparison of the binding amount is preferably performed on the presence or absence of a significant difference. Although the binding amount of the NCS protein-binding substance to the protein in the absence of the test substance may be measured prior to, or simultaneously with, the measurement of the binding amount of the NCS protein-binding substance to the protein in the presence of the test substance, it is preferable, from the viewpoint of experimental accuracy and reproducibility, that the binding amount be measured simultaneously.

In step (c) of methodology IV, a test substance that alters the amount of the NCS protein-binding substance to bind to the protein is selected. The change in the binding amount can be, for example, a reduction or increase of binding amount, with preference given to a reduction of binding amount. The test substance thus selected can be useful for the regulation of an action associated with NCS protein-targeting drug.

In addition, screening method Ia can further comprise (d) (i) a step for confirming that the selected test substance is capable of regulating, for example, promoting or suppressing, an action associated with NCS protein-targeting drug (confirmation step), or (ii) a step for identifying the kind of action exhibited by the selected test substance (identification step). The confirmation step or identification step can be performed by, for example, administering the test substance to a normal animal, or to an animal with "a disease associated with NCS protein-targeting drug" or model animal. Alternatively, these steps can also be performed by contacting a test substance with cells, and evaluating change in phenotypes of the contacted cells. According to this identification step, the kind of "action associated with NCS protein-targeting drug" exhibited by the selected test substance can be determined, and whether or not the selected test substance can be used as either a drug or an investigational reagent, or both a drug or an investigational reagent, and the kind of drug or investigational reagent to which the test substance is applicable can be confirmed.

Screening method Ia can also be performed by administration of a test substance to an animal. In this case, not only the expression level of NCS protein gene, but also the expression level of NCS protein (e.g., the amount of NCS protein existed in a certain tissue or cell from an animal administered with a test substance, or localization in cell membrane) may be measured. Examples of the animal include mammals such as mice, rats, hamsters, guinea pigs, rabbits, dogs, and monkeys, and birds such as chickens. When a screening method of the present invention is performed using an animal, for example, a test substance that regulates the expression level of the NCS protein gene can be selected.

Screening method Ia enables screening of a substance capable of regulating an action associated with NCS protein-targeting drug. Hence, screening method Ia is useful for the development of a prophylactic or therapeutic agent for a disease associated with NCS protein-targeting drug (for example, central nervous disease), and an investigational reagent for the disease, and the like.

2.1.2. Screening Method for Substances Capable of Regulating an Action Associated with NCS Protein-Targeting Drug, which Comprises Selecting a Test Substance Incapable of Regulating the Expression or Function of NCS Protein Gene (Screening Method Ib)

The present invention provides a screening method for substances capable of regulating an action associated with NCS protein-targeting drug (particularly an action associated with known target molecule and/or a pharmacological action actually shown by NCS protein-targeting drug) (for example, a substance which can be used for the same medical use as NCS protein-targeting drug, which exerts a pharmacological action actually shown by NCS protein-targeting drug, and does not exert adverse effect actually shown by NCS protein-targeting drug or exert decreased adverse effect), which comprises determining whether or not a test substance is capable of regulating the expression or function of NCS protein gene, and selecting a test substance incapable of regulating the expression or function of NCS protein gene.

Screening method Ib can be performed in the same manner as methodologies I to IV except that a test substance that does not cause a change or does not have the binding ability or regulatory capacity in step (c) of the above-described methodologies I to IV is selected.

In screening method Ib, the test substance used can be one capable of regulating the expression or function of a known target molecule, or one having an action associated with NCS protein-targeting drug (particularly, a pharmacological action actually showed by NCS protein-targeting drug). Hence, screening method Ib can be used in combination with a screening method for substances capable of regulating an action associated with a known target molecule, which comprises determining whether or not the test substance is capable of regulating the expression or function of the known target molecule. The screening method for substances capable of regulating an action associated with a known target molecule can be performed in the same manner as the above-described screening method Ia. Alternatively, screening method Ib can be used in combination with a screening method for substances capable of regulating an action associated with NCS protein-targeting drug, which comprises determining whether or not the test substance is capable of regulating the action associated with NCS protein-targeting drug (particularly a pharmaceutical action actually shown by NCS protein-targeting drug). Such a screening method can be performed using an animal or cells in the same manner as the step (d) of the above-described screening method Ia.

Screening method Ib enables the development of drugs capable of regulating an action associated with a known target molecule, and showing decreased adverse effects of NCS protein-targeting drug. Hence, screening method Ib is useful for the improvement of existing drugs capable of regulating an action associated with a known target molecule, and the like.

2.2. Screening Method for Substances Capable of Regulating a Function Associated with the NCS Protein Gene (Screening Method II)

The present invention provides a screening method for substances capable of regulating a function associated with the NCS protein gene, which comprises evaluating whether or not a test substance is capable of regulating the ability of an NCS protein-targeting drug to bind to NCS protein or a mutant protein thereof.

This screening method is optionally abbreviated as "screening method II."

In one embodiment, screening method II comprises the following steps (a), (b) and (c):

(a) a step for bringing a test substance and an NCS protein-targeting drug into contact with NCS protein or a mutant protein thereof capable of binding to the NCS protein-targeting drug;

(b) a step for measuring the amount of the NCS protein-targeting drug to bind to the protein in the presence of the test substance, and comparing this binding amount with the amount of the NCS protein-targeting drug to bind to the protein in the absence of the test substance;

(c) a step for selecting a test substance that alters the amount of the NCS protein-targeting drug to bind to the protein on the basis of the result of the comparison in step (b) above.

The methodology comprising the above-described steps (a) to (c) is the same as methodology IV except that "an NCS protein-targeting drug" is used instead of "an NCS protein-binding substance."

Screening method II enables, for example, screening of substances capable of regulating a function associated with the NCS protein gene, probes for NCS protein, and the like. Hence, screening method II is useful for the screening of prophylactic or therapeutic agents for diseases associated with the NCS protein gene, and investigational reagents for the diseases, and the like.

2.3. Products Obtained by Screening Methods

The present invention provides products obtained by the above-described screening methods, for example, screening methods I and II.

The product provided by a screening method of the present invention can be a substance obtained by the screening method of the present invention, or a regulator of pharmacological action, comprising a substance obtained by the screening method.

The product provided by the screening method of the present invention is useful for, for example, the prevention or treatment of a disease associated with NCS protein-targeting drug, or a disease associated with the NCS protein gene, or as an investigational reagent for the disease, or the like.

3. Regulator

The present invention provides regulators of pharmacological action, each of which a substance that regulates the expression or function of the NCS protein gene. The regulators of the present invention can be roughly divided into a regulator of an action associated with NCS protein-targeting drug (e.g., central nervous action), and a regulator of a function associated with the NCS protein gene, from the viewpoint of the pharmacological action to be regulated. The individual regulators are hereinafter described in detail.

3.1. Regulator of an Action Associated with NCS Protein-Targeting Drug (Regulator I)

The present invention provides a regulator of an action associated with NCS protein-targeting drug, comprising a substance that regulates the expression or function of the NCS protein gene.

This regulator is optionally abbreviated as "regulator I."

The substance that regulates the expression or function of the NCS protein gene can be, for example, a substance that suppresses the expression of the NCS protein gene. The expression refers to a state in which a translation product of the NCS protein gene is produced and is localized at the action site thereof in a functional condition. Hence, the substance that suppresses the expression may be one that acts in any stage of gene transcription, post-transcriptional regulation, translation, post-translational modification, localization and protein folding and the like.

Specifically, the substance that suppresses the expression of the NCS protein gene is exemplified by transcription suppressor, RNA polymerase inhibitor, RNA decomposing enzyme, protein synthesis inhibitor, nuclear translocation inhibitor, protein decomposing enzyme, protein denaturant and the like; to minimize the adverse effects on other genes and proteins expressed in the cells, it is important that the substance be capable of specifically acting on the target molecule.

An example of the substance that suppresses the expression of the NCS protein gene is an antisense nucleic acid to a transcription product, specifically, mRNA or initial transcription product, of the NCS protein gene. "An antisense nucleic acid" refers to a nucleic acid that consists of a nucleotide sequence capable of hybridizing to the target mRNA (initial transcription product) under physiological conditions for cells that express target mRNA (initial transcription product), and capable of inhibiting the translation of the polypeptide encoded by the target mRNA (initial transcription product) in a hybridized state. The kind of antisense nucleic acid may be DNA or RNA, or a DNA/RNA chimera. Because a natural type antisense nucleic acid easily undergoes degradation of the phosphoric acid diester bond thereof by a nucleic acid decomposing enzyme present in the cells, an antisense nucleic acid of the present invention can also be synthesized using a modified nucleotide such as the thiophosphate type (P=O in phosphate linkage replaced with P=S), and 2'-O-methyl type which are stable to decomposing enzymes. Other important factors for the designing of antisense nucleic acid include increases in water-solubility and cell membrane permeability and the like; these can also be cleared by choosing appropriate dosage forms such as those using liposome or microspheres.

The length of antisense nucleic acid is not subject to limitation, as long as the antisense nucleic acid is capable of specifically hybridizing to the transcription product of the NCS protein gene; It may be of a sequence complementary to a sequence of about 15 bases for the shortest, or the entire sequence of the mRNA (initial transcription product) for the longest. Considering the ease of synthesis, antigenicity and other issues, for example, oligonucleotides consisting of about 15 nucleotides or more, preferably about 15 to about 30 nucleotides, can be mentioned.

The target sequence for the antisense nucleic acid may be any sequence that inhibits the translation of the NCS protein gene or a functional fragment thereof by being hybridized to the antisense nucleic acid, and may be the entire sequence or a partial sequence of mRNA, or the intron portion of the initial transcription product; when an oligonucleotide is used as the antisense nucleic acid, it is desirable that the target sequence be located in a position from the 5' terminus of the mRNA of the NCS protein gene to the C terminus of the coding region thereof.

Furthermore, the antisense nucleic acid may be not only capable of hybridizing to a transcription product of the NCS protein gene to inhibit its translation, but also binding to the NCS protein gene in the form of double-stranded DNA to form a triple-strand (triplex) and inhibit the transcription to mRNA.

Another example of the substance that suppresses the expression of the NCS protein gene is a ribozyme capable of specifically cleaving a transcription product, specifically mRNA or initial transcription product, of the NCS protein gene in the coding region (including the intron portion in the case of initial transcription product). "A ribozyme" refers to an RNA possessing enzymatic activity to cleave nucleic acids. Because it has recently been shown that an oligo-DNA having the nucleotide sequence of the enzymatic activity site also possesses nucleic acid cleavage activity, this term is herein used to mean a concept including DNA, as long as it possesses sequence specific nucleic acid cleavage activity. The most versatile ribozyme is self-splicing RNA, found in infectious RNAs such as those of viroid and virosoid; this self-splicing RNA is known as hammerhead type, hairpin type and the like. When ribozyme is used in the form of an expression vector comprising a DNA that encodes the same, a hybrid ribozyme wherein a sequence modified from tRNA is further linked to promote localization to cytoplasm may be used [Nucleic Acids Res., 29(13): 2780-2788 (2001)].

A still another example of the substance that suppresses the expression of the NCS protein gene is a decoy nucleic acid. A decoy nucleic acid refers to a nucleic acid molecule that mimics a region to which a transcription regulatory factor binds; the decoy nucleic acid, which is the substance that suppresses the expression of the NCS protein gene, can be a nucleic acid molecule that mimics a region to which a transcription activation factor for the NCS protein gene binds.

Examples of the decoy nucleic acid include oligonucleotides modified to make them unlikely to undergo degradation in a body, such as oligonucleotides having a thiophosphoric diester bond wherein an oxygen atom in the phosphoric diester bond moiety is replaced with a sulfur atom (S-oligo), and oligonucleotides wherein the phosphoric diester bond is replaced with an uncharged methyl phosphate group, and the like. Although the decoy nucleic acid may completely match with the region to which a transcription activation factor binds, the degree of matching may be such that the binding ability of the decoy nucleic acid to the transcription activation factor for the NCS protein gene is retained. The length of the decoy nucleic acid is not subject to limitation, as long as the transcription activation factor binds thereto. The decoy nucleic acid may comprise a repeat of the same region.

Still another example of the substance that suppresses the expression of the NCS protein gene is a double-stranded oligo-RNA, i.e. siRNA, which is complementary to a partial sequence (including the intron portion in the case of an initial transcription product) in the coding region of a transcription product, specifically, the mRNA or initial transcription product, of the NCS protein gene. It has been known that so-called RNA interference (RNAi), which is a phenomenon that if short double stranded RNA is introduced into cells, mRNA complementary to the RNA is degraded, occurs in nematodes, insects, plants and the like; recently, it has been found that this phenomenon also occurs in animal cells [Nature, 411(6836): 494-498 (2001)], which is drawing attention as an alternative technique to ribozymes. The siRNA used may be internally synthesized as described below, and a commercially available one may be used.

The antisense oligonucleotide and ribozyme can be prepared by determining the target sequence for a transcription product, specifically the mRNA or initial transcription product, of the NCS protein gene on the basis of the cDNA sequence or genomic DNA sequence of the NCS protein gene, and by synthesizing a sequence complementary thereto using a commercially available automated DNA/RNA synthesizer (Applied Biosystems Company, Beckman Instruments Company and the like). A decoy nucleic acid and siRNA can be prepared by synthesizing a sense strand and an antisense strand in an automated DNA/RNA synthesizer, respectively, denaturing the strands in an appropriate annealing buffer solution at about 90 to about 95° C. for about 1 minute, and then annealing the strands at about 30 to about 70° C. for about 1 to about 8 hours. A longer double-stranded polynucleotide can be prepared by synthesizing a complementary oligonucleotide chain in alternative overlaps, annealing them, and then ligating them with ligase.

Another example of the substance that suppresses the expression of the NCS protein gene is an antibody against the NCS protein. The antibody may be a polyclonal antibody or a monoclonal antibody, and can be prepared by a well-known immunological technique. The antibody may also be a fragment of an antibody (e.g., Fab, F(ab')$_2$), or a recombinant antibody (e.g., single-chain antibody). Furthermore, the nucleic acid that encodes the antibody (one functionally linked to a nucleic acid having promoter activity) is also preferable as the substance that suppresses the expression of the NCS protein gene.

The polyclonal antibody can be acquired by, for example, subcutaneously or intraperitoneally administering the NCS protein or a fragment thereof (as required, may be prepared as a complex crosslinked to a carrier protein such as bovine serum albumin or KLH (keyhole limpet hemocyanin)) as the antigen, along with a commercially available adjuvant (e.g., Freund's complete or incomplete adjuvant) to an animal about 2 to 4 times at intervals of 2 to 3 weeks (the antibody titer of partially drawn serum has been determined by a known antigen-antibody reaction and its elevation has been confirmed in advance), collecting whole blood about 3 to about 10 days after final immunization, and purifying the antiserum. As the animal to receive the antigen, mammals such as rats, mice, rabbits, goat, guinea pigs, and hamsters can be mentioned.

The monoclonal antibody can be prepared by, for example, a cell fusion method (e.g., Takeshi Watanabe, Saibou Yugouhou No Genri To Monokuronaru Koutai No Sakusei, edited by Akira Taniuchi and Toshitada Takahashi, "Monokuronaru Koutai To Gan—Kiso To Rinsho—", pages 2-14, Science Forum Shuppan, 1985). For example, the factor is administered subcutaneously or intraperitoneally along with a commercially available adjuvant to a mouse 2 to 4 times, and about 3 days after final administration, the spleen or lymph nodes are collected, and leukocytes are collected. These leukocytes and myeloma cells (e.g., NS-1, P3X63Ag8 and the like) are cell-fused to obtain a hybridoma that produces a monoclonal antibody against the factor. This cell fusion may be performed by the PEG method [J. Immunol. Methods, 81(2): 223-228 (1985)], or by the voltage pulse method [Hybridoma, 7(6): 627-633 (1988)]. A hybridoma that produces the desired monoclonal antibody can be selected by detecting an antibody that binds specifically to the antigen from the culture supernatant using a widely known EIA or RIA method and the like. Cultivation of the hybridoma that produces the monoclonal antibody can be performed in vitro, or in vivo such as in mouse or rat ascitic fluid, preferably in mouse ascitic fluid, and the antibody can be acquired from the culture supernatant of the hybridoma and the ascitic fluid of the animal, respectively.

However, in view of therapeutic efficacy and safety in humans, the antibody of the present invention may be a chimeric antibody or a humanized or human type antibody. The chimeric antibody can be prepared with reference to, for example, "Jikken Igaku (extra issue), Vol. 6, No. 10, 1988", Japanese Patent Kokoku Publication No. HEI-3-73280 and the like. The humanized antibody can be prepared with reference to, for example, Japanese Patent Kohyo Publication No. HEI-4-506458, Japanese Patent Kokai Publication No. SHO-62-296890 and the like. The human antibody can be prepared with reference to, for example, "Nature Genetics, Vol. 15, p. 146-156, 1997", "Nature Genetics, Vol. 7, p. 13-21, 1994", Japanese Patent Kohyo Publication No. HEI-4-504365, International Patent Application Publication No. WO94/25585, "Nikkei Science, June issue, pp. 40 to 50, 1995", "Nature, Vol. 368, pp. 856-859, 1994", Japanese Patent Kohyo Publication No. HEI-6-500233 and the like.

The substance that regulates the expression or function of the NCS protein gene can also be a substance that suppresses a function of the NCS protein gene.

Although the substance that suppresses a function of the NCS protein gene is not subject to limitation, as long as it is capable of interfering with an action of the NCS protein gene, it is important that the substance be capable of specifically acting on the target molecule to minimize the adverse effect on other genes and proteins. Examples of the substance that specifically suppresses a function of the NCS protein gene include a dominant negative mutant of the NCS protein and a nucleic acid that encodes the mutant (one functionally linked to a nucleic acid having promoter activity).

A dominant negative mutant of the NCS protein refers to a mutant having the activity thereof reduced as a result of mutagenesis to the NCS protein. The dominant negative mutant can indirectly inhibit the activity of natural NCS protein by competing with the protein. The dominant negative mutant can be prepared by introducing a mutation to a nucleic acid that encodes the NCS protein gene. Examples of, the mutation include amino acid mutations (e.g., deletion, substitution, and addition of one or more amino acids) in a site of EF hand motif, myristoylation site and sites other than these sites that result in a decrease in the function responsible for the sites. The mutation can be introduced by a method known per se using PCR or a commonly known kit.

The substance that regulates the function of NCS protein also includes the compounds described above and salts thereof.

Provided that the substance that suppresses the expression of the NCS protein gene is a nucleic acid molecule, the regulator of the present invention can have an expression vector that encodes the nucleic acid molecule as the active ingredient thereof. The expression vector is an oligonucleotide or polynucleotide that encodes the above-described nucleic acid molecule, and must be functionally linked to a promoter capable of exhibiting promoter activity in the cells of the recipient mammal. Any promoter capable of functioning in the recipient mammal can be used; examples include viral promoters such as the SV40-derived early promoter, cytomegalovirus LTR, Rous sarcoma virus LTR, MoMuLV-derived LTR, and adenovirus-derived early promoter, and mammalian structural protein gene promoters such as the β-actin gene promoter, PGK gene promoter, and transferrin gene promoter, and the like.

The expression vector preferably comprises a transcription termination signal, that is, a terminator region, downstream of the oligo (poly)nucleotide that encodes the nucleic acid molecule. The expression vector may further comprise a selection marker gene for selecting transformant cells (genes that confer resistance to drugs such as tetracycline, ampicillin, kanamycin, hygromycin, and phosphinothricin, gene that compensate for auxotrophic mutation, and the like).

Although the basic backbone vector used as the expression vector is not subject to limitation, vectors suitable for administration to mammals such as humans include viral vectors such as retrovirus, adenovirus, adeno-associated virus, herpesvirus, vaccinia virus, poxvirus, poliovirus, Sindbis virus, and Sendai virus. Adenovirus has advantageous features, including the very high efficiency of gene introduction and possibility of introduction to non-dividing cells. Because incorporation of the introduced gene to host chromosome is very rare, gene expression is transient, usually lasting for about 4 weeks. In view of the sustainability of therapeutic effect, it is also preferable to use adeno-associated virus, which offers relatively high gene transduction efficiency, which can be introduced to non-dividing cells, and which can be incorporated in chromosomes via a inverted terminal repeat sequence (ITR).

The substance that regulates the expression or function of the NCS protein can also be the NCS protein-targeting drug described above, and can be, for example, atorvastatin, pimozide, bifonazole, flunarizine, fendiline, chloperastine, bepridil, raloxifene hydrochloride, benzbromarone, prazepam, clotiazepam, suloctidil, benzethonium, bicaltamide, benzthiazide, minaprine, trifluoperazine, chlorprothixene, pimethixene, flupentixol, clofazimine, loxapine, rescinnamine, syrosingopine, dihydroergocornine mesylate, dihydro-α-ergocryptine mesylate, dihydro-β-ergocryptine mesylate, dihydroergocristine mesylate or stanozolol, or a derivative thereof capable of binding to the NCS protein (described later), or a salt thereof.

Regulator I can comprise any carrier, for example, a pharmaceutically acceptable carrier, in addition to a substance that regulates the expression or function of the NCS protein gene.

Examples of the pharmaceutically acceptable carrier include, but are not limited to, excipients such as sucrose, starch, mannitol, sorbitol, lactose, glucose, cellulose, talc, calcium phosphate, and calcium carbonate; binders such as cellulose, methylcellulose, hydroxypropylcellulose, polypropylpyrrolidone, gelatin, gum arabic, polyethylene glycol, sucrose, and starch; disintegrants such as starch, carboxymethylcellulose, hydroxypropylstarch, sodium-glycolstarch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin ammonium salt, glycine, and orange powder; preservatives such as sodium benzoate, sodium hydrogen sulfite, methyl paraben, and propyl paraben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao fat, polyethylene glycol, and kerosene, and the like.

Preparations suitable for oral administration include liquids comprising an effective amount of substance dissolved in a diluent such as water, physiological saline, or orange juice, capsules, sachets or tablets comprising an effective amount of substance in the form of solid or granules, suspensions comprising an effective amount of substance suspended in an appropriate dispersant, emulsions comprising a solution of an effective amount of substance dispersed in an appropriate dispersant and the like.

Preparations suitable for parenteral administration (e.g., subcutaneous injection, intramuscular injection, topical injection, intraperitoneal injection, and the like) include aqueous and non-aqueous isotonic sterile injection liquids, which may comprise an antioxidant, a buffer solution, a bacteriostatic agent, an isotonizing agent and the like. Other examples are aqueous and non-aqueous sterile suspensions, which may comprise a suspending agent, a solubilizer, a thickening agent, a stabilizer, an antiseptic and the like. The preparation can be included in a container in a unit dose or multiple doses like an ampoule or vial. It is also possible to lyophilize the active ingredient and a pharmaceutically acceptable carrier and preserve them in a state that only requires dissolving or suspending in a suitable sterile vehicle immediately before use.

The dose of regulator I varies depending on the activity and kind of the active ingredient, severity of the disease, the animal species to be the administration subject, drug acceptability, body weight and age of the administration subject, and the like, it is generally about 0.001 to about 500 mg/kg a day for an adult based on the amount of the active ingredient.

Regulator I enables the regulation, for example, suppression or promotion, of an action associated with NCS protein-targeting drug. Hence, regulator I is useful for the prophylaxis and treatment of a disease associated with NCS protein-targeting drug, and as an investigational reagent for the disease, and the like.

3.2. Regulator of a Function Associated with the NCS Protein Gene (Regulator II)

The present invention provides a regulator of a function associated with the NCS protein gene, which comprises NCS protein-targeting drug.

This regulator is optionally abbreviated as "regulator II."

The NCS protein-targeting drug can be as described above, and can be, for example, atorvastatin, pimozide, bifonazole, flunarizine, fendiline, chloperastine, bepridil, raloxifene hydrochloride, benzbromarone, prazepam, clotiazepam, suloctidil, benzethonium, bicaltamide, benzthiazide, minaprine, trifluoperazine, chlorprothixene, pimethixene, flupentixol, clofazimine, loxapine, rescinnamine, syrosingopine, dihydroergocornine mesylate, dihydro-α-ergocryptine mesylate, dihydro-β-ergocryptine mesylate, dihydroergocristine mesylate or stanozolol, or a derivative thereof capable of binding to the NCS protein (described later), or a salt thereof.

Regulator II can comprise any carrier, for example, a pharmaceutically acceptable carrier, in addition to NCS protein-targeting drug. The dose of regulator II is the same as that of regulator I.

Regulator II enables the regulation, for example, suppression or promotion, of a function associated with the NCS protein gene. Hence, regulator II is useful for the prophylaxis and treatment of a disease associated with the NCS protein gene, and as an investigational reagent for the disease, and the like.

4. Derivative Production Method and Product Obtained by the Method

The present invention provides methods of producing a drug derivative, comprising derivatizing a drug so as to be able to regulate the expression or function of the NCS protein gene, and the products obtained thereby. The production methods of the present invention can be roughly divided into a method of producing a drug derivative capable of regulating an action associated with NCS protein-targeting drug (e.g., central nervous action), and a method of producing a drug derivative capable of regulating a function associated with the NCS protein gene, from the viewpoint of the kinds of action and function of the derivative obtained. The individual production methods are hereinafter described in detail.

4.1. Production Method of a Drug Derivative Capable of Regulating an Action Associated with NCS Protein-Targeting Drug (Production Method I)

The present invention provides a method of producing a drug derivative capable of regulating an action associated with NCS protein-targeting drug, comprising derivatizing a drug so as to be able to regulate the expression or function of the NCS protein gene.

This production method is optionally abbreviated as "production method I."

Derivatization means that a compound obtained by replacing a particular atom or group in a lead compound with another atom or group, or a compound obtained by subjecting a lead compound to an addition reaction, is virtually or actually synthesized. For example, the lead compound can be an NCS protein-targeting drug. The NCS protein-targeting drug is not particularly limited, and can be, for example, statin drugs having anti-central nervous action.

The derivatization of NCS protein-targeting drug can be performed so that the regulatory capability for the expression or function of the NCS protein gene is retained, and as required, in view of other properties of the derivative obtained, such as hydrophilicity/liphophilicity, stability, dynamics, bioavailability, toxicity and the like. The derivatization of NCS protein-targeting drug can be performed so that, for example, the regulatory capability for the expression or function of the NCS protein gene can be increased. The derivatization of NCS protein-targeting drug can also be performed so that a function associated with the NCS protein gene can be regulated.

The derivatization of NCS protein-targeting drug such that the regulatory capability for the expression or function of the NCS protein gene is retained can be performed on the basis of, for example, SBDD (structure-based drug design: SBDD) and CADD (computer-aided drug design). Examples of the design include virtual screening, de novo design, pharmacophore analysis, QSAR (quantitative structure activity relationship) and the like. If information on the steric structure of the protein itself or the target site of the protein is required during such designing, information on the steric structure is used provided that the steric structure is known by a structural analytical technique such as NMR, X-ray crystallographic analysis, or synchrotron radiation analysis. If the steric structure is unknown, information obtained by a structural predictive method such as the homology method or the threading method is used. In virtual screening, a program known per se is used; examples of the program include DOCK (Kuntz, I. D. et al., Science, 1992, 257, 1078), Gold (Jones, G. et al., J. Mol. Biol., 1995, 245, 43), FlexX (Rarey, M. et al., J. Mol. Biol., 1996, 261, 470), AtutoDock (Morris, G. M. et al., J. Comput. Chem., 1998, 19, 1639), ICM (Abagyan, R. A. et al., J. Comput. Chem., 1994, 15, 488) and the like.

The derivatization of NCS protein-targeting drug such that the regulatory capacity for the expression or function of the NCS protein gene is retained can also be performed on the basis of, for example, biological verification. In this case, for example, the above-described methodologies I to IV can be used. Furthermore, the above-described method such as SBDD or CADD, and biological verification may be used in combination.

A particular atom in the NCS protein-targeting drug, which is substituted for the production of derivative, is not limited as long as it is present in a lead compound and, for example, a hydrogen atom, a halogen atom (e.g., a fluorine atom, a chlorine atom, a bromine atom, an iodine atom), an oxygen atom, a sulfur atom, a nitrogen atom, a carbon atom and the like can be mentioned.

The particular group in the NCS protein-targeting drug, which is substituted for the production of derivative, is not limited as long as it is present in the NCS protein-targeting drug and may be, for example, a group having a molecular weight of 1 to 500, preferably 1 to 300, more preferably 1 to 200, most preferably 1 to 100. As the particular group, for example, an optionally substituted $C_1$-$C_8$ hydrocarbon group, an optionally substituted $C_1$-$C_8$ acyl group, an optionally substituted aromatic or non-aromatic $C_3$-$C_{14}$ hydrocarbon ring group, an optionally substituted aromatic or non-aromatic $C_3$-$C_{14}$ heterocyclic group, an amino group, an amino group mono- or di-substituted by an alkyl group having 1 to 4 carbon atoms or an acyl group having 2 to 8 carbon atoms, an amidino group, a carbamoyl group, a carbamoyl group mono- or di-substituted by an alkyl group having 1 to 4 carbon atoms, a sulfamoyl group, a sulfamoyl group mono- or di-substituted by an alkyl group having 1 to 4 carbon atoms, a carboxyl group, an alkoxycarbonyl group having 2 to 8 carbon atoms, a hydroxy group, an alkoxyl group having 1 to 6 carbon atoms and optionally substituted by 1 to 3 halogen atoms, an alkenyloxy group having 2 to 5 carbon atoms and optionally substituted by 1 to 3 halogen atoms, a cycloalkyloxy group having 3 to 7 carbon atoms, an aralkyloxy group having 7 to 9 carbon atoms, an aryloxy group having 6 to 14 carbon atoms, a thiol group, an alkylthio group having 1 to 6 carbon atoms and optionally substituted by 1 to 3 halogen atoms, an aralkylthio group having 7 to 9 carbon atoms, an arylthio group having 6 to 14 carbon atoms, a sulfo group, a cyano group, an azido group, a nitro group, a nitroso group and the like can be mentioned.

The optionally substituted $C_1$-$C_8$ hydrocarbon group may be, for example, an optionally substituted $C_1$-$C_8$ alkyl group, an optionally substituted $C_2$-$C_8$ alkenyl group or an optionally substituted $C_2$-$C_8$ alkynyl group.

The $C_1$-$C_8$ alkyl group of the optionally substituted $C_1$-$C_8$ alkyl group may be straight chain or branched chain, and preferably has 1 to 6 carbon atoms. For example, methyl, ethyl, propyl, isopropyl, butyl, isobutyl, sec-butyl, tert-butyl and the like can be mentioned.

The $C_2$-$C_8$ alkenyl group of the optionally substituted $C_2$-$C_8$ alkenyl group may be straight chain or branched chain, and preferably has 2 to 6 carbon atoms. For example, ethenyl, 1-propenyl, 2-propenyl, 2-methyl-1-propenyl, 1-butenyl, 2-butenyl, 3-butenyl and the like can be mentioned.

The $C_2$-$C_8$ alkynyl group of the optionally substituted $C_2$-$C_8$ alkynyl group may be straight chain or branched chain, and preferably has 2 to 6 carbon atoms. For example, ethynyl, 1-propynyl, 2-propynyl, 1-butynyl, 2-butynyl, 3-butynyl and the like can be mentioned.

The $C_1$-$C_8$ acyl group of the optionally substituted $C_1$-$C_8$ acyl group may be straight chain or branched chain, and preferably has 2 to 6 carbon atoms. For example, formyl, acetyl, propanoyl, butanoyl, 2-methylpropanoyl and the like can be mentioned.

The aromatic $C_3$-$C_{14}$ hydrocarbon ring group of the optionally substituted aromatic $C_3$-$C_{14}$ hydrocarbon ring group may be monocyclic, bicyclic or tricyclic, and preferably has 3 to 12 carbon atoms. For example, phenyl and naphthyl can be mentioned.

The non-aromatic $C_3$-$C_{14}$ hydrocarbon ring group of the optionally substituted non-aromatic $C_3$-$C_{14}$ hydrocarbon ring group may be saturated or unsaturated, monocyclic, bicyclic or tricyclic, and preferably has 3 to 12 carbon atoms. For example, a cycloalkyl group (e.g., cyclopropyl, cyclobutyl, cyclopentyl, cyclohexyl, cycloheptyl, cyclooctyl), a cycloalkenyl group (e.g., 2-cyclopenten-1-yl, 3-cyclopenten-1-yl, 2-cyclohexen-1-yl, 3-cyclohexen-1-yl), a cycloalkadienyl group (e.g., 2,4-cyclopentadien-1-yl, 2,4-cyclohexadien-1-yl, 2,5-cyclohexadien-1-yl) and the like can be mentioned.

The aromatic $C_3$-$C_{14}$ heterocyclic group of the optionally substituted aromatic $C_3$-$C_{14}$ heterocyclic group is a monocyclic, bicyclic or tricyclic aromatic heterocyclic group containing, as a ring-constituting atom besides carbon atoms, 1 to 5 heteroatoms selected from an oxygen atom, a sulfur atom and a nitrogen atom, and preferably has 3 to 12 carbon atoms. As examples of monocyclic aromatic $C_3$-$C_{14}$ heterocyclic group, furyl, thienyl, pyrrolyl, oxazolyl, isoxazolyl, thiazolyl, isothiazolyl, imidazolyl, pyrazolyl, oxadiazolyl, furazanyl, thiadiazolyl, triazolyl, tetrazolyl, pyridyl, pyrimidinyl, pyridazinyl, pyrazinyl, triazinyl and the like can be mentioned. As examples of bicyclic or tricyclic aromatic heterocyclic group, benzo furanyl, isobenzofuranyl, benzo[b]thienyl, indolyl, isoindolyl, 1H-indazolyl, benzimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, α-carbolinyl, β-carbolinyl, γ-carbolinyl, acrydinyl, phenoxazinyl, phenothiazinyl, phenazinyl, phenoxathiinyl, thianthrenyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like can be mentioned.

The non-aromatic $C_3$-$C_{14}$ heterocyclic group of the optionally substituted non-aromatic $C_3$-$C_{14}$ heterocyclic group is a monocyclic, bicyclic or tricyclic, saturated or unsaturated heterocyclic group containing, as a ring-constituting atom besides carbon atoms, 1 to 5 heteroatoms selected from an oxygen atom, a sulfur atom and a nitrogen atom, and preferably has 3 to 12 carbon atoms. For example, oxylanyl, azetidinyl, oxetanyl, thietanyl, pyrrolidinyl, tetrahydrofuryl, tetrahydropyranyl, morpholinyl, thiomorpholinyl, piperazinyl, pyrrolidinyl, piperidino, morpholino, thiomorpholino and the like can be mentioned.

The kind of the substituent in any group optionally substituted can be the same as the particular group in NCS protein-targeting drug (described above), which is substituted for producing the derivative.

The number of particular atoms or groups in NCS protein-targeting drug, which is substituted for producing the derivative is any number, as long as the derivative produced is capable of regulating the expression or function of the NCS protein gene, for example, as long as it is capable of binding to the NCS protein, and can be, for example, 1 to 10, preferably 1 to 5, more preferably 1 to 3, further more preferably 1 to 2, most preferably 1.

The kind of a particular atom or group used for substitution (i.e., an atom or group introduced to the substitution site) can be the same as the particular atom or group in NCS protein-targeting drug, which is substituted for producing the derivative.

The atom or group added to NCS protein-targeting drug for producing the derivative (i.e., an atom or group used in the addition reaction) is an atom permitting an addition reaction, for example, an atom such as the hydrogen atom or the halogen atom, or a group capable of acting as a nucleophile or electrophile, out of the particular atoms or groups in NCS protein-targeting drug (described above), which is substituted for producing the derivative.

The number of atoms or groups added to NCS protein-targeting drug for producing the derivative is any number, as long as the derivative produced is capable of regulating the expression or function of the NCS protein gene, for example, as long as it is capable of binding to the NCS protein, and can be, for example, less than 6, preferably less than 4, more preferably less than 2.

The production method I is useful for, for example, the development of prophylactic or therapeutic agents for diseases associated with NCS protein-targeting drug (for example, central nervous diseases), investigational reagents for the diseases, and the like.

4.2. Production Method of a Drug Derivative Capable of Regulating a Function Associated with the NCS Protein Gene (Production Method II)

The present invention provides a method of producing a drug derivative capable of regulating a function associated with the NCS protein gene, comprising derivatizing a drug so as to be able to regulate the ability of the drug to bind to NCS protein or a mutant protein thereof.

This production method is optionally abbreviated as "production method II."

The derivatization of NCS protein-targeting drug can be performed so that the binding capability for the NCS protein or a mutant protein thereof is retained, and as required, in view of other properties of the derivative obtained, such as hydrophilicity/liphophilicity, stability, dynamics, bioavailability, toxicity and the like. The derivatization of the drug can be performed so that, for example, the binding capability can be increased.

The derivatization of a drug such that the binding capability is retained can be performed on the basis of, for example, SBDD and CADD.

The derivatization of a drug such that the binding capability is retained can also be performed on the basis of, for example, biological verification. In this case, the derivatization can be performed as is similar to, for example, the above-described methodologies IV. Furthermore, the above-described method such as SBDD or CADD, and biological verification may be used in combination.

The particular atom or group in lead compound, which is substituted for producing the derivative, and the number of the atoms or groups can be the same as those described above. The particular atom or group used for substitution (i.e., the atom and group introduced to the substitution site), the atom or group added for producing the derivative (i.e., the atom or group used for additive reaction), and the number of the atoms or groups are the same as those described above.

The production method II is useful for the development of prophylactic or therapeutic agents for diseases associated with NCS protein gene, investigational reagents for the diseases, and the like.

4.3. Product Obtained by the Derivative Production Method

The present invention provides a product obtained by the above-described methods I and II.

The product provided by the above-described production method can be a derivative of an NCS protein-targeting drug, which is obtained by the production method of the present invention, and a pharmacological action regulator comprising the derivative (described above).

A product provided by the above-described production method is useful for, for example, the prophylaxis or treatment of diseases associated with NCS protein-targeting drug, or diseases associated with the NCS protein gene, or as investigational reagents for the disease, and the like.

5. Complex and Production Method Thereof

The present invention provides a complex comprising a drug and NCS protein or a mutant protein thereof.

The drug can be the above-described NCS protein-targeting drug, and includes, for example, atorvastatin, pimozide, bifonazole, flunarizine, fendiline, chloperastine, bepridil, raloxifene hydrochloride, benzbromarone, prazepam, clotiazepam, suloctidil, benzethonium, bicaltamide, benzthiazide, minaprine, trifluoperazine, chlorprothixene, pimethixene, flupentixol, clofazimine, loxapine, rescinnamine, syrosingopine, dihydroergocornine mesylate, dihydro-α-ergocryptine mesylate, dihydro-β-ergocryptine mesylate, dihydroergocristine mesylate and stanozolol, and a derivative thereof capable of binding to the NCS protein, and the like.

The present invention also provides a method of producing a complex comprising a drug and NCS protein or a mutant thereof, which comprises bringing the drug and the NCS protein or a mutant thereof into contact with each other. This contact can be performed by, for example, mixing the drug and the protein in solution.

The complex of the present invention and the production method of the complex can be useful in, for example, performing the screening methods of the present invention or the production method of the derivative of the present invention, or in cases where the complex is structurally analyzed to extensively investigate the mode of interaction between a drug and a protein, and the like.

6. Kit

The present invention provides a kit comprising a drug or a salt thereof.

In one embodiment, the kit of the present invention comprises the following (i) and (ii):
(i) a drug or a salt thereof;
(ii) NCS protein or a mutant thereof, a nucleic acid that encodes the protein, an expression vector comprising the nucleic acid, cells enabling a measurement of the expression of the NCS protein gene, or an expression vector comprising the transcription regulatory region of the NCS protein gene and a reporter gene functionally linked to the region.

Provided that the kit of the present invention comprises the protein, the protein is not in the form of a complex with the drug.

The expression vector, the cells enabling a measurement of the expression of the NCS protein gene, the transcription regulatory region of the NCS protein gene, and the reporter gene functionally linked to the region, are the same as those described above (see, e.g., "2. Screening method, and product obtained by the method").

The above-described kit of the present invention can be useful in, for example, performing the screening methods of the present invention, the production method of the derivative of the present invention, and the production method of the complex of the present invention, and the like.

7. Determination Method and Determination Kit for the Onset or Risk of Onset of Disease The present invention provides determination methods and determination kits for the onset or risk of onset of a specified disease. The determination methods and determination kits of the present invention can be roughly divided into a determination method and determination kit based on measurement of the expression level, and a determination method and determination kit based on identification of the polymorphism, from the viewpoint of the subject to be measured. Furthermore, they can be classified into a determination method and determination kit for the onset or risk of onset of a disease associated with NCS protein-targeting drug (for example, central nervous disease), and a determination method and determination kit for the onset or risk of onset of a disease associated with the NCS protein gene, from the viewpoint of the disease for which a determination of the onset or risk of onset is desired. The individual determination methods and determination kits are hereinafter described in detail.

7.1. Determination Method and Determination Kit for the Onset or Risk of Onset of Disease on the Basis of Measurement of the Expression Level of the NCS Protein Gene 7.1.1. Determination Method for the Onset or Risk of Onset of Disease Associated with NCS Protein-Targeting Drug on the Basis of Measurement of the Expression Level of the NCS Protein Gene (Determination Method I)

The present invention provides a determination method for the onset or risk of onset of a disease associated with NCS protein-targeting drug, which comprises measuring the expression level of the NCS protein gene.

This determination method is optionally abbreviated as "determination method I."

In one embodiment, determination method I comprises the following steps (a) and (b):
(a) a step for measuring the expression level of the NCS protein gene in a biological sample collected from an animal;
(b) a step for evaluating the onset or likelihood of onset of a disease associated with NCS protein-targeting drug on the basis of the expression level of the NCS protein gene.

The methodology comprising the above-described steps (a) to (b) is optionally abbreviated as "methodology V."

In step (a) of methodology V, the expression level of the NCS protein gene in a biological sample collected from an animal is measured. Although the animal is not particularly limited, mammal such as laboratory animals such as mice, rats, hamsters, guinea pigs, and rabbits, domestic animals such as swine, bovine, goat, horses, and sheep, companion animals such as dogs and cats, and primates such as monkeys, orangutans, chimpanzees, and humans can be mentioned.

The biological sample may be any sample containing a tissue expressing the NCS protein gene. The tissue expressing the NCS protein gene is as described above. The expression level of the NCS protein gene can be measured by a method known per se with a product, for example, a transcription product or translation product, of the NCS protein gene, as the subject. In step (b) of methodology V, a determination is made whether or not the animal is suffering from a disease associated with NCS protein-targeting drug on the basis of the expression level of the NCS protein gene. Specifically, first, the measured expression level of the NCS protein gene is compared with the expression level of the NCS protein gene in an animal that has not contracted the disease associated with NCS protein-targeting drug (e.g., a normal animal). This comparison of expression level is preferably performed on the basis of the presence or absence of a significant difference. The expression level of the NCS protein gene in an animal that has not contracted the disease associated with NCS protein-targeting drug can be determined by a method known per se.

Next, on the basis of the result of the comparison of the expression level of the NCS protein gene, a judgement is made whether or not the animal is possibly suffering from a disease associated with NCS protein-targeting drug, or is likely or unlikely to suffer from the disease in the future. It is known that in animals that have contracted a particular disease, a change in the expression of the gene associated with the disease is often observed. It is also known that prior to the onset of a particular disease, a change in the expression of the particular gene is often observed. Hence, by analyzing the expression level of the NCS protein gene, it is possible to determine the onset or likelihood of onset of the disease associated with NCS protein-targeting drug.

Determination method I enables a determination of the presence or absence of a disease associated with NCS protein-targeting drug, or the likelihood of contracting the disease. Hence, determination method I is useful for, for example, the easy and early detection of the disease, and the like.

7.1.2. Determination Kit for the Onset or Risk of Onset of Disease Associated with NCS Protein-Targeting Drug on the Basis of Measurement of Expression Level of the NCS Protein Gene (Determination Kit I)

The present invention provides a determination kit that enables the easy conduct of determination method I.

This determination kit is optionally abbreviated as "determination kit I."

In one embodiment, determination kit I comprises the following (i) and (ii):
(i) a means capable of measuring the expression level of the NCS protein gene;
(ii) a medium recording the relationship between a disease associated with NCS protein-targeting drug and the expression level of the NCS protein gene.

The means capable of measuring the expression level of the NCS protein gene is not subject to limitation, as long as it allows a quantitation of the expression level of the NCS protein gene; for example, such means are roughly divided into means capable of quantifying NCS protein (for example, antibody, or NCS protein-targeting drug), and means capable of quantifying a transcription product of the NCS protein gene (for example, or nucleic acid probe, a pair of primers). The means may be labeled with a labeling substance. Provided that the means is not labeled with a labeling substance, the determination kit of the present invention may further comprise the labeling substance. The labeling substance is the same as described above.

Determination kit I enables a determination of the presence or absence of a disease associated with NCS protein-targeting drug, or the likelihood of contracting the disease. Hence, determination kit I is useful for, for example, the easy and early detection of the disease, and the like.

7.2. Determination Method and Determination Kit for the Risk of Onset of Disease on the Basis of Identification of Polymorphism of the NCS Protein Gene

7.2.1. Determination Method for the Risk of Onset of Disease Associated with NCS Protein-Targeting Drug on the Basis of Identification of Polymorphism of the NCS Protein Gene (Determination Method II)

The present invention provides a determination method for the risk of onset of a disease associated with NCS protein-targeting drug; which comprises identifying the polymorphism of the NCS protein gene.

This determination method is optionally abbreviated as "determination method II."

In one embodiment, determination method II comprises the following steps (a) and (b):
(a) a step for identifying the polymorphism of the NCS protein gene in a biological sample collected from an animal;
(b) a step for evaluating the likelihood of the onset of a disease associated with NCS protein-targeting drug on the basis of the type of polymorphism.

The methodology comprising the above-described steps (a) to (b) is optionally abbreviated as "methodology VI."

In step (a) of methodology VI, the type of polymorphism of the NCS protein gene is identified in a biological sample collected from an animal. The animal is the same as described above.

Although the biological sample used may be one described with respect to methodology V above, this methodology VI enables the use of any tissue containing genomic DNA, such as hair, nails, skin or mucosa, as the biological sample. In view of the ease of procurement, burden on the human body and the like, the biological sample is preferably a sample of hair, nails, skin, mucosa, blood, plasma, serum, saliva and the like.

A polymorphism of the NCS protein gene means a mutation found at a frequency in the nucleotide sequence of the genomic DNA comprising the NCS protein gene in a certain population, and can be one or more DNA substitutions, deletions, or additions (e.g., SNP, haplotype) in the genomic DNA comprising the NCS protein gene, and a repeat, inversion, translocation and the like of the genomic DNA. Various types of polymorphism of the NCS protein gene are registered with known databases, for example, H-Inv DB and the like. The type of polymorphism of the NCS protein gene used in this determination method is a mutation in a nucleotide sequence whose frequency differs between animals suffering from a disease associated with NCS protein-targeting drug and non-suffering animals, out of all types of polymorphism in the NCS protein gene, and can be, for example, one that alters the expression of the NCS protein gene or alters a function associated with the NCS protein gene (e.g., the ability of NCS protein to bind with NCS protein-targeting drug). Such types of polymorphism can be determined by a method known per se such as linkage analysis.

The identification of the type of polymorphism can be performed by a method known per se. For example, the RFLP (restriction fragment length polymorphism) method, the PCR-SSCP (single-stranded DNA conformation polymorphism) analysis method, the ASO (allele specific oligonucleotide) hybridization method, the TaqMan PCR method, the invader method and the like can be used.

In step (b) of methodology VI, a determination of the likelihood of contracting a disease associated with NCS protein-targeting drug in an animal is made on the basis of the type of polymorphism. It is known that animals susceptible to a particular disease often have a particular type of polymorphism in the gene associated with the disease. Hence, it is possible to determine the likelihood of the onset of a disease associated with NCS protein-targeting drug by polymorphism analysis.

Determination method II enables a determination of the likelihood of contracting a disease associated with NCS protein-targeting drug (e.g., a central neurological disease). Hence, determination method II is useful for the provision of an incentive for improving one's lifestyle for the purpose of preventing the disease, and the like.

7.2.2. Determination Kit for the Risk of Onset of Disease Associated with NCS Protein-Targeting Drug on the Basis of Identification of Polymorphism of the NCS Protein Gene (Determination Kit II)

The present invention also provides a determination kit that enables the easy conduct of determination method II.

This determination kit is optionally abbreviated as "determination kit II."

In one embodiment, determination kit II comprises the following (i) and (ii):
(i) a means capable of identifying the polymorphism of the NCS protein gene (for example, nucleic acid probe, or a pair of primers);
(ii) a medium recording the relationship between a disease associated with an NCS protein gene and the polymorphism of the NCS protein gene.

Determination kit II enables a determination of the likelihood of contracting a disease associated with NCS protein-targeting drug (e.g., a central neurological disease). Hence, determination kit II is useful for the provision of an incentive for improving one's lifestyle for the purpose of preventing the disease and the like.

7.2.3. Method of Determining the Risk of Onset of Disease Associated with the NCS Protein Gene on the Basis of Identification of Polymorphism of the NCS Protein Gene (Determination Method III)

The present invention provides a determination method for the risk of onset of a disease associated with the NCS protein gene, which comprises identifying the polymorphism of the NCS protein gene.

This determination method is optionally abbreviated as "determination method III."

In one embodiment, determination method III comprises the following steps (a) and (b):
(a) a step for determining the type of the polymorphism of the NCS protein gene in a biological sample collected from an animal;
(b) a step for evaluating the likelihood of the onset of a disease associated with the NCS protein gene on the basis of the type of polymorphism.

In determination method III, the type of polymorphism used to determine the risk of onset alters the ability of the NCS protein gene to bind to an NCS protein-targeting drug. Such a type of polymorphism can be determined by a method known per se such as binding assay.

The methodology comprising steps (a) and (b) above in determination method III is the same as methodology VI except for the type of polymorphism of the NCS protein gene to be identified.

Determination method III enables a determination of the likelihood of contracting a disease associated with the NCS protein gene. Hence, determination method III is useful for the provision of an incentive for improving one's lifestyle for the purpose of preventing the disease, and the like.

7.2.4. Determination Kit for the Risk of Onset of Disease Associated with the NCS Protein Gene on the Basis of Identification of Polymorphism of the NCS Protein Gene (Determination Kit III)

The present invention also provides a determination kit that enables the easy conduct of determination method III.

This determination kit is optionally abbreviated as "determination kit III."

In one embodiment, determination kit III comprises the following (i) and (ii):
(i) a means capable of identifying the polymorphism of the NCS protein gene;
(ii) a medium recording the relationship between a disease associated with the NCS protein gene and the polymorphism of the NCS protein gene.

In determination kit III, the type of polymorphism used to determine the risk of onset is one that alters the ability of NCS protein to bind with NCS protein-targeting drug. Such a type of polymorphism can be determined by a method known per se such as binding assay.

The constituents of determination kit III are the same as those of determination kit II except for the type of polymorphism of the NCS protein gene to be identified.

Determination kit III enables a determination of the likelihood of contracting a disease associated with the NCS protein gene. Hence, determination kit III is useful for the provision of an incentive for improving one's lifestyle for the purpose of preventing the disease, and the like.

8. Determination Method and Determination Kit for Susceptibility to Drugs

The present invention provides determination methods and determination kits for susceptibility to a drug. The determination methods and determination kits of the present invention can be roughly divided into determination methods and determination kits based on measurement of expression level, and determination methods and determination kits based on identification of polymorphism. Furthermore, they are classified into determination methods and determination kits for a disease associated with NCS protein-targeting drug, and determination methods and determination kits for a disease associated with the NCS protein gene, from the viewpoint of a disease for which a determination of susceptibility is desired. The individual determination methods and determination kits are hereinafter described in detail.

8.1. Determination Method and Determination Kit for Susceptibility to Drugs on the Basis of Measurement of the Expression Level of the NCS Protein Gene 8.1.1. Determination Method for Susceptibility to NCS Protein-Targeting Drug in Disease Associated with NCS Protein-Targeting Drug on the Basis of Measurement of the Expression Level of the NCS Protein Gene (Determination Method IV)

The present invention provides a determination method for susceptibility to NCS protein-targeting drug in a disease associated with NCS protein-targeting drug, which comprises measuring the expression level of the NCS protein gene.

This determination method is optionally abbreviated as "determination method IV."

In one embodiment, determination method IV comprises the following steps (a) and (b):
(a) a step for measuring the expression level of the NCS protein gene in a biological sample collected from an animal;
(b) a step for predicting the effect of an NCS protein-targeting drug on the basis of the expression level of the NCS protein gene.

The methodology comprising the above-described steps (a) to (b) is optionally abbreviated as "methodology VII."

Step (a) of methodology VII is the same as step (a) of methodology V.

In step (b) of methodology VII, the possible effect of an NCS protein-targeting drug on animals is evaluated on the basis of the expression level of the NCS protein gene. Specifically, first, the measured expression level of the NCS protein gene is checked against data on the correlation between the expression level of the NCS protein gene and susceptibility to the NCS protein-targeting drug. The correlation between the expression level of the NCS protein gene and susceptibility to the NCS protein-targeting drug can be determined by a method known per se.

Next, from the result of the comparison, susceptibility to the NCS protein-targeting drug is estimated. It is considered that in animals expressing the NCS protein gene at high levels, their susceptibility to the drug is high (or low), and that in animals expressing the gene at low levels, their susceptibility is low (or high). Hence, it is possible to determine the susceptibility of an animal to the NCS protein-targeting drug by analyzing the expression level of the NCS protein gene. For example, the likelihood or unlikelihood of obtainment of desired effect of the drug, or the probability of onset of adverse effect of a drug, can be determined.

Determination method IV enables a determination of susceptibility to NCS protein-targeting drug. Hence, determination method IV is useful for, for example, the evaluation of an action of NCS protein-targeting drug on a particular animal, and the like.

8.1.2. Determination Kit for the Onset or Risk of Onset of Disease Associated with NCS Protein-Targeting Drug on the Basis of Measurement of Expression Level of the NCS Protein Gene (Determination Kit IV)

The present invention provides a determination kit that enables the easy conduct of determination method IV.

This determination kit is optionally abbreviated as "determination kit IV."

In one embodiment, determination kit IV comprises the following (i) and (ii):
(i) a means capable of measuring the expression level of the NCS protein gene;
(ii) a medium recording the relationship between the effect of NCS protein-targeting drug and the expression level of the NCS protein gene.

The constituents of determination kit IV are the same as those of determination kit I except medium (ii).

Determination kit IV enables the easy determination of susceptibility to NCS protein-targeting drug. Hence, determination method IV is useful for, for example, the evaluation of an action of NCS protein-targeting drug on a particular animal, and the like.

8.2. Determination Method and Determination Kit for Susceptibility to NCS Protein-Targeting Drug on the Basis of Identification of Polymorphism of the NCS Protein Gene 8.2.1. Determination Method for Susceptibility to NCS Protein-Targeting Drug in Disease Associated with NCS Protein-Targeting Drug on the Basis of Identification of Polymorphism of the NCS Protein Gene (Determination Method V)

The present invention provides a determination method for susceptibility to NCS protein-targeting drug in a disease associated with NCS protein-targeting drug, which comprises identifying the polymorphism of the NCS protein gene.

This determination method is optionally abbreviated as "determination method V."

In one embodiment, determination method V comprises the following steps (a) and (b):
(a) a step for identifying the polymorphism of the NCS protein gene in a biological sample collected from an animal;
(b) a step for predicting the effect of NCS protein-targeting drug in a disease associated with the NCS protein gene on the basis of the presence or absence of a particular type of polymorphism.

The methodology comprising the above-described steps (a) to (b) is optionally abbreviated as "methodology VIII."

Step (a) of methodology VIII is the same as step (a) of methodology VI.

In step (b) of methodology VIII, the effect of NCS protein-targeting drug in a disease associated with NCS protein-targeting drug is evaluated on the basis of the type of polymorphism of the NCS protein gene. Specifically, first, the identified type of polymorphism of the NCS protein gene is checked against data on the correlation between the type of polymorphism of the NCS protein gene and susceptibility to NCS protein-targeting drug in a disease associated with NCS protein-targeting drug. This correlation can be determined by a method known per se.

Next, from the result of the comparison, susceptibility to NCS protein-targeting drug in a disease associated with NCS protein-targeting drug is estimated. It is known that in animals that are highly susceptible to a drug, a particular type of polymorphism is often observed in the NCS protein gene. Hence, it is possible to determine the susceptibility of an animal to NCS protein-targeting drug by analyzing polymorphism. For example, the likelihood or unlikelihood of obtainment of desired effect of the drug, or the probability of onset of adverse reaction of a drug, can be determined.

Determination method V enables the easy determination of susceptibility to NCS protein-targeting drug in a disease associated with NCS protein-targeting drug (for example, central nervous disease). Hence, determination method V is useful for, for example, the evaluation of an action of NCS protein-targeting drug in a disease associated with NCS protein-targeting drug, and the like.

8.2.2. Determination Kit for Susceptibility to NCS Protein-Targeting Drug in Disease Associated with NCS Protein-Targeting Drug on the Basis of Identification of Polymorphism of the NCS Protein Gene (Determination Kit V)

The present invention also provides a determination kit that enables the easy conduct of determination method V.

This determination kit is optionally abbreviated as "determination kit V."

In one embodiment, determination kit V comprises the following (i) and (ii):
(i) a means capable of identifying the polymorphism of the NCS protein gene;
(ii) a medium recording the relationship between the effect of NCS protein-targeting drug and the polymorphism of the NCS protein gene.

The constituents of determination kit V are the same as those of determination kit II except the medium (ii).

Determination kit V enables a determination of susceptibility to NCS protein-targeting drug in a disease associated with NCS protein-targeting drug (for example, central nervous disease). Hence, determination kit V is useful for, for example, the evaluation of an action of NCS protein-targeting drug in a disease associated with NCS protein-targeting drug, and the like.

8.2.3. Determination Method for Susceptibility to NCS Protein-Targeting Drug in Disease Associated with the NCS Protein Gene on the Basis of Identification of Polymorphism of the NCS Protein Gene (Determination Method VI)

The present invention provides a determination method for susceptibility to NCS protein-targeting drug in a disease associated with the NCS protein gene, which comprises identifying the polymorphism of the NCS protein gene.

This determination method is optionally abbreviated as "determination method VI."

In one embodiment, determination method VI comprises the following steps (a) and (b):
(a) a step for determining the type of polymorphism of the NCS protein gene in a biological sample collected from an animal;
(b) a step for predicting the effect of NCS protein-targeting drug in a disease associated with the NCS protein gene on the basis of the presence or absence of a particular type of polymorphism.

In this determination method, the type of polymorphism used to determine the susceptibility is one that alters the ability of NCS protein to bind with NCS protein-targeting drug. The type of polymorphism can be determined by a method known per se such as binding assay. Animals having a target gene comprising the type of polymorphism that potentiates or reduces the binding ability to the drug are thought to be highly (or poorly) susceptible to the drug; animals having a target gene comprising a type of polymorphism that reduces the binding ability are considered to be less (or more) susceptible. Hence, the susceptibility of an animal to NCS protein-targeting drug can be determined by analyzing such a type of polymorphism.

The methodology comprising steps (a) and (b) above in determination method VI is the same as methodology VIII except for the type of polymorphism of the NCS protein gene to be identified.

Determination method VI enables the easy determination of susceptibility to NCS protein-targeting drug in a disease associated with NCS protein-targeting drug. Hence, determination method VI is useful for, for example, the evaluation of an action of NCS protein-targeting drug in a disease associated with NCS protein-targeting drug, and the like.

8.2.4. Determination Kit for the Risk of Onset of Disease Associated with the NCS Protein Gene on the Basis of Identification of Polymorphism of the NCS Protein Gene (Determination Kit VI)

The present invention also provides a determination kit that enables the easy conduct of determination method VI.

This determination kit is optionally abbreviated as "determination kit VI."

In one embodiment, determination kit VI comprises the following (i) and (ii):
(i) a means capable of identifying the polymorphism of the NCS protein gene;
(ii) a medium recording the relationship between a disease associated with the NCS protein gene and the polymorphism of the NCS protein gene.

In determination kit VI, the type of polymorphism used to determine the risk of onset is one that alters the ability of NCS protein to bind with NCS protein-targeting drug. Such a type of polymorphism can be determined by a method known per se such as binding assay.

The constituents of determination kit VI are the same as those of determination kit V except for the type of polymorphism of the NCS protein gene to be identified.

Determination kit VI enables a determination of susceptibility to NCS protein-targeting drug in a disease associated with NCS protein-targeting drug. Hence, determination kit VI is useful for, for example, the evaluation of an action of NCS protein-targeting drug in a disease associated with NCS protein-targeting drug, and the like.

The disclosures in all publications mentioned herein, including patents and patent application specifications, are incorporated by reference herein to the extent that all of them have been given expressly.

EXAMPLES

The present invention is hereinafter described in more detail by means of the following examples, which, however, are not to be construed as limiting the present invention.

Reference Example 1

Method of Expressing Proteins from Human Full-Length cDNA Clone

BP-reaction was performed on human full-length cDNA clone and the cloning vector Gateway pDONR201 by the PCR cloning method using the Invitrogen Gateway system to yield an entry clone. LR-reaction was performed on this entry clone with the destination vector pDEST17 (Gateway System) and LR Clonase at 25° C. for 60 minutes to yield an expression plasmid. *Escherichia coli* competent cell BL21star(DE3)pLysS were transformed with this expression plasmid, a clone incorporating the expression vector was selected, and a frozen stock was prepared. The transformant was inoculated into LB medium and precultured, after which it was transferred into SB medium and cultured to induce the expression of IPTG, and the cells were stored frozen.

Reference Example 2

Method of Purifying the Expressed Protein of Human Full-Length cDNA Clone

A human full-length cDNA clone was expressed as a protein with an N-terminal His tag. This clone was purified using BioRobot 8000 (Qiagen) or ACTA Crystal (Amersham). In the purification with BioRobot 8000, the expression-induced frozen stock cells in Reference Example 1 was thawed and lysed with lysozyme, after which the cells were affinity-purified using Ni-NTA Superflow 96 BioRobot Kit (Qiagen). In the purification with ACTA Crystal, affinity purification using a HisTrap HP column was followed by gel filtration purification using the Gel Filtration Column HiLoad 16/60 or a 10/30 Superdex 75 prep grade column. The purified fraction was used for interaction analysis after being subjected to SDS-PAGE to verify the estimated molecular weight and purity.

Reference Example 3

Figure 2:
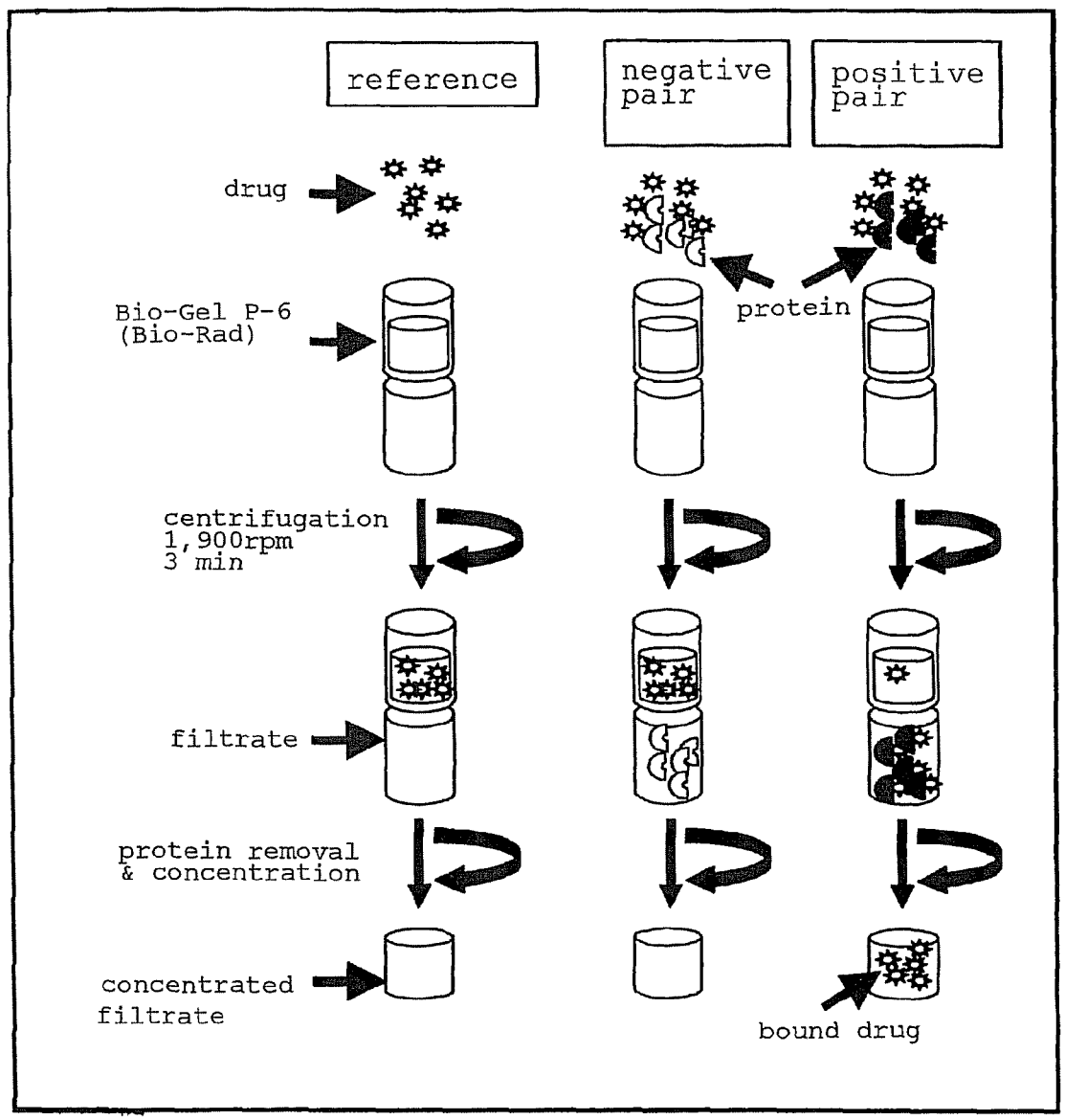
FIG. 2 is a schematic diagram showing a SEC interaction analysis using a spin column.

Method of Analyzing Human Protein-Drug Interactions Using Size Exclusion Chromatography To analyze the interactions between commonly used drugs and proteins expressed from human full-length cDNA clones while keeping both the proteins and the compounds in non-modified, non-immobilized state, size exclusion chromatography (SEC) and mass analysis were used in combination (FIGS. 1, 2). The specific procedures are shown below.

Step 1

A solution of a single drug or a multiplicated compound solution comprising a mixture of a plurality of drugs (e.g., 8 kinds, 16 kinds, 24 kinds) was added to the protein purified in Reference Example 2.

Step 2

The compound-protein mixture prepared in step 1 was subjected to chromatography using an SEC column, the compound and the protein were separated by SEC, and the compound that interacted with the bound compound or protein contained in the protein fraction was analyzed using a mass analyzer.

The purified protein standard was concentrated by ultrafiltration and subjected to buffer solution exchange, and finally concentrated to obtain a concentration of 25 μM or higher in an aqueous solution of 10 mM ADA (N-(2-acetamido)iminodiacetic acid) buffer (pH 6.5)-300 mM NaCl-100 μM mineral ion cocktail ($Ca(OAc)_2$, $Zn(OAc)_2.2H_2O$, $Cu(OAc)_2.H_2O$, $Co(OAc)_2.4H_2O$, $Mn(OAc)_2.4H_2O$, $Mg(OAc)_2.4H_2O$, $FeCl_3.6H_2O$). Protein concentrations were measured using BCA Protein Assay (PIERCE), in consideration of the purity calculated by SDS-PAGE.

A solution of a single pharmaceutical compound at a concentration of 1.25 mM in DMSO (dimethyl sulfoxide) or a multiplied compound solution of a plurality (8 or 16 kinds) of compounds in DMSO was prepared, and these solutions were used for interaction analysis. In reproducibility confirmation experiments or dose dependency determination experiments, a solution of various concentrations of a single compound in DMSO (dimethyl sulfoxide) was used.

Mass analysis was performed using LCQ DECA XP (Thermoelectron) or Q-TOFmicro (Micromass), equipped with an ESI probe. The LC pump used was Agilent 1100 (Yokogawa Analytical Systems), and the autosampler used was HTC-PAL (CTC Analytics) equipped with a cooling stacker.

In the SEC method using 384-well spin columns, Unifilter 100 (Whatman), packed with 10 μL (dry volume) of Bio-Gel P6 (BIO-RAD) and swollen with milliQ water, was used as the SEC column. 13.3 μL of a protein-free reference standard or a 25 μM protein standard and 0.7 μL of a multiplied liquid comprising 25 μM of each pharmaceutical compound (5% DMSO aqueous solution) were mixed; 9 μL of this mixture was aliquoted into the SEC spin columns. The SEC spin column was mounted on an acetonitrile-aliquoted 384-well U-bottom plate and centrifuged; the SEC spin column filtrate, which is a protein fraction, was retrieved in 50% acetonitrile. The protein precipitate produced by the acetonitrile was removed via centrifugation and filtration for deproteinization; the resulting filtrate was concentrated by centrifugation and re-dissolved in 10 μL of 50% methanol to obtain a mass analysis sample. The mobile phase supplied to the mass analyzer was 0.1% formic acid/50% methanol solution in the positive ion mode, and 0.1% ammonia/50% methanol solution in the negative ion mode; these mobile phases were used at a flow rate of 40 μL/min. 2-μL of mass analysis samples were injected using an autosampler at 2-minute intervals; the mass spectral intensity of the compound was measured to obtain the spectral intensity of the pharmaceutical compound contained in the SEC spin column filtrate (protein fraction eluted from SEC). The protein and the compound were judged to have interacted with each other if the spectral intensity of the compound in a mass analysis sample obtained from an SEC sample supplemented with a protein standard was greater than the spectral intensity of the compound in a mass analysis sample of reference SEC standard not supplemented with the protein. In the experiments for examining dose dependency, the protein and the compound were judged to have interacted with each other dose-dependently if the spectral intensity of the pharmaceutical compound contained in the SEC spin column filtrate (protein fraction eluted from SEC) increased as the compound concentration or/and protein concentration of the SEC sample was increased.

Example 1

Analysis of Interaction Between FLJ39196 Clone-Derived Protein and Atorvastatin

The FLJ39196 clone-derived protein was expressed and purified according to the methods of Reference Examples 1 and 2, and the interaction between the protein expressed and purified from FLJ39196 and atorvastatin was analyzed according to the method of Reference Example 3. The results are shown in Table 1. The spectrum intensity of the pharmaceutical compound contained in the SEC spin column filtrate (protein fraction eluted from SEC) increased depending on the doses of both atorvastatin and the FLJ39196 expressed protein, from which we determined that it was a dose-dependent interaction.

TABLE 1

Measured Mass Range: m/z = 559.25-559.5

| FLJ39196-atorvastatin | | compound (μM) | | | |
|---|---|---|---|---|---|
| | | 0 | 12.5 | 25 | 62.5 |
| protein (μM) | 0 | 53987 | 31597 | 68345 | 604452 |
| | 5 | 56604 | 247204 | 110996 | 2703426 |
| | 10 | 117020 | 569000 | 597628 | 3448280 |
| | 25 | 164530 | 1285142 | 2719479 | 7108230 |

Hence, the FLJ39196 derived protein was found to be a target protein for atorvastatin, which is a kind of statin compound developed as an anti-cholesterol drug, and which is acknowledge for its effects such as an anti-dementia (Alzheimer) drug. Therefore, a new anti-dementia drug can be screened by making screening candidate substances interact with the FLJ39196-derived protein. Specifically, a new anti-dementia (Alzheimer) drug can be screened by, for example, constructing a system which detects the interaction between the FLJ39196-derived protein and a candidate substance according to Example 1.

Example 2

Analysis of Interaction Between FLJ39196 Clone-Derived Protein and Various Compounds The FLJ39196 clone-derived protein was expressed and purified according to the methods of Reference Examples 1 and 2, and the interaction between the protein expressed and purified from FLJ39196 and various compounds was analyzed according to the method of Reference Example 3. The results are shown in Table 2 to 28. The spectrum intensity of the pharmaceutical compound-contained in the SEC spin column filtrate (protein fraction eluted from SEC) increased depending on the doses of both the FLJ39196-expressed protein and the various compounds, from which we determined that there was a dose-dependent interaction.

TABLE 2

Measured Mass Range: m/z = 461.8-462.8

| FLJ39196 - pimozide | | compound (μM) | | | | |
|---|---|---|---|---|---|---|
| | | 0 | 1 | 10 | 100 | 250 |
| protein (μM) | 0 | 18219277 | 4813337 | 4354460 | 5504067 | 9203835 |
| | 23.75 | 5818424 | 6161857 | 27706749 | 456093959 | 1174368945 |
| | 47.5 | 5080308 | 8507799 | 142633352 | 1412301047 | 2935095895 |

TABLE 3

Measured Mass Range: total of ①m/z = 310.7-311.7 and ②m/z(Na ion adduct) = 332.6-333.6

| FLJ39196 - Bifonazole | | compound (μM) | | | | |
|---|---|---|---|---|---|---|
| | | 0 | 1 | 10 | 100 | 250 |
| protein (μM) | 0 | 38593590 | 32068857 | 34579053 | 30705006 | 32278650 |
| | 23.75 | 37989067 | 27516354 | 30253800 | 60323012 | 85169446 |
| | 47.5 | 34294270 | 33844567 | 38342358 | 152159135 | 322219706 |

TABLE 4

Measured Mass Range: m/z = 298.7-299.7

| FLJ39196 - Fendiline | | compound (μM) | | | | |
|---|---|---|---|---|---|---|
| | | 0 | 1 | 10 | 100 | 250 |
| protein (μM) | 0 | 16096640 | 18341826 | 21106520 | 134902492 | 315067466 |
| | 23.75 | 15565227 | 15884361 | 18323956 | 118321460 | 396979100 |
| | 47.5 | 5343412 | 24572438 | 26691498 | 256481478 | 565679716 |

TABLE 5

Measured Mass Range: m/z = 329.7-330.7

| FLJ39196 - chloperastine | | compound (μM) | | | | |
|---|---|---|---|---|---|---|
| | | 0 | 1 | 10 | 100 | 250 |
| protein (μM) | 0 | 5350191 | 2920008 | 13165487 | 276180260 | 803023959 |
| | 23.75 | 3537409 | 2972794 | 9288224 | 218420294 | 773924506 |
| | 47.5 | 2912771 | 4085344 | 18612563 | 338617522 | 1411536255 |

TABLE 6

Measured Mass Range: m/z = 366.7-367.7

| FLJ39196 - Bepridil | | compound (μM) | | | | |
|---|---|---|---|---|---|---|
| | | 0 | 1 | 10 | 100 | 250 |
| protein (μM) | 0 | 11238373 | 9581826 | 14048756 | 358168208 | 1566782176 |
| | 23.75 | 7541774 | 7408112 | 35655439 | 771184721 | 1841002486 |
| | 47.5 | 6335047 | 7866658 | 40680909 | 1156825217 | 1990085657 |

TABLE 7

Measured Mass Range: m/z = 473.7-474.7

| FLJ39196 - Raloxifene hydrochloride | | compound (μM) | | | | |
|---|---|---|---|---|---|---|
| | | 0 | 1 | 10 | 100 | 250 |
| protein (μM) | 0 | 17843366 | 3754698 | 2330594 | 7909682 | 10553153 |
| | 23.75 | 4991164 | 3790373 | 6024709 | 124641622 | 157539770 |
| | 47.5 | 4375846 | 3014448 | 17385466 | 122918120 | 666932700 |

TABLE 8

Measured Mass Range: m/z = 423.2-424.2

| FLJ39196 - Benzbromarone | | compound (μM) | | | | |
|---|---|---|---|---|---|---|
| | | 0 | 1 | 10 | 100 | 250 |
| protein (μM) | 0 | 327259 | 231212 | 300847 | 378850 | 461737 |
| | 23.75 | 301936 | 357666 | 1258120 | 10722991 | 19795682 |
| | 47.5 | 353375 | 412022 | 1942184 | 29076230 | 43413619 |

TABLE 9

Measured Mass Range: m/z = 324.7-325.7

| FLJ39196 - prazepam | | compound (μM) | | | | |
|---|---|---|---|---|---|---|
| | | 0 | 1 | 10 | 100 | 250 |
| protein (μM) | 0 | 57513356 | 45379226 | 21988256 | 130413200 | 139016191 |
| | 23.75 | 28065745 | 38417587 | 46660512 | 258681345 | 517983224 |
| | 47.5 | 30688137 | 26479402 | 67670753 | 264065408 | 706383483 |

TABLE 10

Measured Mass Range: m/z = 318.7-319.7

| FLJ39196 - clotiazepam | | compound (μM) | | | | |
|---|---|---|---|---|---|---|
| | | 0 | 1 | 10 | 100 | 250 |
| protein (μM) | 0 | 8807574 | 8089543 | 19826757 | 251469420 | 633414607 |
| | 23.75 | 7459143 | 8254340 | 25038949 | 283452799 | 759706893 |
| | 47.5 | 7176640 | 9022620 | 60448900 | 657940514 | 1089985810 |

TABLE 11

Measured Mass Range: m/z = 337.7-338.7

| FLJ39196 - Suloctidil | | compound (μM) | | | | |
|---|---|---|---|---|---|---|
| | | 0 | 1 | 10 | 100 | 250 |
| protein (μM) | 0 | 3542413 | 6080126 | 3684060 | 4969067 | 9177432 |
| | 23.75 | 6558607 | 4318261 | 7828150 | 163940015 | 357100809 |
| | 47.5 | 4836197 | 5977944 | 7209043 | 507388292 | 742015343 |

TABLE 12

Measured Mass Range: m/z = 411.8-412.8

| FLJ39196 - Benzethonium | | compound (μM) | | | | |
|---|---|---|---|---|---|---|
| | | 0 | 1 | 10 | 100 | 250 |
| protein (μM) | 0 | 22495292 | 7744717 | 5781630 | 110985750 | 3418189873 |
| | 23.75 | 8694278 | 7361705 | 346972055 | 5864609237 | 6839519322 |
| | 47.5 | 9038570 | 18097692 | 724595729 | 9268734340 | 14536894458 |

TABLE 13

Measured Mass Range: m/z = 428.9-429.9

| FLJ39196 - Bicaltamide | | compound (μM) | | | | |
|---|---|---|---|---|---|---|
| | | 0 | 1 | 10 | 100 | 250 |
| protein (μM) | 0 | 1319316 | 196020 | 269681 | 3889442 | 1804944 |
| | 23.75 | 278471 | 264437 | 914364 | 18349511 | 53664833 |
| | 47.5 | 191214 | 390946 | 4168309 | 24933110 | 112816687 |

TABLE 14

Measured Mass Range: m/z = 430.2-431.2

| FLJ39196 - Benzthiazide | | compound (μM) | | | | |
|---|---|---|---|---|---|---|
| | | 0 | 1 | 10 | 100 | 250 |
| protein (μM) | 0 | 1189971 | 271261 | 505597 | 1323031 | 1475428 |
| | 23.75 | 315296 | 361168 | 1095223 | 9348303 | 25333199 |
| | 47.5 | 176906 | 249695 | 1261413 | 16067473 | 28434802 |

TABLE 15

Measured Mass Range: m/z = 298.7-299.7

| | | \multicolumn{5}{c}{compound (μM)} | | | | |
|---|---|---|---|---|---|---|
| FLJ39196 - Minaprine | | 0 | 1 | 10 | 100 | 250 |
| protein (μM) | 0 | 16639217 | 15652447 | 95722839 | 530918568 | 1025547751 |
| | 23.75 | 9882171 | 10946604 | 88615018 | 727082711 | 1272226745 |
| | 47.5 | 8025117 | 10185140 | 49245292 | 427303459 | 1448860391 |

TABLE 16

Measured Mass Range: m/z = 407.7-408.7

| | | \multicolumn{5}{c}{compound (μM)} | | | | |
|---|---|---|---|---|---|---|
| FLJ39196 - Trifluoperazine | | 0 | 1 | 10 | 100 | 250 |
| protein (μM) | 0 | 9858178 | 6645734 | 7904072 | 204390563 | 632906281 |
| | 23.75 | 6423833 | 7580781 | 40058178 | 293702761 | 1292987653 |
| | 47.5 | 5642729 | 7231665 | 14142338 | 5846308 | 2293500744 |

TABLE 17

Measured Mass Range: m/z = 315.7-316.7

| | | \multicolumn{5}{c}{compound (μM)} | | | | |
|---|---|---|---|---|---|---|
| FLJ39196 - Chlorprothixene | | 0 | 1 | 10 | 100 | 250 |
| protein (μM) | 0 | 20818137 | 12908294 | 15368592 | 30558420 | 80321853 |
| | 23.75 | 20012122 | 21615977 | 31548696 | 104338961 | 243359670 |
| | 47.5 | 18192912 | 25013147 | 52145413 | 207034486 | 433637183 |

TABLE 18

Measured Mass Range: m/z = 293.7-294.7

| | | \multicolumn{5}{c}{compound (μM)} | | | | |
|---|---|---|---|---|---|---|
| FLJ39196 - Pimethixene | | 0 | 1 | 10 | 100 | 250 |
| protein (μM) | 0 | 3544903 | 2913965 | 4868887 | 58800844 | 224525009 |
| | 23.75 | 3278835 | 2449690 | 5737072 | 121577640 | 265475649 |
| | 47.5 | 2729497 | 2762592 | 9271060 | 197624997 | 359356100 |

TABLE 19

Measured Mass Range: m/z = 434.7-438.7

| | | \multicolumn{5}{c}{compound (μM)} | | | | |
|---|---|---|---|---|---|---|
| FLJ39196 - Flupentixol cis-(Z) | | 0 | 1 | 10 | 100 | 250 |
| protein (μM) | 0 | 42590489 | 57845690 | 59201705 | 138331819 | 1019443291 |
| | 23.75 | 36874292 | 38801184 | 66148127 | 474717521 | 1437323119 |
| | 47.5 | 27636011 | 54783295 | 82852252 | 1301876646 | 1766098462 |

TABLE 20

Measured Mass Range: m/z = 473.2-474.2

| FLJ39196 - clofazimine | | compound (μM) | | | | |
|---|---|---|---|---|---|---|
| | | 0 | 1 | 10 | 100 | 250 |
| protein (μM) | 0 | 5613437 | 1592610 | 3306068 | 1781607 | 1742291 |
| | 23.75 | 1595172 | 2041846 | 15886830 | 138678443 | 380425425 |
| | 47.5 | 2442639 | 2399851 | 57730302 | 312686548 | 411373516 |

TABLE 21

Measured Mass Range: m/z = 327.7-328.7

| FLJ39196 - Loxapine | | compound (μM) | | | | |
|---|---|---|---|---|---|---|
| | | 0 | 1 | 10 | 100 | 250 |
| protein (μM) | 0 | 3522176 | 3432353 | 21044859 | 169361258 | 460296582 |
| | 23.75 | 3879570 | 4528499 | 11931004 | 251879811 | 825422861 |
| | 47.5 | 2827091 | 4199361 | 15635610 | 339486695 | 830945491 |

TABLE 22

Measured Mass Range: m/z = 634.9-635.9

| FLJ39196 - Rescinnamine | | compound (μM) | | | | |
|---|---|---|---|---|---|---|
| | | 0 | 1 | 10 | 100 | 250 |
| protein (μM) | 0 | 11639431 | 9843174 | 6544896 | 12903374 | 7315419 |
| | 23.75 | 12301790 | 11269941 | 21895843 | 215933519 | 288844471 |
| | 47.5 | 13358537 | 17653515 | 40677751 | 675671326 | 1469409087 |

TABLE 23

Measured Mass Range: m/z = 666.8-667.8

| FLJ39196 - Syrosingopine | | compound (μM) | | | | |
|---|---|---|---|---|---|---|
| | | 0 | 1 | 10 | 100 | 250 |
| protein (μM) | 0 | 52552166 | 38126829 | 47209784 | 41362697 | 38512184 |
| | 23.75 | 56051742 | 63594361 | 101347281 | 465474678 | 596250311 |
| | 47.5 | 55701703 | 70443152 | 105524442 | 897067633 | 1499127775 |

TABLE 24

Measured Mass Range: m/z = 564.1-565.1

| FLJ39196 - Dihydroergotoxine mesylate | | compound (μM) | | | | |
|---|---|---|---|---|---|---|
| | | 0 | 1 | 10 | 100 | 250 |
| protein (μM) | 0 | 28173635 | 25150786 | 29311635 | 76261189 | 326128137 |
| | 23.75 | 20474057 | 19680823 | 36914079 | 177369018 | 232715490 |
| | 47.5 | 14315178 | 16556794 | 45033425 | 221983211 | 530510575 |

TABLE 25

Measured Mass Range: m/z = 577.9-578.9

| FLJ39196 - Dihydroergotoxine mesylate | | compound (μM) | | | | |
|---|---|---|---|---|---|---|
| | | 0 | 1 | 10 | 100 | 250 |
| protein (μM) | 0 | 20191674 | 17036968 | 25343556 | 62894601 | 234871658 |
| | 23.75 | 15759781 | 25890358 | 111382606 | 421344902 | 408003600 |
| | 47.5 | 17285522 | 31988946 | 207450982 | 908698063 | 1265975868 |

TABLE 26

Measured Mass Range: m/z = 611.7-612.7

| FLJ39196 - Dihydroergotoxine mesylate | | compound (μM) | | | | |
|---|---|---|---|---|---|---|
| | | 0 | 1 | 10 | 100 | 250 |
| protein (μM) | 0 | 33357241 | 18486648 | 24024699 | 30737736 | 58888872 |
| | 23.75 | 25102744 | 35126832 | 106708813 | 397014202 | 267260198 |
| | 47.5 | 31509157 | 40595551 | 194133547 | 931095764 | 1112309560 |

TABLE 27

Measured Mass Range: m/z = 611.9-612.9

| FLJ39196 - Dihydroergocristine | | compound (μM) | | | | |
|---|---|---|---|---|---|---|
| | | 0 | 1 | 10 | 100 | 250 |
| protein (μM) | 0 | 34818618 | 25663523 | 10810305 | 75466444 | 137535150 |
| | 23.75 | 28551541 | 68120944 | 327393156 | 910395859 | 871970698 |
| | 47.5 | 38121433 | 95970671 | 593118709 | 1961163889 | 2985742521 |

TABLE 28

Measured Mass Range: m/z = 328.9-329.9

| FLJ39196 - stanozolol | | compound (μM) | | | | |
|---|---|---|---|---|---|---|
| | | 0 | 1 | 10 | 100 | 250 |
| protein (μM) | 0 | 8793284 | 3108300 | 2749518 | 3830491 | 4150230 |
| | 23.75 | 3069987 | 3620481 | 10223886 | 127989356 | 194560574 |
| | 47.5 | 2505684 | 3989532 | 25533379 | 619287498 | 778914733 |

Hence, the FLJ39196-derived protein was found to be a target protein for these various compounds. Therefore, a new drug can be screened by making screening candidate substances interact with the FLJ39196-derived protein. Specifically, a new drug can be screened by, for example, constructing a system which detects the interaction between the FLJ39196-derived protein and a candidate substance according to the method of Example 1.

Example 3
Analysis of Interaction Between FLJ20589 Clone-Derived Protein and Various Compounds The FLJ20589 clone-derived protein was expressed and purified according to the methods of Reference Examples 1 and 2, and the interaction between the protein expressed and purified from FLJ20589 and various compounds was analyzed according to the method of Reference Example 3. The results are shown in Table 29 to 33. The spectrum intensity of the pharmaceutical compound contained in the SEC spin column filtrate (protein fraction eluted from SEC) increased depending on the doses of both the FLJ20589-expressed protein and the various compounds, from which we determined that there was a dose-dependent interaction.

TABLE 29

Measured Mass Range: total of ① m/z = 310.8-311.8 and
② m/z(Na ion adduct) = 332.9-333.9

| FLJ20589 - Bifonazole | | compound (μM) | | | |
|---|---|---|---|---|---|
| | 0 | 1 | 10 | 100 | 250 |
| protein (μM) 0 | 3600159 | 2704636 | 2935358 | 2558136 | 3779926 |
| 23.75 | 2324791 | 2343078 | 2189489 | 3826699 | 3607174 |
| 47.5 | 2094320 | 1367901 | 2513645 | 8024232 | 28949362 |

TABLE 30

Measured Mass Range: m/z = 325.1-326.1

| FLJ20589 - Prazepam | | compound (μM) | | | |
|---|---|---|---|---|---|
| | 0 | 1 | 10 | 100 | 250 |
| protein (μM) 0 | 696402 | 563508 | 752185 | 5911478 | 8158416 |
| 23.75 | 438127 | 372254 | 1912944 | 27662748 | 53037838 |
| 47.5 | 172968 | 603084 | 8279573 | 67316791 | 87274751 |

TABLE 31

Measured Mass Range: m/z = 412.0-413.0

| FLJ20589 - Benzethonium | | compound (μM) | | | |
|---|---|---|---|---|---|
| | 0 | 1 | 10 | 100 | 250 |
| protein (μM) 0 | 2920130 | 681042 | 536408 | 1019183 | 1894576 |
| 23.75 | 852430 | 567621 | 13777320 | 732075554 | 363052655 |
| 47.5 | 169123 | 179741 | 1125025 | 368271326 | 1844957985 |

TABLE 32

Measured Mass Range: m/z = 408.1-409.1

| FLJ20589 - Trifluoperazine | | compound (μM) | | | |
|---|---|---|---|---|---|
| | 0 | 1 | 10 | 100 | 250 |
| protein (μM) 0 | 1872134 | 1499445 | 1420853 | 2266965 | 4146130 |
| 23.75 | 548622 | 469062 | 893634 | 41947038 | 57062370 |
| 47.5 | 226024 | 459554 | 2953415 | 67433540 | 116228047 |

TABLE 33

Measured Mass Range: m/z = 405.1-406.1

| FLJ20589 - Flunarizine | | compound (μM) | | | |
|---|---|---|---|---|---|
| | 0 | 1 | 10 | 100 | 250 |
| protein (μM) 0 | 418270 | 188851 | 200579 | 198757 | 253795 |
| 23.75 | 185731 | 501950 | 137693 | 181386 | 308575 |
| 47.5 | 154411 | 58869 | 178128 | 2683794 | 9317332 |

Hence, the FLJ20589-derived protein was found to be a target protein for these various compounds. Therefore, a new drug can be screened by making screening candidate substances interact with the FLJ20589-derived protein. Specifically, a new drug can be screened by, for example, constructing a system which detects the interaction between the FLJ20589-derived protein and a candidate substance according to the method of Example 1.

Example 4

Docking Study of FLJ39196 or FLJ20589 Clone-Derived Protein and Various Compounds Next, using FLJ39196 or FLJ20589 clone-derived protein as the target protein, docking study was performed with the various compounds mentioned above.

As a result, since the compounds as set forth in formula (I) to (VIII), (1) to (11), and (1') to (11') of the present invention or its salts or the like can bind with FLJ39196 or FLJ20589, it was considered that they can regulate the function of FLJ39196 or FLJ20589 clone-derived protein.

From the above, the compounds as set forth in formula (I) to (VIII), (1) to (11), and (1') to (11') of the present invention or its salts or the like are considered to be useful for prevention and treatment of subject diseases such as dementia and the like, or other purposes mentioned within this specification.

Industrial Applicability

The target proteins and target genes of the present invention enable the development of drugs such as anti-central nervous disease drugs, and the like. The screening methods of the present invention and the derivative production method of the present invention enable the development of prophylactic or therapeutic agents for diseases such as central nervous disease, and investigational reagents for the diseases, and the like. The regulator and derivatives of the present invention can be used for the prophylaxis and treatment of diseases such as central nervous disease, and the development of investigational reagents for the diseases, and the like. The complexes and kits of the present invention can be used for the screening methods of the present invention, and the like. The determination methods and determination kits of the present invention enable the evaluation of the onset or likelihood of onset of diseases in animals, the evaluation of the susceptibility of animals to drugs, and the like.

This application is based on a patent application No. 2004-304864 filed in Japan (filing date: Oct. 19, 2004), the contents of which are incorporated in full herein by this reference.

The invention claimed is:

1. A method for screening a drug, which comprises evaluating whether or not a test substance regulates the expression or function of an NCS protein gene by performing the following steps (a) to (c):
   (a) a step for bringing the test substance into contact with the NCS protein or mutant protein thereof;
   (b) a step for measuring the functional level of the NCS protein or mutant protein thereof in the presence of the test substance, and comparing said functional level with the functional level of the NCS protein or mutant protein thereof in the absence of the test substance;
   (c) a step for selecting a test substance that alters the functional level of the NCS protein or mutant protein thereof on the basis of the result of the comparison in (b) above.

2. The method according to claim 1, wherein the drug regulates central nervous action, dementia action, or Alzheimer's disease action.

3. The method according to claim 1, wherein the drug regulates an action associated with an NCS protein-targeting drug.

4. The method according to claim 1, wherein the NCS protein gene is a neurocalcin gene.

5. The method according to claim 1, wherein the NCS protein gene is a neurocalcin δ gene.

6. The method according to claim 1, wherein the NCS protein or mutant protein thereof is an NCS protein.

7. A method for screening a drug, which comprises evaluating whether or not a test substance regulates the expression or function of an NCS protein gene by performing the following steps (a) to (c):
   (a) a step for bringing the test substance into contact with cells enabling a measurement of the expression of the NCS protein or a gene encoding the NCS protein;
   (b) a step for measuring the expression level of the NCS protein or the gene in the cells in contact with the test substance, and comparing said expression level with the expression level of the NCS protein or the gene in control cells not in contact with the test substance;
   (c) a step for selecting a test substance that regulates the expression level of the NCS protein or the gene on the basis of the result of the comparison in step (b) above.

8. The method according to claim 7, wherein the drug regulates central nervous action, dementia action, or Alzheimer's disease action.

9. The method according to claim 7, wherein the drug regulates an action associated with an NCS protein-targeting drug.

10. The method according to claim 7, wherein the NCS protein gene is a neurocalcin gene.

11. The method according to claim 7, wherein the NCS protein gene is a neurocalcin δ gene.

12. A method for screening a drug, which comprises evaluating whether or not a test substance regulates the expression or function of an NCS protein gene by performing the following steps (a) to (c):
   (a) a step for bringing the test substance into contact with an NCS protein or a mutant protein thereof;
   (b) a step for measuring the ability of the test substance to bind to the NCS protein or mutant protein thereof;
   (c) a step for selecting a test substance that has the binding ability to the NCS protein or mutant protein thereof on the basis of the result of step (b) above.

13. The method according to claim 12, wherein the drug regulates central nervous action, dementia action, or Alzheimer's disease action.

14. The method according to claim 12, wherein the drug regulates an action associated with an NCS protein-targeting drug.

15. The method according to claim 12, wherein the NCS protein gene is a neurocalcin gene.

16. The method according to claim 12, wherein the NCS protein gene is a neurocalcin δ gene.

17. The method according to claim 12, wherein the NCS protein or mutant protein thereof is an NCS protein.

18. A method for screening a drug, which comprises evaluating whether or not a test substance regulates the expression or function of an NCS protein gene by performing the following steps (a) to (c):
   (a) a step for bringing the test substance and an NCS protein-binding substance into contact with an NCS protein or a mutant protein thereof;
   (b) a step for measuring the binding amount of the NCS protein-binding substance to the NCS protein or mutant protein thereof in the presence of the test substance, and comparing the amount with the binding amount of the NCS protein-binding substance to the NCS protein or mutant protein thereof in the absence of the test substance;
   (c) a step for selecting a test substance that alters the binding amount of the NCS protein-binding substance to the NCS protein or mutant protein thereof on the basis of the result of the comparison in step (b) above.

19. The method according to claim 18, wherein the NCS protein-binding substance is atorvastatin, pimozide, bifonazole, flunarizine, fendiline, chloperastine, bepridil, raloxifene hydrochloride, benzbromarone, prazepam, clotiazepam, suloctidil, benzethonium, bicaltamide, benzthiazide, minaprine, trifluoperazine, chlorprothixene, pimethixene, flupentixol, clofazimine, loxapine, rescinnamine, syrosingopine, dihydroergocornine mesylate, dihydro-α-ergocryptine mesylate, dihydro-β-ergocryptine mesylate, dihydroergocristine mesylate or stanozolol, or a derivative thereof.

20. The method according to claim 18, wherein the drug regulates central nervous action, dementia action, or Alzheimer's disease action.

21. The method according to claim 18, wherein the drug regulates an action associated with an NCS protein-targeting drug.

22. The method according to claim 18, wherein the NCS protein gene is a neurocalcin gene.

23. The method according to claim 18, wherein the NCS protein gene is a neurocalcin δ gene.

24. The method according to claim 18, wherein the NCS protein or mutant protein thereof is an NCS protein.

25. A method for screening for a substance that regulates a function associated with an NCS protein gene, which comprises determining whether or not a test substance regulates the binding of an NCS protein-targeting drug to the NCS protein or a mutant protein thereof by performing the following steps (a) to (c):
   (a) a step for bringing the test substance and the NCS protein-targeting drug into contact with the NCS protein or the mutant protein thereof;
   (b) a step for measuring the binding amount of the NCS protein-targeting drug to the NCS protein or mutant protein thereof in the presence of the test substance, and comparing the binding amount with the binding amount of the NCS target drug to the NCS protein or mutant protein thereof in the absence of the test substance;
   (c) a step for selecting a test substance that alters the binding amount of the NCS protein-targeting drug to the NCS protein or mutant protein thereof on the basis of the result of the comparison in step (b) above.

26. The method according to claim 25, wherein the NCS protein-targeting drug is atorvastatin, pimozide, bifonazole, flunarizine, fendiline, chioperastine, bepridil, raloxifene hydrochloride, benzbromarone, prazepam, clotiazepam, suloctidil, benzethonium, bicaltamide, benzthiazide, minaprine, trifluoperazine, chlorprothixene, pimethixene, flupentixol, clofazimine, loxapine, rescinnamine, syrosingopine, dihydroergocornine mesylate, dihydro-α-ergocryptine mesylate, dihydro-β-ergocryptine mesylate, dihydroergocristine mesylate or stanozolol, or a derivative thereof having the ability to bind to NCS.

27. The method according to claim 25, wherein the NCS protein or mutant protein thereof is an NCS protein.

* * * * *

SEQUENCE LISTING

<160> NUMBER OF SEQ ID NOS: 4

<210> SEQ ID NO 1
<211> LENGTH: 3667
<212> TYPE: DNA
<213> ORGANISM: Homo sapiens

<400> SEQUENCE: 1

```
agacgctggg agcggccgag gcgagatcct atcattattt taaaattcct cctcctccac      60
gaagtccttc ctgattcctt caaagaaata tcactcctcc gaattcccag agtgatttct     120
tctgacttga gcctgcagtg tgctgtgaga gatctaccac tagattatct caactttggt     180
ctcctgggac cactcgttgc tgacagtcag aaattgcagg gcatctgatc tcctggtgtt     240
aaaatctgtc gtgataccga ggaaggcccc gagatcccag gcactgagtg actgcatact     300
ctgaattctt gccgccagga tggggaaaca gaacagcaag ctgcgcccgg aggtcatgca     360
ggacttgctg gaaagcacag actttacaga gcatgagatc caggaatggt ataaaggctt     420
cttgagagac tgccccagtg gacatttgtc aatggaagag tttaagaaaa tatatgggaa     480
ctttttccct tatggggatg cttccaaatt tgcagagcat gtcttccgca ccttcgatgc     540
aaatggagat gggacaatag actttagaga attcatcatc gccttgagtg taacttcgag     600
ggggaagctg gagcagaagc tgaaatgggc cttcagcatg tacgacctgg acggaaatgg     660
ctatatcagc aaggcagaga tgctagagat cgtgcaggca atctataaga tggtttcctc     720
tgtaatgaaa atgcctgaag atgagtcaac cccagagaaa agaacagaaa agatcttccg     780
ccagatggac accaatagag acggaaaact ctccctggaa gagttcatcc gaggagccaa     840
aagcgacccg tccattgtgc gcctcctgca gtgcgacccg agcagtgccg gccagttctg     900
agccctgcgc ccaccaatcg aattgtagag ctgcttgtgt tcccttttga ttcttctttt     960
taacaatttt ttttttttt tgccaaacaa tatcaatggt gatgccgtcc cctgtgcggt    1020
ctgatgcgcc ttcctccgtg acgccttcag cttcttttgt cgtggatgct tcgtgggaat    1080
gcccagagcc ccagtgtgct tgtggagagc atggacagac ttcgtggtgt tcattgtttg    1140 atgatttta atcgttacta ttatttttt ttattctaat gtctctgttc taaaacgtaa    1200
gactcggggg ttggggcaaa agaagggaaa cccatccagt cctgtgattc tattgcaagc    1260 ctcaagggc ttttgtttga aagacaaaac tccccacctg aatctgttgt cacacgtgcc    1320
gtaggggtga tggatggcac cggatgctgg attccccaag aacaagttac cctctggggt    1380
gaggctattc cagcgagctg ggacatttcc ccatgggggc ccactcccct ctcttcccca    1440
gcaggctgta gtttctaagc tgtgaacatt tcaagataaa ttaacagagg agaggaaaaa    1500
gatggctcag ctatttttc acaggtttac actagttgag ctaatatgcg tgtctttgga    1560
aattaaacac aaatggtaac atattccaaa accagaccca tcttgttgcc tattgtgata    1620
aaataaaaag acggctgtat ataacatatt gggtaatgca gaccaaatta agtgttttgc    1680
cttgtttaaa tgaaatgcat gtttagtgag cactaataca atcttattcc agaagactgt    1740
ttttagtagc ttattgtgaa gtaagacaac tataatgaat gtctgtcttg tttggaagtc    1800
```

-continued

```
atatctgtct tgcacaaat gtaccaatcg acaagtatat tttatatatt ccataaaaat    1860
acaaagtaac cctgactagg gcccaacttt aattttgaat gcatttccag agtggccatg   1920
cctagagggc agatgcagag caggtggtag tgggacagga caattggagc acaggaatgt   1980
taacatgtat gacaggggac cagtagggtg gtttccctct caggcccagc agcccattga   2040
cagcattaga ctggcggcat ggtgcttttc tgagcagatc aatactctgc agactcgaaa   2100
aaacatcaca tacattcttg gaacttccca gtggtttaat ctatgtgcat ggttagggag   2160
ccaggtctgg aatattcagt ttccctgccc ctgttaaaga atcagaggtt gggcagtcat   2220
caaattcatc ataaagacat gggcaagtgt gtctgtggtt ccaaggccc ccctatggag    2280
aatccaaaag tattttccat tgccgtgctc tttgaatgca gacttctatt tccagaagtg   2340
acagcacaag tctgagttgc tgtttggtct ggtgacctca gacacactaa tttgaattga   2400
aagctaagag taaaaatttg ctggttacag gcgagtcata ctccttgcaag tagttagcaa  2460
agggaggccc aaattctcaa ggttgttgat ggggaacttg ccactaagag aaggcagaga   2520
ggtccctagt gggtatattt gctgccaagc cacttgccaa agaagaggaa ccacagaaag   2580
agagacatca tgaccaggag aaaaatgtga ctagacatgc taacctccag gttttttatat 2640
atgacttgag tctgctgtaa ttggcagcag aaatccaaat ttgtatggta gaccaaaaag   2700
aaccaaatcc ataggtgaa attttgagac ctagactctg taaaaataat cctagtcttc    2760
ctccaggggt cagttcctca cagtggttct gtaccaaaac ttgccaaatt cctccatggc   2820
caagtgttaa aatctgtgtt tggaaaatag cgaattaacc taagacacag aaggcagact   2880
gggtgaggag acctagcatg ccctattggc agtgctcagg agctgcatcc cacttttccc   2940
tgctctgaat cgaagtccta gttccttcct ttgattctcc tttggtaggt ggaatcagtt   3000
aatgttttga gaaacctgcc tgggctctgc ccttagtcat gacatctcgc tgagccagac   3060
ccactctgtt ccttggaacc tagagctgga gtgaggagta gaggtctccg gctattccag   3120
aaagaaaagt gagccacatg caggctgatg aatgccgaca cttccagaat gtatagaaat   3180
agtccctgtc ctggcctgcc actgaccctg tctgtatttt ctcggaggtt gttttttctcc  3240
ttctccttcc caggaaggtc tttgtatgtc gaatccagtg cactcaagtt tggccaaggg   3300
actccacagc acccagaaga ctgcatgcct caaggtttat gtcactcctc tgctgggctg   3360
ttcattgtca ttgctgtgtt cagggacctt tggaaataaa acctgttctg tcccaaataa   3420
aaccagcctg tgatgttcaa gggactggaa taaagtggct tacgacctga aggattctac   3480
agagtgctca actgttcata catcattcag agtgggaggg agctgggggt gctgtcccat   3540
cccatctgta tgcccacggt ggatttaata atatataatt tataaatcat agcctatgga   3600
gtggcccgta aatcagttga ctgtgtagct cttgcctggc attaaagcat gttttggtt    3660
taacatg                                                              3667
```

<210> SEQ ID NO 2
<211> LENGTH: 193
<212> TYPE: PRT
<213> ORGANISM: Homo sapiens

<400> SEQUENCE: 2

```
Met Gly Lys Gln Asn Ser Lys Leu Arg Pro Glu Val Met Gln Asp Leu
1               5                   10                  15

Leu Glu Ser Thr Asp Phe Thr Glu His Glu Ile Gln Glu Trp Tyr Lys
            20                  25                  30

Gly Phe Leu Arg Asp Cys Pro Ser Gly His Leu Ser Met Glu Glu Phe
        35                  40                  45
```

```
Lys Lys Ile Tyr Gly Asn Phe Phe Pro Tyr Gly Asp Ala Ser Lys Phe
 50                  55                  60
Ala Glu His Val Phe Arg Thr Phe Asp Ala Asn Gly Asp Gly Thr Ile
 65                  70                  75                  80
Asp Phe Arg Glu Phe Ile Ile Ala Leu Ser Val Thr Ser Arg Gly Lys
                 85                  90                  95
Leu Glu Gln Lys Leu Lys Trp Ala Phe Ser Met Tyr Asp Leu Asp Gly
                100                 105                 110
Asn Gly Tyr Ile Ser Lys Ala Glu Met Leu Glu Ile Val Gln Ala Ile
            115                 120                 125
Tyr Lys Met Val Ser Ser Val Met Lys Met Pro Glu Asp Glu Ser Thr
130                 135                 140
Pro Glu Lys Arg Thr Glu Lys Ile Phe Arg Gln Met Asp Thr Asn Arg
145                 150                 155                 160
Asp Gly Lys Leu Ser Leu Glu Glu Phe Ile Arg Gly Ala Lys Ser Asp
                165                 170                 175
Pro Ser Ile Val Arg Leu Leu Gln Cys Asp Pro Ser Ser Ala Gly Gln
                180                 185                 190
Phe

<210> SEQ ID NO 3
<211> LENGTH: 1926
<212> TYPE: DNA
<213> ORGANISM: Homo sapiens

<400> SEQUENCE: 3
aaaaaaagct tctgccaagg gtgggggccc acgcggaggc gatccgctcg ttcctcccag    60
ggccatgggg cgacgaggag agccctggcc tccccgcgac ccgcaccgcg acctgggcca   120
gacgcgccac cttccccggt cgcggtttgc ttctctttaa aatgaggaca gctcctccct   180
tgggggctgt ggtgacaggt gaaatgagaa cgcactgaag acagctcttg gtccaaagcc   240
ccgcacacag gcatggtct agtggcccag tcaggacgcg gaaacactcc ctggaggttc    300
tgacccactc cctctcagcc tccgcctggt ctctgggttg gctgttccag ctccaaagag   360
aaggaggaac cttttccttc tgcagcccct ccccaccagc cccattcctt agctggggtc   420
agacctgggg tcctcactgc agctggcctc tggcagcgtt ctcaggctag ccctccctgc   480
tgaaaagaga accgtgtggg actcacaggt gtagtcgccg ccgccagccg ccatgggcaa   540
acagaacagc aagctgcggc cgaggtgct gcaggacctg cgggagaaca cggagttcac    600
cgaccacgag ctgcaggagt ggtacaaggg cttcctcaag gactgcccca ccggccacct   660
gaccgtggac gagttcaaga gatctacgc caacttcttc ccctacggcg acgcttccaa    720
gttcgccgag cacgtcttcc gcaccttcga caccaacggc gacggcacca tcgacttccg   780
ggagttcatc attgcgctga gcgtgacctc gcggggcaag ctggagcaga agctcaagtg   840
ggccttcagc atgtacgacc tggacggcaa cggctacatc agccgcagcg agatgctgga   900
gatcgtgcag gccatctaca agatggtgtc gtctgtgatg aagatgccgg aggatgagtc   960
cacccggag aagcgcacag acaagatctt caggcagatg gacaccaaca atgacggcaa   1020
actgtccttg gaagaattca tcagaggtgc caagagcgac ccctccatcg tccgcctgct  1080
gcagtgcgac cccagcagtg ccagtcagtt ctgagcgagc ggcccctgga cagttgcaga  1140
gaaacacagg cttgtcgtgc cgtttaagct ttgcttgcaa gagtggatgc ccgcaatcg   1200
ttcctgctct cccgggcccc gggcctgggg catgcgttgc acctgccgg ccgcgtggct   1260
```

-continued

```
gcgcctccct cctccacctg accaacgcga cattcctccc ctcacgcctg gcccggtccc    1320
ttccagggca actcccaggg atgtggtgac atgcagggtt caagtgttct tggttccagg    1380
cacctcccgg ctcacgggga gctcagaggt ccatgccgag gagaccaggc aggacctccc    1440
gaggctgcgc cccggccggc ccatgcgttt tgtgatccca agtgactctg tgggaagggt    1500
ggggacgagg cgtcgggagg gtatacaggg agcccctccc gtgcatggct gccccccgt     1560 tcatttctc caccacagcc gcttgcacgt atagatactg tggtcccctt tcttttaata    1620
tataaattat gtatggtgaa gtggagtgta ttgtgtaggt cccgtattta atgcctctga    1680
ctgcctttga agcgcagccc tctgtggccc gcagcccct gagcctggct gttgtgtggt     1740
atttatgctc tctttgtctg cctgtttcta aggaaatgca tgtgtgccct gagccgtgat    1800
gatcctccca tccgtgttgt gagcacaggc atttgtgtct ggtctgtcct ccctgttgat    1860
tggtctggca tttccggtat taaaatgata aataaatgg cattttctga aaaaaaaaaa     1920
aaaaaa                                                               1926
```

<210> SEQ ID NO 4
<211> LENGTH: 193
<212> TYPE: PRT
<213> ORGANISM: Homo sapiens

<400> SEQUENCE: 4

```
Met Gly Lys Gln Asn Ser Lys Leu Arg Pro Glu Val Leu Gln Asp Leu
 1               5                  10                  15

Arg Glu Asn Thr Glu Phe Thr Asp His Glu Leu Gln Glu Trp Tyr Lys
                20                  25                  30

Gly Phe Leu Lys Asp Cys Pro Thr Gly His Leu Thr Val Asp Glu Phe
            35                  40                  45

Lys Lys Ile Tyr Ala Asn Phe Phe Pro Tyr Gly Asp Ala Ser Lys Phe
        50                  55                  60

Ala Glu His Val Phe Arg Thr Phe Asp Thr Asn Gly Asp Gly Thr Ile
65                  70                  75                  80

Asp Phe Arg Glu Phe Ile Ile Ala Leu Ser Val Thr Ser Arg Gly Lys
                85                  90                  95

Leu Glu Gln Lys Leu Lys Trp Ala Phe Ser Met Tyr Asp Leu Asp Gly
            100                 105                 110

Asn Gly Tyr Ile Ser Arg Ser Glu Met Leu Glu Ile Val Gln Ala Ile
        115                 120                 125

Tyr Lys Met Val Ser Ser Val Met Lys Met Pro Glu Asp Glu Ser Thr
    130                 135                 140

Pro Glu Lys Arg Thr Asp Lys Ile Phe Arg Gln Met Asp Thr Asn Asn
145                 150                 155                 160

Asp Gly Lys Leu Ser Leu Glu Glu Phe Ile Arg Gly Ala Lys Ser Asp
                165                 170                 175

Pro Ser Ile Val Arg Leu Leu Gln Cys Asp Pro Ser Ser Ala Ser Gln
            180                 185                 190

Phe
```